(12) United States Patent
Long et al.

(10) Patent No.: US 8,754,115 B2
(45) Date of Patent: Jun. 17, 2014

(54) FUNGICIDAL PYRAZOLES

(75) Inventors: Jeffrey Keith Long, Wilmington, DE (US); Paula Louise Sharpe, Middletown, DE (US); Amy X Ding, Wilmington, DE (US)

(73) Assignee: E I du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 13/816,847

(22) PCT Filed: Aug. 31, 2011

(86) PCT No.: PCT/US2011/049908
§ 371 (c)(1),
(2), (4) Date: Feb. 13, 2013

(87) PCT Pub. No.: WO2012/030922
PCT Pub. Date: Mar. 8, 2012

(65) Prior Publication Data
US 2013/0143940 A1    Jun. 6, 2013

Related U.S. Application Data

(60) Provisional application No. 61/379,159, filed on Sep. 1, 2010.

(51) Int. Cl.
*A61K 31/415* (2006.01)
*C07D 231/10* (2006.01)

(52) U.S. Cl.
USPC ..... 514/406; 514/407; 548/370.4; 548/370.7; 548/371.4; 548/371.7; 548/374.1; 548/376.1; 548/377.1

(58) Field of Classification Search
USPC ......... 514/406, 407; 548/370.4, 370.7, 371.4, 548/371.7, 374.1, 376.1, 377.1
See application file for complete search history.

(56) References Cited

FOREIGN PATENT DOCUMENTS

| EP | 0 118 205 A1 | 9/1984 |
|---|---|---|
| GB | 1 484 968 | 9/1977 |
| JP | 49 101373 A | 9/1974 |
| JP | 05051304 A | 3/1993 |
| WO | 2009/007098 A1 | 1/2009 |
| WO | 2009/007098 A8 | 1/2009 |
| WO | 2010/101973 A1 | 9/2010 |
| WO | 2012/023143 A1 | 2/2012 |
| WO | 2012/031061 A2 | 3/2012 |

OTHER PUBLICATIONS

Akbas et al., "Antibacterial and Antifungal Activities of New Pyrazolo[3,4-D]Pyridazine Derivatives", European Journal of Medicinal Chemistry, 2005, vol. 40, Issue 4, 401-405.
Negri et al., "Study of the Reactivity of Alpa—Acyl Enamino Ketones. Synthesis of Pyrazoles", Journal of Heterocyclic Chemistry, 2001, vol. 38, Issue 1, 109-123.
Chemical Abstracts Service, XP002662671, Database Accession No. 1975:140121.
Michael G. Hoffmann, "A New Route to 1,5-Disubstituted 4-Arylsulfonylpyrazoles by Lithiation of 1-Methyl-4-Arylsulfonylpyrazoles", Tetrahedron vol. 51, pp. 9511-9518, 1995.

*Primary Examiner* — Samantha Shterengarts
(74) *Attorney, Agent, or Firm* — Charlene Gross Sternberg

(57) ABSTRACT

Disclosed are compounds of Formula 1 and Formula 1A including all stereoisomers, N-oxides, and salts thereof,

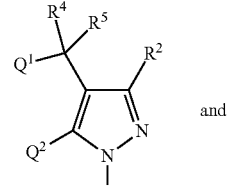

and

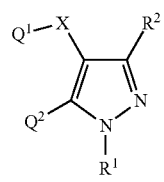

wherein
$Q^1$, $Q^2$, $R^1$, $R^2$, $R^4$, $R^5$ and X are as defined in the disclosure.

Also disclosed are compositions containing the compounds of Formula 1 or Formula 1A and methods for controlling plant disease caused by a fungal pathogen comprising applying an effective amount of a compound or a composition of the invention.

10 Claims, No Drawings

FUNGICIDAL PYRAZOLES

FIELD OF THE INVENTION

This invention relates to certain pyrazoles, their N-oxides, salts and compositions, and methods of their use as fungicides.

BACKGROUND OF THE INVENTION

The control of plant diseases caused by fungal plant pathogens is extremely important in achieving high crop efficiency. Plant disease damage to ornamental, vegetable, field, cereal, and fruit crops can cause significant reduction in productivity and thereby result in increased costs to the consumer. Many products are commercially available for these purposes, but the need continues for new compounds which are more effective, less costly, less toxic, environmentally safer or have different sites of action.

PCT Patent Publication WO 2009/007098 A1 discloses certain pyrazole derivatives as fungicides.

SUMMARY OF THE INVENTION

This invention is directed to compounds of Formula 1 (including all stereoisomers), N-oxides, and salts thereof, agricultural compositions containing them and their use as fungicides:

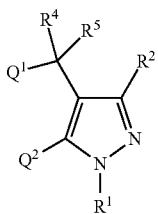

1 wherein
- $Q^1$ is a phenyl ring substituted with 1 to 5 substituents independently selected from $R^{3a}$;
- $Q^2$ is a phenyl ring substituted with 1 to 5 substituents independently selected from $R^{3a}$; or a 5- to 6-membered fully unsaturated heterocyclic ring, each ring containing ring members selected from carbon atoms and 1 to 3 heteroatoms independently selected from up to 2 O, up to 2 S and up to 3 N atoms, wherein up to 2 carbon ring members are independently selected from C(=O) and C(=S), each ring optionally substituted with up to 5 substituents independently selected from $R^{3a}$ on carbon atom ring members and $R^{3b}$ on nitrogen atom ring members;
- $R^1$ is $C_1$-$C_2$ alkyl, halomethyl, cyanomethyl or cyclopropyl;
- $R^2$ is H, halogen, cyano, $C_1$-$C_2$ alkyl, $C_2$-$C_4$ alkenyl, $C_2$-$C_4$ alkynyl, $C_1$-$C_2$ haloalkyl, $C_2$-$C_3$ cyanoalkyl, $C_1$-$C_2$ hydroxyalkyl, cyclopropyl, halocyclopropyl, $C_2$-$C_3$ alkoxyalkyl, $C_1$-$C_2$ alkylthio, $C_1$-$C_2$ alkoxy or $C_1$-$C_2$ haloalkoxy;
- each $R^{3a}$ is independently halogen, cyano, hydroxy, nitro, amino, $C_1$-$C_3$ alkyl, $C_2$-$C_4$ alkenyl, $C_2$-$C_4$ alkynyl, $C_1$-$C_3$ haloalkyl, $C_3$-$C_6$ cycloalkyl, $C_3$-$C_6$ halocycloalkyl, $C_4$-$C_6$ alkylcycloalkyl, $C_4$-$C_6$ cycloalkylalkyl, $C_1$-$C_3$ alkylthio, $C_1$-$C_3$ haloalkylthio, $C_1$-$C_3$ alkylsulfinyl, $C_1$-$C_3$ haloalkylsulfinyl, $C_1$-$C_3$ alkylsulfonyl, $C_1$-$C_3$ haloalkylsulfonyl, $C_1$-$C_3$ alkoxy, $C_1$-$C_3$ haloalkoxy, $C_3$-$C_6$ cycloalkoxy, $C_1$-$C_3$ alkylsulfonyloxy, $C_1$-$C_3$ haloalkylsulfonyloxy, $C_2$-$C_4$ alkylcarbonyloxy, $C_2$-$C_4$ alkylcarbonyl, $C_1$-$C_3$ alkylamino, $C_2$-$C_4$ dialkylamino, $C_2$-$C_4$ alkylcarbonylamino, —CH(=O), —NHCH(=O), —SF$_5$, —SC≡N or —U—V-T;
- each $R^{3b}$ is independently cyano, $C_1$-$C_3$ alkyl, $C_2$-$C_4$ alkenyl, $C_2$-$C_4$ alkynyl, $C_3$-$C_6$ cycloalkyl, $C_2$-$C_4$ alkoxyalkyl, $C_2$-$C_4$ alkylaminoalkyl, $C_3$-$C_4$ dialkylaminoalkyl, $C_1$-$C_3$ alkoxy, $C_2$-$C_4$ alkylcarbonyl or $C_2$-$C_4$ alkoxycarbonyl;
- $R^4$ is halogen, —OR$^7$ or —SC≡N;
- $R^5$ is H or $C_1$-$C_4$ alkyl;
- $R^7$ is H, $C_1$-$C_6$ alkyl, $C_1$-$C_6$ haloalkyl, $C_2$-$C_6$ alkenyl, $C_3$-$C_6$ alkynyl, $C_3$-$C_6$ cycloalkyl, $C_2$-$C_6$ cyanoalkyl, $C_2$-$C_6$ alkoxyalkyl, —CH(=O), —S(=O)$_2$OM$^1$ or —C(=W)R$^9$;
- $R^9$ is $C_1$-$C_6$ alkyl, $C_2$-$C_6$ alkoxyalkyl, $C_2$-$C_6$ alkylaminoalkyl, $C_3$-$C_6$ dialkylaminoalkyl, $C_2$-$C_6$ alkylthioalkyl, $C_1$-$C_6$ alkoxy or $C_1$-$C_6$ alkylthio;
- each U is independently O, S(=O)$_n$, N(R$^{10}$) or a direct bond;
- each V is independently $C_1$-$C_6$ alkylene, $C_2$-$C_6$ alkenylene, $C_3$-$C_6$ alkynylene, $C_3$-$C_6$ cycloalkylene or $C_3$-$C_6$ cycloalkenylene, wherein up to 3 carbon atoms are independently selected from C(=O), each optionally substituted with up to 5 substituents independently selected from halogen, cyano, nitro, hydroxy, $C_1$-$C_6$ alkyl, $C_1$-$C_6$ haloalkyl, $C_1$-$C_6$ alkoxy and $C_1$-$C_6$ haloalkoxy;
- each T is independently cyano, N(R$^{11a}$)(R$^{11b}$), OR$^{12}$ or S(=O)$_n$R$^{12}$;
- each R$^{10}$ is independently H, $C_1$-$C_6$ alkyl, $C_1$-$C_6$ haloalkyl, $C_2$-$C_6$ alkylcarbonyl, $C_2$-$C_6$ alkoxycarbonyl, $C_2$-$C_6$ (alkylthio)carbonyl, $C_2$-$C_6$ alkoxy(thiocarbonyl), $C_4$-$C_8$ cycloalkylcarbonyl, $C_4$-$C_8$ cycloalkoxycarbonyl, $C_4$-$C_8$ (cycloalkylthio)carbonyl or $C_4$-$C_8$ cycloalkoxy(thiocarbonyl);
- each R$^{11a}$ and R$^{11b}$ is independently H, $C_1$-$C_6$ alkyl, $C_1$-$C_6$ haloalkyl, $C_2$-$C_6$ alkenyl, $C_3$-$C_6$ alkynyl, $C_3$-$C_6$ cycloalkyl, $C_3$-$C_6$ halocycloalkyl, $C_2$-$C_6$ alkylcarbonyl, $C_2$-$C_6$ alkoxycarbonyl, $C_2$-$C_6$ (alkylthio)carbonyl, $C_2$-$C_6$ alkoxy(thiocarbonyl), $C_4$-$C_8$ cycloalkylcarbonyl, $C_4$-$C_8$ cycloalkoxycarbonyl, $C_4$-$C_8$ (cycloalkylthio)carbonyl or $C_4$-$C_8$ cycloalkoxy(thiocarbonyl); or
- a pair of R$^{11a}$ and R$^{11b}$ are taken together with the nitrogen atom to which they are attached to form a form a 3- to 6-membered heterocyclic ring, the ring optionally substituted with up to 5 substituents independently selected from R$^{13}$;
- each R$^{12}$ is independently H, $C_1$-$C_6$ alkyl, $C_1$-$C_6$ haloalkyl, $C_2$-$C_6$ alkenyl, $C_3$-$C_6$ alkynyl, $C_3$-$C_6$ cycloalkyl, $C_3$-$C_6$ halocycloalkyl, $C_2$-$C_6$ alkylcarbonyl, $C_2$-$C_6$ alkoxycarbonyl, $C_2$-$C_6$ (alkylthio)carbonyl, $C_2$-$C_6$ alkoxy(thiocarbonyl), $C_4$-$C_8$ cycloalkylcarbonyl, $C_4$-$C_8$ cycloalkoxycarbonyl, $C_4$-$C_8$ (cycloalkylthio)carbonyl or $C_4$-$C_8$ cycloalkoxy(thiocarbonyl);
- each R$^{13}$ is independently halogen, $C_1$-$C_6$ alkyl, $C_1$-$C_6$ haloalkyl or $C_1$-$C_6$ alkoxy;
- W is O or S;
- M$^1$ is K, Na or Li; and
- each n is independently 0, 1 or 2;
- provided that when $Q^2$ is a phenyl ring which is not substituted with $R^{3a}$ at either ortho position, then $Q^1$ is substituted by at least one $R^{3a}$ at an ortho position.

This invention is also directed to compounds of Formula 1A (including all stereoisomers), N-oxides, and salts thereof, agricultural compositions containing them and their use as fungicides:

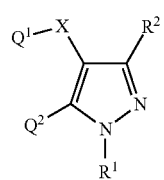

wherein
- $Q^1$ is a phenyl ring substituted with 1 to 5 substituents independently selected from $R^{3a}$;
- $Q^2$ is a phenyl ring substituted with 1 to 5 substituents independently selected from $R^{3a}$; or a 5- to 6-membered fully unsaturated heterocyclic ring, each ring containing ring members selected from carbon atoms and 1 to 3 heteroatoms independently selected from up to 2 O, up to 2 S and up to 3 N atoms, wherein up to 2 carbon ring members are independently selected from C(=O) and C(=S), each ring optionally substituted with up to 5 substituents independently selected from $R^{3a}$ on carbon atom ring members and $R^{3b}$ on nitrogen atom ring members;
- X is O, S(O)$_m$, N(R$^6$) or C(=O);
- $R^1$ is $C_1$-$C_2$ alkyl, halomethyl, cyanomethyl or cyclopropyl;
- $R^2$ is H, halogen, cyano, $C_1$-$C_2$ alkyl, $C_2$-$C_4$ alkenyl, $C_2$-$C_4$ alkynyl, $C_1$-$C_2$ haloalkyl, $C_2$-$C_3$ cyanoalkyl, $C_1$-$C_2$ hydroxyalkyl, cyclopropyl, halocyclopropyl, $C_2$-$C_3$ alkoxyalkyl, $C_1$-$C_2$ alkylthio, $C_1$-$C_2$ alkoxy or $C_1$-$C_2$ haloalkoxy;
- each $R^{3a}$ is independently halogen, cyano, hydroxy, nitro, amino, $C_1$-$C_3$ alkyl, $C_2$-$C_4$ alkenyl, $C_2$-$C_4$ alkynyl, $C_1$-$C_3$ haloalkyl, $C_3$-$C_6$ cycloalkyl, $C_3$-$C_6$ halocycloalkyl, $C_4$-$C_6$ alkylcycloalkyl, $C_4$-$C_6$ cycloalkylalkyl, $C_1$-$C_3$ alkylthio, $C_1$-$C_3$ haloalkylthio, $C_1$-$C_3$ alkylsulfinyl, $C_1$-$C_3$ haloalkylsulfinyl, $C_1$-$C_3$ alkylsulfonyl, $C_1$-$C_3$ haloalkylsulfonyl, $C_1$-$C_3$ alkoxy, $C_1$-$C_3$ haloalkoxy, $C_3$-$C_6$ cycloalkoxy, $C_1$-$C_3$ alkylsulfonyloxy, $C_1$-$C_3$ haloalkylsulfonyloxy, $C_2$-$C_4$ alkylcarbonyloxy, $C_2$-$C_4$ alkylcarbonyl, $C_1$-$C_3$ alkylamino, $C_2$-$C_4$ dialkylamino, $C_2$-$C_4$ alkylcarbonylamino, —CH(=O), —NHCH(=O), —SF$_5$, —SC≡N or —U—V-T;
- each $R^{3b}$ is independently cyano, $C_1$-$C_3$ alkyl, $C_2$-$C_4$ alkenyl, $C_2$-$C_4$ alkynyl, $C_3$-$C_6$ cycloalkyl, $C_2$-$C_4$ alkoxyalkyl, $C_2$-$C_4$ alkylaminoalkyl, $C_3$-$C_4$ dialkylaminoalkyl, $C_1$-$C_3$ alkoxy, $C_2$-$C_4$ alkylcarbonyl or $C_2$-$C_4$ alkoxycarbonyl;
- $R^6$ is H, hydroxy, $C_1$-$C_6$ alkyl, $C_1$-$C_6$ haloalkyl, $C_2$-$C_6$ alkenyl, $C_2$-$C_6$ alkynyl, $C_3$-$C_6$ cycloalkyl, $C_2$-$C_6$ alkoxyalkyl, $C_2$-$C_6$ cyanoalkyl, NH$_2$, —CH(=O), —OR$^7$, —OS(=O)$_2$M$^1$, —S(=O)$_n$R$^8$ or —C(=W)R$^9$;
- $R^7$ is $C_1$-$C_6$ alkyl, $C_1$-$C_6$ haloalkyl, $C_2$-$C_6$ alkenyl, $C_3$-$C_6$ alkynyl, $C_3$-$C_6$ cycloalkyl, $C_2$-$C_6$ cyanoalkyl, $C_2$-$C_6$ alkoxyalkyl, —CH(=O), —S(=O)$_2$OM$^1$ or —C(=W)R$^9$;
- $R^8$ is $C_1$-$C_6$ alkyl or $C_1$-$C_6$ haloalkyl;
- $R^9$ is $C_1$-$C_6$ alkyl, $C_2$-$C_6$ alkoxyalkyl, $C_2$-$C_6$ alkylaminoalkyl, $C_3$-$C_6$ dialkylaminoalkyl, $C_2$-$C_6$ alkylthioalkyl, $C_1$-$C_6$ alkoxy or $C_1$-$C_6$ alkylthio;
- each U is independently O, S(=O)$_n$, N(R$^{10}$) or a direct bond;
- each V is independently $C_1$-$C_6$ alkylene, $C_2$-$C_6$ alkenylene, $C_3$-$C_6$ alkynylene, $C_3$-$C_6$ cycloalkylene or $C_3$-$C_6$ cycloalkenylene, wherein up to 3 carbon atoms are independently selected from C(=O), each optionally substituted with up to 5 substituents independently selected from halogen, cyano, nitro, hydroxy, $C_1$-$C_6$ alkyl, $C_1$-$C_6$ haloalkyl, $C_1$-$C_6$ alkoxy and $C_1$-$C_6$ haloalkoxy;
- each T is independently cyano, N(R$^{11a}$)(R$^{11b}$), OR$^{12}$ or S(=O)$_n$R$^{12}$;
- each $R^{10}$ is independently H, $C_1$-$C_6$ alkyl, $C_1$-$C_6$ haloalkyl, $C_2$-$C_6$ alkylcarbonyl, $C_2$-$C_6$ alkoxycarbonyl, $C_2$-$C_6$ (alkylthio)carbonyl, $C_2$-$C_6$ alkoxy(thiocarbonyl), $C_4$-$C_8$ cycloalkylcarbonyl, $C_4$-$C_8$ cycloalkoxycarbonyl, $C_4$-$C_8$ (cycloalkylthio)carbonyl or $C_4$-$C_8$ cycloalkoxy(thiocarbonyl);
- each $R^{11a}$ and $R^{11b}$ is independently H, $C_1$-$C_6$ alkyl, $C_1$-$C_6$ haloalkyl, $C_2$-$C_6$ alkenyl, $C_3$-$C_6$ alkynyl, $C_3$-$C_6$ cycloalkyl, $C_3$-$C_6$ halocycloalkyl, $C_2$-$C_6$ alkylcarbonyl, $C_2$-$C_6$ alkoxycarbonyl, $C_2$-$C_6$ (alkylthio)carbonyl, $C_2$-$C_6$ alkoxy(thiocarbonyl), $C_4$-$C_8$ cycloalkylcarbonyl, $C_4$-$C_8$ cycloalkoxycarbonyl, $C_4$-$C_8$ (cycloalkylthio)carbonyl or $C_4$-$C_8$ cycloalkoxy(thiocarbonyl); or
- a pair of $R^{11a}$ and $R^{11b}$ are taken together with the nitrogen atom to which they are attached to form a form a 3- to 6-membered heterocyclic ring, the ring optionally substituted with up to 5 substituents independently selected from $R^{13}$;
- each $R^{12}$ is independently H, $C_1$-$C_6$ alkyl, $C_1$-$C_6$ haloalkyl, $C_2$-$C_6$ alkenyl, $C_3$-$C_6$ alkynyl, $C_3$-$C_6$ cycloalkyl, $C_3$-$C_6$ halocycloalkyl, $C_2$-$C_6$ alkylcarbonyl, $C_2$-$C_6$ alkoxycarbonyl, $C_2$-$C_6$ (alkylthio)carbonyl, $C_2$-$C_6$ alkoxy(thiocarbonyl), $C_4$-$C_8$ cycloalkylcarbonyl, $C_4$-$C_8$ cycloalkoxycarbonyl, $C_4$-$C_8$ (cycloalkylthio)carbonyl or $C_4$-$C_8$ cycloalkoxy(thiocarbonyl);
- each $R^{13}$ is independently halogen, $C_1$-$C_6$ alkyl, $C_1$-$C_6$ haloalkyl or $C_1$-$C_6$ alkoxy;
- W is O or S;
- $M^1$ is K, Na or Li;
- m is 0, 1 or 2; and
- each n is independently 0, 1 or 2;
- provided that:
  - (a) when $Q^2$ is a phenyl ring which is not substituted with $R^{3a}$ at either ortho position, then $Q^1$ is substituted by at least one $R^{3a}$ at an ortho position; and
  - (b) the compound is other than 1-[2-[4-(2,4-dichlorobenzoyl)-1,3-dimethyl-1H-pyrazol-5-yl]phenyl]ethanone.

More particularly, this invention pertains to a compound selected from compounds of Formula 1 (including all stereoisomers), an N-oxide or a salt thereof; or a compound selected from compounds of Formula 1A (including all stereoisomers), an N-oxide or a salt thereof.

This invention also relates to a fungicidal composition comprising (a) a compound of the invention (i.e. in a fungicidally effective amount); and (b) at least one additional component selected from the group consisting of surfactants, solid diluents and liquid diluents.

This invention also relates to a fungicidal composition comprising (a) a compound of the invention; and (b) at least one other fungicide (e.g., at least one other fungicide having a different site of action).

This invention further relates to a method for controlling plant diseases caused by fungal plant pathogens comprising applying to the plant or portion thereof, or to the plant seed, a fungicidally effective amount of a compound of the invention (e.g., as a composition described herein).

DETAILS OF THE INVENTION

As used herein, the terms "comprises," "comprising," "includes," "including," "has," "having," "contains", "containing," "characterized by" or any other variation thereof, are intended to cover a non-exclusive inclusion, subject to any limitation explicitly indicated. For example, a composition, mixture, process, method, article, or apparatus that comprises a list of elements is not necessarily limited to only those elements but may include other elements not expressly listed or inherent to such composition, mixture, process, method, article, or apparatus.

The transitional phrase "consisting of" excludes any element, step, or ingredient not specified. If in the claim, such would close the claim to the inclusion of materials other than those recited except for impurities ordinarily associated therewith. When the phrase "consisting of" appears in a clause of the body of a claim, rather than immediately following the preamble, it limits only the element set forth in that clause; other elements are not excluded from the claim as a whole.

The transitional phrase "consisting essentially of" is used to define a composition, method or apparatus that includes materials, steps, features, components, or elements, in addition to those literally disclosed, provided that these additional materials, steps, features, components, or elements do not materially affect the basic and novel characteristic(s) of the claimed invention. The term "consisting essentially of" occupies a middle ground between "comprising" and "consisting of".

Where applicants have defined an invention or a portion thereof with an open-ended term such as "comprising," it should be readily understood that (unless otherwise stated) the description should be interpreted to also describe such an invention using the terms "consisting essentially of" or "consisting of:"

Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, the indefinite articles "a" and "an" preceding an element or component of the invention are intended to be nonrestrictive regarding the number of instances (i.e. occurrences) of the element or component. Therefore "a" or "an" should be read to include one or at least one, and the singular word form of the element or component also includes the plural unless the number is obviously meant to be singular.

As referred to in the present disclosure and claims, "plant" includes members of Kingdom Plantae, particularly seed plants (Spermatopsida), at all life stages, including young plants (e.g., germinating seeds developing into seedlings) and mature, reproductive stages (e.g., plants producing flowers and seeds). Portions of plants include geotropic members typically growing beneath the surface of the growing medium (e.g., soil), such as roots, tubers, bulbs and corms, and also members growing above the growing medium, such as foliage (including stems and leaves), flowers, fruits and seeds.

As referred to herein, the term "seedling", used either alone or in a combination of words means a young plant developing from the embryo of a seed.

As referred to herein, the term "broadleaf" used either alone or in words such as "broadleaf crop" means dicot or dicotyledon, a term used to describe a group of angiosperms characterized by embryos having two cotyledons.

As used herein, the term "alkylating agent" refers to a chemical compound in which a carbon-containing radical is bound through a carbon atom to a leaving group such as halide or sulfonate, which is displaceable by bonding of a nucleophile to said carbon atom. Unless otherwise indicated, the term "alkylating agent" does not limit the carbon-containing radical to alkyl; the carbon-containing radicals in alkylating agents include the variety of carbon-bound substituent radicals specified, for example, for $R^1$ and $Q^1$.

In the above recitations, the term "alkyl", used either alone or in compound words such as "alkylthio" or "haloalkyl" includes straight-chain or branched alkyl such as methyl, ethyl, n-propyl, i-propyl, or the different butyl, pentyl or hexyl isomers. "Alkenyl" includes straight-chain or branched alkenes such as ethenyl, 1-propenyl, 2-propenyl, and the different butenyl, pentenyl and hexenyl isomers. "Alkenyl" also includes polyenes such as 1,2-propadienyl and 2,4-hexadienyl. "Alkynyl" includes straight-chain or branched alkynes such as ethynyl, 1-propynyl, 2-propynyl and the different butynyl, pentynyl and hexynyl isomers. "Alkynyl" can also include moieties comprised of multiple triple bonds such as 2,5-hexadiynyl. "Alkylene" denotes a straight-chain or branched alkanediyl. Examples of "alkylene" include $CH_2$, $CH_2CH_2$, $CH(CH_3)$, $CH_2CH_2CH_2$, $CH_2CH(CH_3)$, and the different butylene, pentylene or hexylene isomers. "Alkenylene" denotes a straight-chain or branched alkenediyl containing one olefinic bond. Examples of "alkenylene" include $CH=CH$, $CH_2CH=CH$ and $CH=C(CH_3)$. "Alkynylene" denotes a straight-chain or branched alkynediyl containing one triple bond. Examples of "alkynylene" include $CH_2C\equiv C$, $C\equiv CCH_2$, and the different butynylene, pentynylene or hexynylene isomers.

The term "cycloalkyl" denotes a saturated carbocyclic ring consisting of 3 to 7 carbon atoms linked to one another by single bonds. Examples of "cycloalkyl" include cyclopropyl, cyclobutyl, cyclopentyl and cyclohexyl. The term "alkylcycloalkyl" denotes alkyl substitution on a cycloalkyl moiety and includes, for example, ethylcyclopropyl, i-propylcyclopropyl and methylcyclopentyl. The term "cycloalkylalkyl" denotes cycloalkyl substitution on an alkyl moiety. Examples of "cycloalkylalkyl" include cyclopropylmethyl, cyclopentylethyl, and other cycloalkyl moieties bonded to straight-chain or branched alkyl groups. The term "cycloalkylcycloalkyl" denotes cycloalkyl substitution on another cycloalkyl ring, wherein each cycloalkyl ring independently has from 3 to 7 carbon atom ring members. Examples of cycloalkylcycloalkyl include cyclopropylcyclopropyl (such as 1,1'-bicyclopropyl-1-yl, 1,1'-bicyclopropyl-2-yl), cyclohexylcyclopentyl (such as 4-cyclopentylcyclohexyl) and cyclohexylcyclohexyl (such as 1,1'-bicyclohexyl-1-yl), and the different cis- and trans-cycloalkylcycloalkyl isomers, (such as (1R,2S)-1,1'-bicyclopropyl-2-yl and (1R,2R)-1,1'-bicyclopropyl-2-yl). The term "cycloalkoxy" denotes cycloalkyl attached to and linked through an oxygen atom including, for example, cyclopentyloxy and cyclohexyloxy. "Cycloalkylcarbonyl" denotes cycloalkyl bonded to a $C(=O)$ group including, for example, cyclopropylcarbonyl and cyclopentylcarbonyl. The term "cycloalkoxycarbonyl" means cycloalkoxy bonded to a $C(=O)$ group, for example, cyclopropyloxycarbonyl and cyclopentyloxycarbonyl. The term "cycloalkylene" denotes a cycloalkanediyl ring. Examples of "cycloalkylene" include cyclopropylene, cyclobutylene, cyclopentylene and cyclohexylene. The term "cycloalkenylene" denotes a cycloalkenediyl ring containing one olefinic bond. Examples of "cycloalkenylene" include cyclopropylene, cyclobutylene and cyclopentylene.

"Alkoxy" includes, for example, methoxy, ethoxy, n-propyloxy, i-propyloxy and the different butoxy, pentoxy and hexyloxy isomers. "Alkylamino" includes an NH radical substituted with straight-chain or branched alkyl. Examples of "alkylamino" include $CH_3CH_2NH$, $CH_3CH_2CH_2NH$ and $(CH_3)_2CHCH_2NH$. "Alkylthio" includes branched or straight-chain alkylthio moieties such as methylthio, ethylthio, and the different propylthio, butylthio, pentylthio and hexylthio isomers. "Alkylsulfinyl" includes both enantiomers of an alkylsulfinyl group. Examples of "alkylsulfinyl" include $CH_3S(=O)$, $CH_3CH_2S(=O)$, $CH_3CH_2CH_2S(=O)$, $(CH_3)_2CHS(=O)$, and the different ethylsulfinyl or propylsulfinyl isomers. Examples of "alkylsulfonyl" include $CH_3S(=O)_2$, $CH_3CH_2S(=O)_2$, $CH_3CH_2CH_2S(=O)_2$, $(CH_3)_2CHS(=O)_2$, and the different ethylsulfonyl or propylsulfonyl isomers. The term "alkylsulfonyloxy" denotes alkylsulfonyl attached to and linked through an oxygen atom. Examples of "alkylsulfonyloxy" include $CH_3S(=O)_2O$ and $CH_3CH_2S(=O)_2O$.

"Alkoxyalkyl" denotes alkoxy substitution on alkyl. Examples of "alkoxyalkyl" include $CH_3OCH_2$, $CH_3OCH_2CH_2$, $CH_3CH_2OCH_2$, $CH_3CH_2CH_2OCH_2$ and $CH_3CH_2OCH_2CH_2$. "Alkylthioalkyl" denotes alkylthio substitution on alkyl. Examples of "alkylthioalkyl" include $CH_3SCH_2$, $CH_3SCH_2CH_2$, $CH_3CH_2SCH_2$, $CH_3CH_2CH_2CH_2SCH_2$ and $CH_3CH_2SCH_2CH_2$. "Alkylaminoalkyl" denotes alkylamino substitution on alkyl. Examples of "alkylaminoalkyl" include $CH_3NHCH_2$, $CH_3NHCH_2CH_2$, $CH_3CH_2NHCH_2$, $CH_3CH_2CH_2NHCH_2$ and $CH_3CH_2NHCH_2CH_2$. Examples of "dialkylaminoalkyl" include $(CH_3CH)_2NCH_2$ and $CH_3CH_2(CH_3)NCH_2CH_2$.

"Cyanoalkyl" denotes an alkyl group substituted with one cyano group. Examples of "cyanoalkyl" include $NCCH_2$, (also referred to herein as "cyanomethyl") $NCCH_2CH_2$ and $CH_3CH(CN)CH_2$. "Hydroxyalkyl" denotes an alkyl group substituted with one hydroxy group. Examples of "hydroxyalkyl" include $HOCH_2$, (also referred to herein as "hydroxymethyl") and $HOCH_2CH_2$.

"Alkylcarbonyl" denotes a straight-chain or branched alkyl group bonded to a $C(=O)$ moiety. Examples of "alkylcarbonyl" include $CH_3C(=O)$, $CH_3CH_2CH_2C(=O)$ and $(CH_3)_2CHC(=O)$. Examples of "alkoxycarbonyl" include $CH_3C(=O)$, $CH_3CH_2OC(=O)$, $CH_3CH_2CH_2C(=O)$, $(CH_3)_2CHOC(=O)$ and the different pentoxy- or hexoxycarbonyl isomers. The term "alkylcarbonyloxy" denotes straight-chain or branched alkyl bonded to a $C(=O)O$ moiety. Examples of "alkylcarbonyloxy" include $CH_3CH_2C(=O)O$ and $(CH_3)_2CHC(=O)O$. "Alkoxy(thiocarbonyl)" denotes a straight-chain or branched alkoxy group bonded to a $C(=S)$ moiety. Examples of "alkoxy(thiocarbonyl)" include $CH_3C(=S)$, $CH_3CH_2CH_2C(=S)$ and $(CH_3)_2CHOC(=S)$. "(Alkylthio)carbonyl" denotes a straight-chain or branched alkylthio group bonded to a $C(=O)$ moiety. Examples of "(alkylthio)carbonyl" include $CH_3SC(=O)$, $CH_3CH_2CH_2SC(=O)$ and $(CH_3)_2CHSC(=O)$. The term "alkylcarbonylamino" denotes alkyl bonded to a $C(=O)NH$ moiety. Examples of "alkylcarbonylamino" include $CH_3CH_2C(=O)NH$ and $CH_3CH_2CH_2C(=O)NH$.

The term "halogen", either alone or in compound words such as "halomethyl", "haloalkyl", or when used in descriptions such as "alkyl substituted with halogen" includes fluorine, chlorine, bromine or iodine. Further, when used in compound words such as "halomethyl", "haloalkyl", or when used in descriptions such as "alkyl substituted with halogen" said methyl or alkyl may be partially or fully substituted with halogen atoms which may be the same or different. Examples of "haloalkyl" or "alkyl substituted with halogen" include $F_3C$, $ClCH_2$, $CF_3CH_2$ and $CF_3CCl_2$. The terms "haloalkoxy", "haloalkylthio", "haloalkylsulfinyl" "haloalkylsulfonyl" and "halocycloalkyl" are defined analogously to the term "haloalkyl". Examples of "haloalkoxy" include $CF_3O$, $CCl_3CH_2O$, $F_2CHCH_2CH_2O$ and $CF_3CH_2O$. Examples of "haloalkylthio" include $CF_3S$, $CCl_3S$ and $CF_3CH_2S$. Examples of "haloalkylsulfinyl" include $CF_3S(=O)$, $CCl_3S(=O)$, $CF_3CH_2S(=O)$ and $CF_3CF_2S(=O)$. Examples of "haloalkylsulfonyl" include $CF_3S(=O)_2$, $CCl_3S(=O)_2$, $CF_3CH_2S(=O)_2$ and $CF_3CF_2S(=O)_2$. Examples of "halocycloalkyl" include chlorocyclopropyl, fluorocyclobutyl and chlorocyclohexyl.

The total number of carbon atoms in a substituent group is indicated by the "$C_i$-$C_j$" prefix where i and j are numbers from 1 to 8. For example, $C_1$-$C_4$ alkylsulfonyl designates methylsulfonyl through butylsulfonyl; $C_2$ alkoxyalkyl designates $CH_3OCH_2$; $C_3$ alkoxyalkyl designates, for example, $CH_3OCH_2CH_2$ or $CH_3CH_2OCH_2$; and $C_4$ alkoxyalkyl designates the various isomers of an alkyl group substituted with an alkoxy group containing a total of four carbon atoms, examples including $CH_3CH_2CH_2OCH_2$ and $CH_3CH_2OCH_2CH_2$.

The term "unsubstituted" in connection with a group such as a ring means the group does not have any substituents other than its one or more attachments to the remainder of Formula 1 or Formula 1A. The term "optionally substituted" means that the number of substituents can be zero. Unless otherwise indicated, optionally substituted groups may be substituted with as many optional substituents as can be accommodated by replacing a hydrogen atom with a non-hydrogen substituent on any available carbon or nitrogen atom. Commonly, the number of optional substituents (when present) range from 1 to 3. As used herein, the term "optionally substituted" is used interchangeably with the phrase "substituted or unsubstituted" or with the term "(un)substituted."

The number of optional substituents may be restricted by an expressed limitation. For example, the phrase "optionally substituted with up to 3 substituents independently selected from $R^{3a}$ on carbon atom ring members" means that 0, 1, 2 or 3 substituents can be present (if the number of potential connection points allows). Similarly, the phrase "optionally substituted with up to 5 substituents independently selected from $R^{3a}$ on carbon atom ring members" means that 0, 1, 2, 3, 4 or 5 substituents can be present if the number of available connection points allows. When a range specified for the number of substituents (e.g., r being an integer from 0 to 4 in Exhibit 1) exceeds the number of positions available for substituents on a ring (e.g., only 2 positions are available for $(R^v)_r$ on A-11 in Exhibit 1), the actual higher end of the range is recognized to be the number of available positions.

When a compound is substituted with a substituent bearing a subscript that indicates the number of said substituents can exceed 1, said substituents (when they exceed 1) are independently selected from the group of defined substituents (e.g., $(R^v)_r$ wherein r is 1, 2, 3 or 4 in Exhibit 1). When a variable group is shown to be optionally attached, for example $(R^v)_r$ wherein r may be 0, then hydrogen may be at the position even if not recited in the variable group definition. When one or more positions on a group are said to be "not substituted" or "unsubstituted", then hydrogen atoms are attached to take up any free valency.

Unless otherwise indicated, a "ring" as a component of Formula 1 or Formula 1A (e.g., $Q^2$) is carbocyclic (e.g., phenyl) or heterocyclic (e.g., pyridinyl). The term "ring member" refers to an atom (e.g., C, O, N or S) or other moiety (e.g., $C(=O)$ or $C(=S)$) forming the backbone of a ring.

The term "nonaromatic" includes rings that are fully saturated as well as partially or fully unsaturated, provided that none of the rings are aromatic. The term "aromatic" indicates that each of the ring atoms of a fully unsaturated ring is essentially in the same plane and has a p-orbital perpendicular to the ring plane, and that (4n+2) π electrons, where n is a positive integer, are associated with the ring to comply with Hückel's rule. The term "fully unsaturated heterocyclic ring" includes both aromatic and nonaromatic fully unsaturated heterocycles.

The terms "carbocyclic ring" or "carbocycle" denote a ring wherein the atoms forming the ring backbone are selected only from carbon. When a fully unsaturated carbocyclic ring satisfies Hückel's rule, then said ring is also called an "aromatic carbocyclic ring". The term "saturated carbocyclic ring" refers to a ring having a backbone consisting of carbon atoms linked to one another by single bonds; unless otherwise specified, the remaining carbon valences are occupied by hydrogen atoms.

The terms "heterocyclic ring" or "heterocycle" denote rings in which at least one atom forming the ring backbone is not carbon (e.g., N, O or S). Typically a heterocyclic ring contains no more than 3 N atoms, no more than 2 O atoms and no more than 2S atoms. Unless otherwise indicated, a heterocyclic ring can be a saturated, partially unsaturated or fully unsaturated ring. When a fully unsaturated heterocyclic ring satisfies Hückel's rule, then said ring is also called a "heteroaromatic ring" or "aromatic heterocyclic ring". Unless otherwise indicated, heterocyclic rings can be attached through any available carbon or nitrogen by replacement of a hydrogen on said carbon or nitrogen.

In the context of the present invention, when an instance of $Q^1$ or $Q^2$ comprises a phenyl or a 6-membered fully unsaturated heterocyclic ring, the ortho, meta and para positions of each ring is relative to the connection of the ring to the remainder of Formula 1.

As noted above, $Q^1$ and $Q^2$ can be, inter alia, phenyl optionally substituted with 1 to 5 substituents independently selected from $R^{3a}$. In the circumstances when an instance of $Q^1$ or $Q^2$ comprises a phenyl ring substituted with 4 or less substituents independently selected from $R^{3a}$, then hydrogen atoms are attached to take up any free valency.

As noted above, $Q^2$ attached to Formula 1 or Formula 1A is, inter alia, a 5- to 6-membered fully unsaturated heterocyclic ring, each ring containing ring members selected from carbon atoms and up to 3 heteroatoms independently selected from up to 2 O, up to 2 S and up to 3 N atoms, wherein up to 2 carbon atom ring members are independently selected from C(=O) and C(=S), each ring optionally substituted with up to 5 substituents independently selected from any substituent as defined in the Summary of the Invention for $Q^2$ (i.e. $R^{3a}$ on carbon atom ring members and $R^{3b}$ on nitrogen atom ring members). As the substituents are optional, 0 to 5 substituents may be present, limited only by the number of available points of attachment. In this definition the ring members selected from up to 2 O, up to 2 S and up to 3 N atoms are optional, provided at least one ring member is not carbon (e.g., N, O or S). The nitrogen atom ring members may be oxidized as N-oxides, because compounds relating to Formula 1 or Formula 1A also include N-oxide derivatives. The up to 2 carbon atom ring members selected from C(=O) and C(=S) are in addition to the up to 3 heteroatoms selected from up to 2 O, up to 2 S and up to 3 N atoms. Examples of a 5- to 6-membered fully unsaturated heterocyclic ring include the rings A-1 through A-31 illustrated in Exhibit 1. The variable $R^v$, in Exhibit 1, is any substituent as defined in the Summary of the Invention for $Q^2$ (i.e. $R^{3a}$ on carbon atom ring members and $R^{3b}$ on nitrogen atom ring members) and r is an integer from 0 to 4, limited by the number of available positions on each depicted ring.

Although $R^v$ groups are shown in the structures A-1 through A-31, it is noted that they do not need to be present since they are optional substituents. The nitrogen atoms that require substitution to fill their valence are substituted with H or $R^v$. Note that when the attachment point between $(R^v)_r$ and the depicted ring is illustrated as floating, $(R^v)_r$ can be attached to any available carbon or nitrogen atom of the depicted ring. Note that when the attachment point of the depicted ring to the remainder of Formula 1 or 1A is illustrated as floating, the ring can be attached to the remainder of Formula 1 or 1A through any available carbon or nitrogen of the depicted ring by replacement of a hydrogen atom.

Exhibit 1

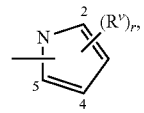

A-1

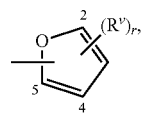

A-2

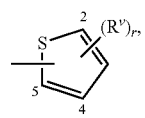

A-3

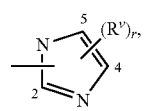

A-4

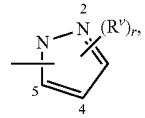

A-5

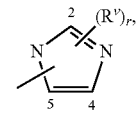

A-6

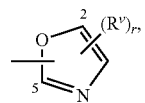

A-7

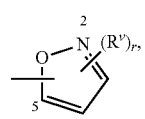

A-8

-continued
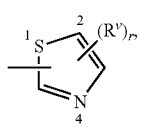 A-9
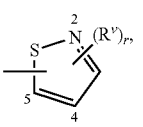 A-10
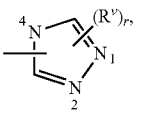 A-11
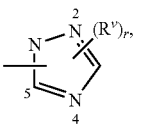 A-12
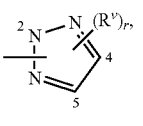 A-13
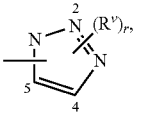 A-14
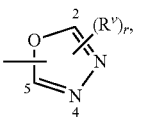 A-15
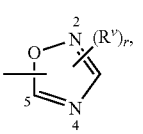 A-16
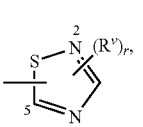 A-17
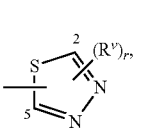 A-18
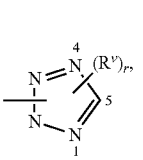 A-19
-continued
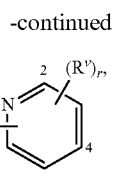 A-20
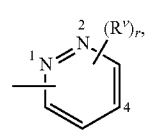 A-21
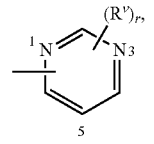 A-22
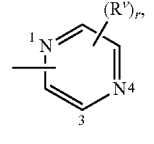 A-23
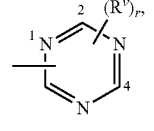 A-24
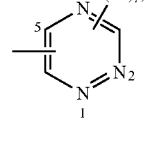 A-25
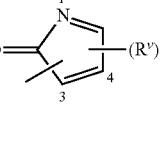 A-26
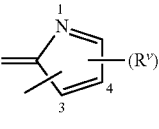 A-27
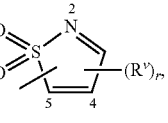 A-28
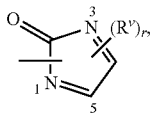 A-29
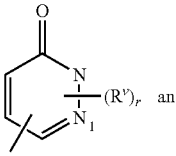 and A-30

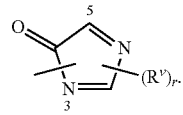

A-31

A wide variety of synthetic methods are known in the art to enable preparation of aromatic heterocyclic rings; for extensive reviews see the eight volume set of *Comprehensive Heterocyclic Chemistry*, A. R. Katritzky and C. W. Rees editors-in-chief, Pergamon Press, Oxford, 1984 and the twelve volume set of *Comprehensive Heterocyclic Chemistry II*, A. R. Katritzky, C. W. Rees and E. F. V. Scriven editors-in-chief, Pergamon Press, Oxford, 1996.

Compounds of this invention can exist as one or more stereoisomers. The various stereoisomers include enantiomers, diastereomers, atropisomers and geometric isomers. One skilled in the art will appreciate that one stereoisomer may be more active and/or may exhibit beneficial effects when enriched relative to the other stereoisomer(s) or when separated from the other stereoisomer(s). Additionally, the skilled artisan knows how to separate, enrich, and/or to selectively prepare said stereoisomers. The compounds of the invention may be present as a mixture of stereoisomers, individual stereoisomers or as an optically active form. Of note are atropisomers, which are stereoisomeric conformations of a molecule that occur when rotation about a single bond is restricted such that interconversion is slow enough to allow separation. Restricted rotation of one or more bonds is a result of steric interaction with other parts of the molecule. In the present invention, compounds of Formula 1 and Formula 1A can exhibit atropisomerism when the energy barrier to free rotation around a single unsymmetrical bond is sufficiently high that separation of isomers is possible. Atropisomerism is defined to exist where the isomers have a half-life of at least 1000 seconds, which is a free energy barrier of at least about 22.3 kcal mol$^{-1}$ at about 20° C. (Oki, *Topics in Stereochemistry*, Vol. 14, John Wiley & Sons, Inc., 1983). One skilled in the art will appreciate that one atropisomer may be more active and/or may exhibit beneficial effects when enriched relative to the other atropisomer or when separated from the other atropisomer. Additionally, the skilled artisan knows how to separate, enrich, and/or to selectively prepare said atropisomers. Further description of atropisomers can be found in March, *Advanced Organic Chemistry*, 101-102, 4$^{th}$ Ed. 1992; Oki, *Topics in Stereochemistry*, Vol. 14, John Wiley & Sons, Inc., 1983 and Gawronski et al, *Chirality* 2002, 14, 689-702. This invention includes compounds that are enriched compared to the racemic mixture in an atropisomer of Formula 1 or Formula 1A. Also included are the essentially pure atropisomers of compounds of Formula 1 or Formula 1A.

Also of note are enantiomers of Formula 1 and Formula 1A. For example, two possible enantiomers of Formula 1 are depicted below as Formula 1' and Formula 1" wherein the chiral center is identified with an asterisk (*) and the substituents R$^4$ and R$^5$ are not identical.

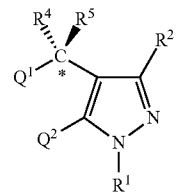

1'

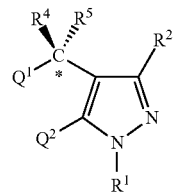

1"

Molecular depictions drawn herein follow standard conventions for depicting stereochemistry. To indicate stereoconfiguration, bonds rising from the plane of the drawing and towards the viewer are denoted by solid wedges wherein the broad end of the wedge is attached to the atom rising from the plane of the drawing towards the viewer. Bonds going below the plane of the drawing and away from the viewer are denoted by dashed wedges wherein the narrow end of the wedge is attached to the atom further away from the viewer. Constant width lines indicate bonds with a direction opposite or neutral relative to bonds shown with solid or dashed wedges; constant width lines also depict bonds in molecules or parts of molecules in which no particular stereoconfiguration is intended to be specified.

This invention comprises racemic mixtures, for example, equal amounts of the enantiomers of Formulae 1' and 1". In addition, this invention includes compounds that are enriched compared to the racemic mixture in an enantiomer of Formula 1 or 1A. Also included are the essentially pure enantiomers of compounds of Formula 1 or 1A, for example, Formula 1' and Formula 1".

When enantiomerically enriched, one enantiomer is present in greater amounts than the other, and the extent of enrichment can be defined by an expression of enantiomeric excess ("ee"), which is defined as (2x−1)·100%, where x is the mole fraction of the dominant enantiomer in the mixture (e.g., an ee of 20% corresponds to a 60:40 ratio of enantiomers).

Of note are compositions of this invention having at least a 50%, or at least a 75%, or at least a 90%, or at least a 94% enantiomeric excess of an isomer. Of particular note are enantiomerically pure embodiments.

Compounds of Formula 1 or Formula 1A can comprise additional chiral centers. For example, substituents such as R$^{3a}$ may themselves contain chiral centers.

One skilled in the art recognizes that because in the environment and under physiological conditions salts of chemical compounds are in equilibrium with their corresponding nonsalt forms, salts share the biological utility of the nonsalt forms. Thus a wide variety of salts of the compounds of Formula 1 and Formula 1A are useful for control of plant diseases caused by fungal plant pathogens (i.e. are agriculturally suitable). The salts of the compounds of Formula 1 and Formula 1A include acid-addition salts with inorganic or organic acids such as hydrobromic, hydrochloric, nitric, phosphoric, sulfuric, acetic, butyric, fumaric, lactic, maleic, malonic, oxalic, propionic, salicylic, tartaric, 4-toluenesulfonic or valeric acids.

Compounds selected from Formula 1 or Formula 1A, stereoisomers, N-oxides, and salts thereof, typically exist in more than one form, therefore Formula 1 and Formula 1A includes all crystalline and non-crystalline forms of the compounds that Formula 1 and Formula 1A represents. Non-crystalline forms include embodiments which are solids such as waxes and gums as well as embodiments which are liquids such as solutions and melts. Crystalline forms include embodiments which represent essentially a single crystal type and embodiments which represent a mixture of polymorphs (i.e. different crystalline types). The term "polymorph" refers to a particular crystalline form of a chemical compound that can crystallize in different crystalline forms, these forms having different arrangements and/or conformations of the molecules in the crystal lattice. Although polymorphs can have the same chemical composition, they can also differ in composition due the presence or absence of co-crystallized water or other molecules, which can be weakly or strongly bound in the lattice. Polymorphs can differ in such chemical, physical and biological properties as crystal shape, density, hardness, color, chemical stability, melting point, hygroscopicity, suspensibility, dissolution rate and biological availability. One skilled in the art will appreciate that a polymorph of a compound represented by Formula 1 or Formula 1A can exhibit beneficial effects (e.g., suitability for preparation of useful formulations, improved biological performance) relative to another polymorph or a mixture of polymorphs of the same compound represented by Formula 1 or Formula 1A. Preparation and isolation of a particular polymorph of a compound represented by Formula 1 or Formula 1A can be achieved by methods known to those skilled in the art including, for example, crystallization using selected solvents and temperatures.

Embodiments of the present invention as described in the Summary of the Invention include those described below. In the following Embodiments, Formula 1 includes stereoisomers, N-oxides and salts thereof, and reference to "a compound of Formula 1" includes the definitions of substituents specified in the Summary of the Invention unless further defined in the Embodiments.

Embodiment 1

A compound of Formula 1 wherein $Q^1$ is a phenyl ring substituted with 1 to 3 substituents independently selected from $R^{3a}$.

Embodiment 2

A compound of Embodiment 1 wherein $Q^1$ is a phenyl ring substituted with 2 to 3 substituents independently selected from $R^{3a}$.

Embodiment 3

A compound of Embodiment 1 wherein $Q^1$ is a phenyl ring substituted with 1 substituent independently selected from $R^{3a}$.

Embodiment 4

A compound of Embodiment 1 wherein $Q^1$ is a phenyl ring substituted with 2 substituents independently selected from $R^{3a}$.

Embodiment 5

A compound of Embodiment 1 wherein $Q^1$ is a phenyl ring substituted with 3 substituents selected from $R^{3a}$.

Embodiment 6

A compound of Formula 1 or any one of Embodiments 1 through 5 wherein $Q^1$ is a phenyl ring substituted with at least one $R^{3a}$ substituent attached at an ortho position (relative to the connection of the $Q^1$ ring to the remainder of Formula 1).

Embodiment 6a

A compound of Formula 1 or any one of Embodiments 1 through 6 wherein $Q^1$ is a phenyl ring substituted with two $R^{3a}$ substituents attached at an ortho position and the para position (relative to the connection of the $Q^1$ ring to the remainder of Formula 1).

Embodiment 6b

A compound of Formula 1 or any one of Embodiments 1 through 6 wherein $Q^1$ is a phenyl ring substituted with two $R^{3a}$ substituents attached at both ortho positions (relative to the connection of the $Q^1$ ring to the remainder of Formula 1).

Embodiment 6c

A compound of Formula 1 or any one of Embodiments 1 through 6 wherein $Q^1$ is a phenyl ring substituted with three $R^{3a}$ substituents attached at both ortho positions and the para position (relative to the connection of the $Q^1$ ring to the remainder of Formula 1).

Embodiment 7

A compound of Formula 1 or any one of Embodiments 1 through 6c wherein $Q^2$ is a phenyl ring substituted with 1 to 3 substituents independently selected from $R^{3a}$; or a pyrazolyl, imidazolyl, pyridinyl, pyridazinyl, pyrazinyl or pyrimidinyl ring, each ring optionally substituted with up to 3 substituents independently selected from $R^{3a}$ on carbon atom ring members and $R^{3b}$ on nitrogen atom ring members.

Embodiment 8

A compound of Embodiment 7 wherein $Q^2$ is a phenyl ring substituted with 1 to 3 substituents independently selected from $R^{3a}$; or a pyrazolyl, imidazolyl or pyridinyl ring, each ring optionally substituted with 1 to 3 substituents independently selected from $R^{3a}$ on carbon atom ring members and $R^{3b}$ on nitrogen atom ring members.

Embodiment 9

A compound of Embodiment 8 wherein $Q^2$ is a phenyl ring substituted with 1 to 3 substituents independently selected from $R^{3a}$.

Embodiment 9a

A compound of Embodiment 9 wherein $Q^2$ is a phenyl ring substituted with 2 to 3 substituents independently selected from $R^{3a}$.

Embodiment 9b

A compound of Embodiment 9 wherein $Q^2$ is a phenyl ring substituted with 1 substituent independently selected from $R^{3a}$.

Embodiment 9c

A compound of Embodiment 9 wherein $Q^2$ is a phenyl ring substituted with 2 substituents independently selected from $R^{3a}$.

Embodiment 9d

A compound of Embodiment 9 wherein $Q^2$ is a phenyl ring substituted with 3 substituents independently selected from $R^{3a}$.

Embodiment 9e

A compound of Formula 1 or any one of Embodiments 1 through 9 wherein $Q^2$ is a phenyl ring substituted with two $R^{3a}$ substituents attached at an ortho position and the para position (relative to the connection of the $Q^2$ ring to the remainder of Formula 1).

Embodiment 9f

A compound of Formula 1 or any one of Embodiments 1 through 9 wherein $Q^2$ is a phenyl ring substituted with two $R^{3a}$ substituents attached at both ortho positions (relative to the connection of the $Q^2$ ring to the remainder of Formula 1).

Embodiment 9g

A compound of Formula 1 or any one of Embodiments 1 through 9 wherein $Q^2$ is a phenyl ring substituted with three $R^{3a}$ substituents attached at both ortho positions and the para position (relative to the connection of the $Q^2$ ring to the remainder of Formula 1).

Embodiment 10

A compound of Embodiment 8 wherein $Q^2$ is a pyridinyl ring optionally substituted with up to 3 substituents independently selected from $R^{3a}$.

Embodiment 11

A compound of Embodiment 10 wherein $Q^2$ is a pyridinyl ring substituted with 1 to 3 substituents independently selected from $R^{3a}$.

Embodiment 12

A compound of Formula 1 or any one of Embodiments 1 through 11 wherein when $Q^2$ is a 6-membered fully unsaturated heterocyclic ring (e.g., pyridinyl, pyridazinyl, pyrazinyl or pyrimidinyl), then $Q^2$ is substituted with at least one $R^{3a}$ substituent attached at an ortho position (relative to the connection of the $Q^2$ ring to the remainder of Formula 1).

Embodiment 13

A compound of Formula 1 or any one of Embodiments 1 through 12 wherein when $Q^1$ and $Q^2$ are each a phenyl substituted with 1 to 3 substituents independently selected from $R^{3a}$, then one ring is substituted with 2 to 3 substituents and the ring is substituted with 1 to 3 substituents.

Embodiment 14

A compound of Formula 1 or any one of Embodiments 1 through 12 wherein when $Q^1$ and $Q^2$ are each a phenyl ring substituted with 1 to 3 substituents independently selected from $R^{3a}$, then one ring is substituted with 2 to 3 substituents and the other ring is substituted with 1 to 2 substituents.

Embodiment 14a

A compound of Formula 1 or any one of Embodiments 1 through 12 wherein when $Q^1$ and $Q^2$ are each a phenyl ring substituted with 1 to 3 substituents independently selected from $R^{3a}$, then one ring is substituted with 3 substituents and the other ring substituted with 2 substituents.

Embodiment 14b

A compound of Formula 1 or any one of Embodiments 1 through 12 wherein $Q^1$ and $Q^2$ are both a phenyl ring substituted with 2 substituents independently selected from $R^{3a}$.

Embodiment 15

A compound of Formula 1 or any one of Embodiments 1 through 14b wherein $R^1$ is $C_1$-$C_2$ alkyl, —$CH_2F$, —$CH_2Cl$ or cyclopropyl. Embodiment 16
A compound of Embodiment 15 wherein $R^1$ is methyl, —$CH_2F$ or —$CH_2Cl$.

Embodiment 17

A compound of Embodiment 16 wherein $R^1$ is methyl.

Embodiment 18

A compound of Formula 1 or any one of Embodiments 1 through 17 wherein $R^2$ is H, halogen, cyano, $C_1$-$C_2$ alkyl, $C_2$-$C_4$ alkenyl, halomethyl, cyanomethyl, hydroxymethyl, $C_2$-$C_3$ alkoxyalkyl, $C_1$-$C_2$ alkoxy or $C_1$-$C_2$ haloalkoxy.

Embodiment 18a

A compound of Embodiment 18 wherein $R^2$ is halogen, cyano, $C_1$-$C_2$ alkyl, halomethyl, cyanomethyl, hydroxymethyl, $C_1$-$C_2$ alkoxy or $C_1$-$C_2$ haloalkoxy.

Embodiment 18b

A compound of Embodiment 18a wherein $R^2$ is halogen, cyano, $C_1$-$C_2$ alkyl, halomethyl, cyanomethyl, hydroxymethyl or methoxy.

Embodiment 19

A compound of Embodiment 18b wherein $R^2$ is halogen, cyano, methyl, halomethyl or methoxy.

Embodiment 20

A compound of Embodiment 19 wherein $R^2$ is Br, Cl, F, cyano, methyl or methoxy.

Embodiment 20a

A compound of Embodiment 20 wherein $R^2$ is Br, Cl, methyl or methoxy.

Embodiment 20b

A compound of Embodiment 20a wherein $R^2$ is Br, Cl or methoxy.

Embodiment 21

A compound of Embodiment 20a wherein $R^2$ is methyl.

Embodiment 22

A compound of Formula 1 or any one of Embodiments 1 through 21 wherein each $R^{3a}$ is independently halogen, cyano, $C_1$-$C_2$ alkyl, $C_1$-$C_2$ haloalkyl, cyclopropyl, $C_1$-$C_2$ alkoxy, $C_1$-$C_2$ alkylthio, $C_2$-$C_3$ alkylcarbonyl or —U—V-T.

Embodiment 23

A compound of Embodiment 22 wherein each $R^{3a}$ is independently halogen, cyano, methyl, halomethyl, cyclopropyl, methoxy, methylthio, methylcarbonyl or —U—V-T.

Embodiment 24

A compound of Embodiment 23 wherein each $R^{3a}$ is independently halogen, cyano, methyl, halomethyl or methoxy.

Embodiment 25

A compound of Embodiment 24 wherein each $R^{3a}$ is independently halogen, cyano or methoxy.

Embodiment 26

A compound of Embodiment 25 wherein each $R^{3a}$ is independently Br, Cl, F, cyano or methoxy.

Embodiment 27

A compound of Embodiment 26 wherein each $R^{3a}$ is independently Cl or F.

Embodiment 28

A compound of Formula 1 or any one of Embodiments 1 through 27 wherein each U is independently $ON(R^{10})$ or a direct bond.

Embodiment 29

A compound of Embodiment 28 wherein each $R^{10}$ is independently H or methyl.

Embodiment 30

A compound of Embodiment 28 wherein each U is independently O, NH or a direct bond.

Embodiment 31

A compound of Formula 1 or any one of Embodiments 1 through 30 wherein each V is independently $C_1$-$C_4$ alkylene, wherein up to 1 carbon atom is selected from C(=O).

Embodiment 32

A compound of Embodiment 31 wherein each V is independently $C_1$-$C_3$ alkylene.

Embodiment 33

A compound of Formula 1 or any one of Embodiments 1 through 32 wherein each T is independently $N(R^{11a})(R^{11b})$ or $OR^{12}$.

Embodiment 34

A compound of Formula 1 or any one of Embodiments 1 through 33 wherein each $R^{11a}$ and $R^{11b}$ is independently H, $C_1$-$C_6$ alkyl or $C_1$-$C_6$ haloalkyl.

Embodiment 35

A compound of Embodiment 34 wherein each $R^{11a}$ and $R^{11b}$ is independently H or methyl.

Embodiment 36

A compound of Formula 1 or any one of Embodiments 1 through 35 wherein each $R^{12}$ is independently H, $C_1$-$C_6$ alkyl or $C_1$-$C_6$ haloalkyl.

Embodiment 37

A compound Embodiment 36 wherein each $R^{12}$ is independently H, methyl or halomethyl.

Embodiment 38

A compound of Formula 1 or any one of Embodiments 1 through 37 wherein each $R^{3b}$ is independently cyano, $C_1$-$C_2$ alkyl, cyclopropyl or $C_2$-$C_3$ alkoxyalkyl.

Embodiment 39

A compound of Embodiment 38 wherein each $R^{3b}$ is methyl.

Embodiment 40

A compound of Formula 1 or any one of Embodiments 1 through 39 wherein $R^4$ is halogen or —SC≡N.

Embodiment 41

A compound of Embodiment 40 wherein $R^4$ is —SC≡N.

Embodiment 42

A compound of Embodiment 40 wherein $R^4$ is halogen.

Embodiment 43

A compound of Embodiment 42 wherein $R^4$ is Br, Cl or F.

Embodiment 44

A compound of Formula 1 or any one of Embodiments 1 through 39 wherein $R^4$ is —$OR^7$.

Embodiment 45

A compound of Formula 1 or any one of Embodiments 1 through 44 wherein $R^4$ is Br, Cl, F, —$OR^7$ or —SC≡N.

Embodiment 46

A compound of Embodiment 45 wherein $R^4$ is Br, Cl, F or —$OR^7$.

Embodiment 47

A compound of Formula 1 or any one of Embodiments 1 through 46 wherein $R^5$ is H or methyl.

Embodiment 48

A compound of Embodiment 47 wherein $R^5$ is H.

Embodiment 49

A compound of Formula 1 or any one of Embodiments 1 through 48 wherein $R^7$ is H, $C_1$-$C_3$ alkyl, $C_2$-$C_6$ alkenyl, $C_1$-$C_3$ haloalkyl, cyclopropyl, $C_2$-$C_3$ cyanoalkyl, $C_2$-$C_6$ alkoxyalkyl, —S(=O)$_2$O$M^1$ or —C(=W)$R^9$.

Embodiment 50

A compound of Embodiment 49 wherein $R^7$ is H, $C_1$-$C_3$ alkyl, $C_1$-$C_3$ haloalkyl, cyclopropyl, $C_2$-$C_3$ cyanoalkyl, —S(=O)$_2$O$M^1$ or —C(=W)$R^9$.

Embodiment 51

A compound of Embodiment 50 wherein $R^7$ is H, $C_1$-$C_3$ alkyl, $C_1$-$C_3$ haloalkyl, —S(=O)$_2$O$M^1$ or —C(=W)$R^9$.

Embodiment 52

A compound of Embodiment 51 wherein $R^7$ is H, methyl or —C(=W)$R^9$.

Embodiment 53

A compound Embodiment 52 wherein $R^7$ is H or methyl.

Embodiment 54

A compound Embodiment 53 wherein $R^7$ is H.

Embodiment 55

A compound Formula 1 or any one of Embodiments 1 through 54 wherein $R^9$ is methyl or methoxy.

Embodiment 56

A compound of Embodiment 55 wherein $R^9$ is methyl.

Embodiment 57

A compound of Formula 1 or any one of Embodiments 1 through 56 wherein W is O.

Embodiment 58

A compound of Formula 1 or any one of Embodiments 1 through 57 wherein $M^1$ is Na or K.

Embodiment 59

A compound of Embodiment 58 wherein $M^1$ is Na.

Embodiments of this invention, including Embodiments 1-59 above as well as any other embodiments described herein, can be combined in any manner, and the descriptions of variables in the embodiments pertain not only to the compounds of Formula 1 but also to the starting compounds and intermediate compounds useful for preparing the compounds of Formula 1. In addition, embodiments of this invention, including Embodiments 1-59 above as well as any other embodiments described herein, and any combination thereof, pertain to the compositions and methods of the present invention.

Combinations of Embodiments 1-59 are illustrated by:

Embodiment A

A compound of Formula 1 wherein
$Q^1$ is a phenyl ring substituted with 1 to 3 substituents independently selected from $R^{3a}$;
$Q^2$ is a phenyl ring substituted with 1 to 3 substituents independently selected from $R^{3a}$; or a pyrazolyl, imidazolyl, pyridinyl, pyridazinyl, pyrazinyl or pyrimidinyl ring, each ring optionally substituted with up to 3 substituents independently selected from $R^{3a}$ on carbon atom ring members and $R^{3b}$ on nitrogen atom ring members;
$R^1$ is $C_1$-$C_2$ alkyl, —$CH_2F$, —$CH_2Cl$ or cyclopropyl;
$R^2$ is H, halogen, cyano, $C_1$-$C_2$ alkyl, $C_2$-$C_4$ alkenyl, halomethyl, cyanomethyl, hydroxymethyl, $C_2$-$C_3$ alkoxyalkyl, $C_1$-$C_2$ alkoxy or $C_1$-$C_2$ haloalkoxy;
each $R^{3a}$ is independently halogen, cyano, $C_1$-$C_2$ alkyl, $C_1$-$C_2$ haloalkyl, cyclopropyl, $C_1$-$C_2$ alkoxy, $C_1$-$C_2$ alkylthio, $C_2$-$C_3$ alkylcarbonyl or —U—V—T;
each $R^{3b}$ is independently cyano, $C_1$-$C_2$ alkyl, cyclopropyl or $C_2$-$C_3$ alkoxyalkyl;
$R^4$ is Br, Cl, F, —$OR^7$ or —SC≡N;
$R^5$ is H or methyl;
$R^7$ is H, $C_1$-$C_3$ alkyl, $C_2$-$C_6$ alkenyl, $C_1$-$C_3$ haloalkyl, cyclopropyl, $C_2$-$C_3$ cyanoalkyl, $C_2$-$C_6$ alkoxyalkyl, —S(=O)$_2$O$M^1$ or —C(=W)$R^9$;
$R^9$ is methyl or methoxy;
each U is independently O, N($R^{10}$) or a direct bond;

each $R^{10}$ is independently H or methyl;
each V is independently $C_1$-$C_3$ alkylene, wherein up to 1 carbon atom is selected from C(=O);
each T is independently $N(R^{11a})(R^{11b})$ or $OR^{12}$;
each $R^{11a}$ and $R^{11b}$ is independently H or methyl;
each $R^{12}$ is independently H, $C_1$-$C_6$ alkyl or $C_1$-$C_6$ haloalkyl;
W is O; and
$M^1$ is Na or K.

Embodiment B

A compound of Embodiment A wherein
$Q^2$ is a phenyl ring substituted with 1 to 3 substituents independently selected from $R^{3a}$; or a pyrazolyl, imidazolyl or pyridinyl ring, each ring optionally substituted with 1 to 3 substituents independently selected from $R^{3a}$ on carbon atom ring members and $R^{3b}$ on nitrogen atom ring members;
$R^1$ is methyl, —$CH_2F$ or —$CH_2Cl$;
$R^2$ is halogen, cyano, $C_1$-$C_2$ alkyl, halomethyl, cyanomethyl, hydroxymethyl, $C_1$-$C_2$ alkoxy or $C_1$-$C_2$ haloalkoxy;
each $R^{3a}$ is independently halogen, cyano, methyl, halomethyl, cyclopropyl, methoxy, methylthio, methylcarbonyl or —U—V-T;
each $R^{3b}$ is methyl;
$R^4$ is Br, Cl, F or —$OR^7$;
$R^7$ is H, $C_1$-$C_3$ alkyl, $C_1$-$C_3$ haloalkyl, —$S(=O)_2OM^1$ or —$C(=W)R^9$;
each U is independently O, NH or a direct bond;
each V is $C_1$-$C_3$ alkylene; and
each $R^{12}$ is independently H, methyl or halomethyl.

Embodiment C

A compound of Embodiment B wherein
$Q^2$ is a phenyl ring substituted with 1 to 3 substituents independently selected from $R^{3a}$;
$R^1$ is methyl;
$R^2$ is halogen, cyano, methyl, halomethyl or methoxy;
each $R^{3a}$ is independently halogen, cyano, methyl, halomethyl or methoxy;
$R^4$ is —$OR^7$;
$R^5$ is H;
$R^7$ is H, methyl or —$C(=W)R^9$; and
$R^9$ is methyl.

Embodiment D

A compound of Embodiment C wherein
$R^2$ is Br, Cl, methyl or methoxy;
each $R^{3a}$ is independently halogen, cyano or methoxy; and
$R^7$ is H.

Embodiment E

A compound of Embodiment D wherein
$R^2$ methyl;
each $R^{3a}$ is independently Br, Cl, F, cyano or methoxy; and one of $Q^1$ and $Q^2$ is substituted with 2 to 3 substituents and the other of $Q^1$ and $Q^2$ is substituted with 1 to 2 substituents.

Specific embodiments include compounds of Formula 1 selected from the group consisting of:
α-(2-chloro-4-fluorophenyl)-5-(2-chloro-6-fluorophenyl)-1,3-dimethyl-1H-pyrazole-4-methanol;
(αS)-α-(2-chloro-4-fluorophenyl)-5-(2-chloro-6-fluorophenyl)-1,3-dimethyl-1H-pyrazole-4-methanol;
(αR)-α-(2-chloro-4-fluorophenyl)-5-(2-chloro-6-fluorophenyl)-1,3-dimethyl-1H-pyrazole-4-methanol;
α-(2-chloro-4-fluorophenyl)-5-(2,6-fluorophenyl)-1,3-dimethyl-1H-pyrazole-4-methanol;
(αS)-α-(2-chloro-4-fluorophenyl)-5-(2,6-difluorophenyl)-1,3-dimethyl-1H-pyrazole-4-methanol;
(αR)-α-(2-chloro-4-fluorophenyl)-5-(2,6-fluorophenyl)-1,3-dimethyl-1H-pyrazole-4-methanol;
α,5-bis(2-chloro-4-fluorophenyl)-1,3-dimethyl-1H-pyrazole-4-methanol;
5-(2-bromophenyl)-α-(2-chloro-4-fluorophenyl)-1,3-dimethyl-1H-pyrazole-4-methanol;
α-(2-chloro-4-fluorophenyl)-5-(2,6-dichlorophenyl)-1,3-dimethyl-1H-pyrazole-4-methanol;
α-(2-chloro-4-fluorophenyl)-1,3-dimethyl-5-(2,4,6-trifluorophenyl)-1H-pyrazole-4-methanol;
α-(2-bromo-4-fluorophenyl)-5-(2,6-dichlorophenyl)-1,3-dimethyl-1H-pyrazole-4-methanol;
α-(2-bromo-4-fluorophenyl)-5-(2-chloro-fluorophenyl)-1,3-dimethyl-1H-pyrazole-4-methanol;
3-bromo-5-(2-chloro-4-fluorophenyl)-α-(2,4-difluorophenyl)-1-methyl-1H-pyrazole-4-methanol;
5-(2-chloro-4-fluorophenyl)-α-(2,4-difluorophenyl)-1,3-dimethyl-1H-pyrazole-4-methanol;
5-(2,4-dichlorophenyl)-α-(2,4-difluorophenyl)-1,3-dimethyl-1H-pyrazole-4-methanol;
5-(2-chloro-6-fluorophenyl)-α-(2,4-difluorophenyl)-1,3-dimethyl-1H-pyrazole-4-methanol;
α-(2,4-difluorophenyl)-5-(2,6-dichlorophenyl)-1,3-dimethyl-1H-pyrazole-4-methanol;
4-[4-[(2,4-difluorophenyl)hydroxymethyl]-1,3-dimethyl-1H-pyrazol-5-yl]-3,5-difluorobenzonitrile;
5-(2-chloro-6-fluorophenyl)-α-(2,4-dichlorophenyl)-1,3-dimethyl-1H-pyrazole-4-methanol;
5-(2-chloro-6-fluorophenyl)-α-(2,6-dichlorophenyl)-1,3-dimethyl-1H-pyrazole-4-methanol;
5-(2-chloro-4-fluorophenyl)-1,3-dimethyl-α-(2,4,6-trifluorophenyl)-1H-pyrazole-4-methanol;
5-(2-bromo-4-fluorophenyl)-1,3-dimethyl-α-(2,4,6-trifluorophenyl)-1H-pyrazole-4-methanol;
5-(2-chloro-6-fluorophenyl)-α-(2-chloro-4-methoxyphenyl)-1,3-dimethyl-1H-pyrazole-4-methanol;
3-bromo-α-(2-chloro-4-fluorophenyl)-5-(2,6-difluorophenyl)-1-methyl-1H-pyrazole-4-methanol;
3-chloro-α-(2-chloro-4-fluorophenyl)-5-(2,6-difluorophenyl)-1-methyl-1H-pyrazole-4-methanol;
α-(2-chloro-4-fluorophenyl)-5-(2,6-difluorophenyl)-3-methoxy-1-methyl-1H-pyrazole-4-methanol;
α-(2-chloro-4-fluorophenyl)-5-(2-chloro-6-fluorophenyl)-3-methoxy-1-methyl-1H-pyrazole-4-methanol;
5-(2,6-difluorophenyl)-α-(4-fluoro-2-methylphenyl)-3-methoxy-1-methyl-1H-pyrazole-4-methanol;
α-(2-chloro-4-methoxphenyl)-5-(2,6-difluorophenyl)-3-methoxy-1-methyl-1H-pyrazole-4-methanol;
5-(2,6-difluorophenyl)-3-methoxy-α-(4-methoxy-2-methylphenyl)-1-methyl-1H-pyrazole-4-methanol;
5-(2-chloro-6-fluorophenyl)-α-(2-chloro-4-methoxyphenyl)-3-methoxy-1-methyl-1H-pyrazole-4-methanol;
3-chloro-5-(2,6-difluorophenyl)-α-(4-methoxy-2-methylphenyl)-1-methyl-1H-pyrazole-4-methanol;
3-chloro-5-(2,6-difluorophenyl)-α-(2-fluoro-4-methoxyphenyl)-1-methyl-1H-pyrazole-4-methanol;
3-chloro-α-(2-chloro-4-methoxyphenyl)-5-(2,6-difluorophenyl)-1-methyl-1H-pyrazole-4-methanol; and 3-bromo-5-(2,6-difluorophenyl)-α-(4-methoxy-2-meth-ylphenyl)-1-methyl-1H-pyrazole-4-methanol.

As noted in the Summary of the Invention, this invention is also directed to a compound of Formula 1A. Embodiments of Formula 1A include those described in the Summary of the Invention as well as the Embodiments below. In the following Embodiments, Formula 1A includes stereoisomers, N-oxides and salts thereof, and reference to "a compound of Formula 1A" includes the definitions of substituents specified in the Summary of the Invention unless further defined in the Embodiments.

Embodiment A1

A compound of Formula 1A wherein $Q^1$ is a phenyl ring substituted with 1 to 3 substituents independently selected from $R^{3a}$.

Embodiment A2

A compound of Embodiment A1 wherein $Q^1$ is a phenyl ring substituted with 2 to 3 substituents independently selected from $R^{3a}$.

Embodiment A3

A compound of Embodiment A1 wherein $Q^1$ is a phenyl ring substituted with 1 substituent independently selected from $R^{3a}$.

Embodiment A4

A compound of Embodiment A1 wherein $Q^1$ is a phenyl ring substituted with 2 substituents independently selected from $R^{3a}$.

Embodiment A5

A compound of Embodiment A1 wherein $Q^1$ is a phenyl ring substituted with 3 substituents selected from $R^{3a}$.

Embodiment A6

A compound of Formula 1A or any one of Embodiments A1 through A5 wherein $Q^1$ is a phenyl ring substituted with at least one $R^{3a}$ substituent attached at an ortho position (relative to the connection of the $Q^1$ ring to the remainder of Formula 1A).

Embodiment A7

A compound of Formula 1A or any one of Embodiments A1 through A6 wherein $Q^1$ is a phenyl ring substituted with two $R^{3a}$ substituents attached at an ortho position and the para position (relative to the connection of the $Q^1$ ring to the remainder of Formula 1A).

Embodiment A8

A compound of Formula 1A or any one of Embodiments A1 through A6 wherein $Q^1$ is a phenyl ring substituted with two $R^{3a}$ substituents attached at both ortho positions (relative to the connection of the $Q^1$ ring to the remainder of Formula 1A).

Embodiment A9

A compound of Formula 1A or any one of Embodiments A1 through A6 wherein $Q^1$ is a phenyl ring substituted with three $R^{3a}$ substituents attached at both ortho positions and the para position (relative to the connection of the $Q^1$ ring to the remainder of Formula 1A).

Embodiment A10

A compound of Formula 1A or any one of Embodiments A1 through A9 wherein $Q^2$ is a phenyl ring substituted with 1 to 3 substituents independently selected from $R^{3a}$; or a pyrazolyl, imidazolyl, pyridinyl, pyridazinyl, pyrazinyl or pyrimidinyl ring, each ring optionally substituted with up to 3 substituents independently selected from $R^{3a}$ on carbon atom ring members and $R^{3b}$ on nitrogen atom ring members.

Embodiment A11

A compound of Embodiment A10 wherein $Q^2$ is a phenyl ring substituted with 1 to 3 substituents independently selected from $R^{3a}$; or a pyrazolyl, imidazolyl or pyridinyl ring, each ring optionally substituted with 1 to 3 substituents independently selected from $R^{3a}$ on carbon atom ring members and $R^{3b}$ on nitrogen atom ring members.

Embodiment A12

A compound of Embodiment A11 wherein Q2 is a phenyl ring substituted with 1 to 3 substituents independently selected from $R^{3a}$.

Embodiment A13

A compound of Embodiment A12 wherein $Q^2$ is a phenyl ring substituted with 2 to 3 substituents independently selected from $R^{3a}$.

Embodiment A14

A compound of Embodiment A13 wherein $Q^2$ is a phenyl ring substituted with 1 substituent independently selected from $R^{3a}$.

Embodiment A15

A compound of Embodiment A13 wherein $Q^2$ is a phenyl ring substituted with 2 substituents independently selected from $R^{3a}$.

Embodiment A16

A compound of Embodiment A13 wherein $Q^2$ is a phenyl ring substituted with 3 substituents independently selected from $R^{3a}$.

Embodiment A17

A compound of Formula 1A or any one of Embodiments A1 through A16 wherein $Q^2$ is a phenyl ring substituted with two $R^{3a}$ substituents attached at an ortho position and the para position (relative to the connection of the $Q^2$ ring to the remainder of Formula 1A).

Embodiment A18

A compound of Formula 1A or any one of Embodiments A1 through A17 wherein $Q^2$ is a phenyl ring substituted with two $R^{3a}$ substituents attached at both ortho positions (relative to the connection of the $Q^2$ ring to the remainder of Formula 1A).

Embodiment A19

A compound of Formula 1A or any one of Embodiments A1 through A18 wherein $Q^2$ is a phenyl ring substituted with three $R^{3a}$ substituents attached at both ortho positions and the para position (relative to the connection of the $Q^2$ ring to the remainder of Formula 1A).

Embodiment A20

A compound of Embodiment A11 wherein $Q^2$ is a pyridinyl ring optionally substituted with up to 3 substituents independently selected from $R^{3a}$.

Embodiment A21

A compound of Embodiment A20 wherein $Q^2$ is a pyridinyl ring substituted with 1 to 3 substituents independently selected from $R^{3a}$.

Embodiment A22

A compound of Formula 1A or any one of Embodiments A1 through A21 wherein when $Q^2$ is a 6-membered fully unsaturated heterocyclic ring (e.g., pyridinyl, pyridazinyl, pyrazinyl or pyrimidinyl), then $Q^2$ is substituted with at least one $R^{3a}$ substituent attached at an ortho position (relative to the connection of the $Q^2$ ring to the remainder of Formula 1A).

Embodiment A23

A compound of Formula 1A or any one of Embodiments A1 through A22 wherein when $Q^1$ and $Q^2$ are each a phenyl ring substituted with 1 to 3 substituents independently selected from $R^{3a}$, then one ring substituted with 2 to 3 substituents and the other ring substituted with 1 to 3 substituents.

Embodiment A24

A compound of Formula 1A or any one of Embodiments A1 through A23 wherein when $Q^1$ and $Q^2$ are each a phenyl ring substituted with 1 to 3 substituents independently selected from $R^{3a}$, then one ring is substituted with 2 to 3 substituents and the other ring is substituted with 1 to 2 substituents.

Embodiment A25

A compound of Formula 1A or any one of Embodiments A1 through A24 wherein when $Q^1$ and $Q^2$ are each a phenyl ring substituted with 1 to 3 substituents independently selected from $R^{3a}$, then one ring is substituted with 3 substituents and the other ring is substituted with 2 substituents.

Embodiment A26

A compound of Formula 1A or any one of Embodiments A1 through A25 wherein $Q^1$ and $Q^2$ are both a phenyl ring substituted with 2 substituents independently selected from $R^{3a}$.

Embodiment A27

A compound of Formula 1A or any one of Embodiments A1 through A26 wherein X is O, S, $N(R^6)$ or $C(=O)$.

Embodiment A28

A compound of Embodiment A27 wherein X is O, NH or $C(=O)$.

Embodiment A29

A compound of Embodiment A27 wherein X is $N(R^6)$.

Embodiment A29a

A compound of Embodiment A29 wherein X is NH.

Embodiment A30

A compound of Embodiments A28 wherein X is O.

Embodiment A31

A compound of Embodiment A28 wherein X is $C(=O)$.

Embodiment A32

A compound of Formula 1A or any one of Embodiments A1 through A31 wherein $R^1$ is $C_1$-$C_2$ alkyl, —$CH_2F$, —$CH_2Cl$ or cyclopropyl.

Embodiment A33

A compound of Embodiment A32 wherein $R^1$ is methyl, —$CH_2F$ or —$CH_2Cl$.

Embodiment A34

A compound of Embodiment A33 wherein $R^1$ is methyl.

Embodiment A35

A compound of Formula 1A or any one of Embodiments A1 through A34 wherein $R^2$ is H, halogen, cyano, $C_1$-$C_2$ alkyl, $C_2$-$C_4$ alkenyl, halomethyl, cyanomethyl, hydroxymethyl, $C_2$-$C_3$ alkoxyalkyl, $C_1$-$C_2$ alkoxy or $C_1$-$C_2$ haloalkoxy.

Embodiment A36

A compound of Embodiment A35 wherein $R^2$ is halogen, cyano, $C_1$-$C_2$ alkyl, halomethyl, cyanomethyl, hydroxymethyl, $C_1$-$C_2$ alkoxy or $C_1$-$C_2$ haloalkoxy.

Embodiment A37

A compound of Embodiment A36 wherein $R^2$ is halogen, cyano, $C_1$-$C_2$ alkyl, halomethyl, cyanomethyl, hydroxymethyl or methoxy.

Embodiment A38

A compound of Embodiment A37 wherein $R^2$ is halogen, cyano, methyl, halomethyl or methoxy.

Embodiment A39

A compound of Embodiment A38 wherein $R^2$ is Br, Cl, F, cyano, methyl or methoxy.

Embodiment A40

A compound of Embodiment A39 wherein $R^2$ is Br, Cl, methyl or methoxy.

Embodiment A41

A compound of Embodiment A40 wherein $R^2$ is methyl.

Embodiment A42

A compound of Formula 1A or any one of Embodiments A1 through A41 wherein each $R^{3a}$ is independently halogen, cyano, $C_1$-$C_2$ alkyl, $C_1$-$C_2$ haloalkyl, cyclopropyl, $C_1$-$C_2$ alkoxy, $C_1$-$C_2$ alkylthio, $C_2$-$C_3$ alkylcarbonyl or —U—V-T.

Embodiment A43

A compound of Embodiment A42 wherein each $R^{3a}$ is independently halogen, cyano, methyl, halomethyl, cyclopropyl, methoxy, methylthio, methylcarbonyl or —U—V-T.

Embodiment A44

A compound of Embodiment A43 wherein each $R^{3a}$ is independently halogen, cyano, methyl, halomethyl or methoxy.

Embodiment A45

A compound of Embodiment A44 wherein each $R^{3a}$ is independently halogen, cyano or methoxy.

Embodiment A46

A compound of Embodiment A45 wherein each $R^{3a}$ is independently Br, Cl, F, cyano or methoxy.

Embodiment A47

A compound of Embodiment A46 wherein each $R^{3a}$ is independently Cl or F.

Embodiment A48

A compound of Formula 1A or any one of Embodiments A1 through A47 wherein each U is independently O, $N(R^{10})$ or a direct bond.

Embodiment A49

A compound of Embodiment A48 wherein each $R^{10}$ is independently H or methyl.

Embodiment A50

A compound of Embodiment A48 wherein each U is independently O, NH or a direct bond.

Embodiment A51

A compound of Formula 1A or any one of Embodiments A1 through A50 wherein each V is independently $C_1$-$C_4$ alkylene, wherein up to 1 carbon atom is selected from C(=O).

Embodiment A52

A compound of Embodiment A51 wherein each V is independently $C_1$-$C_3$ alkylene.

Embodiment A53

A compound of Formula 1A or any one of Embodiments A1 through A52 wherein each T is independently $N(R^{11a})(R^{11b})$ or $OR^{12}$.

Embodiment A54

A compound of Formula 1A or any one of Embodiments A1 through A53 wherein each $R^{11a}$ and $R^{11b}$ is independently H, $C_1$-$C_6$ alkyl or $C_1$-$C_6$ haloalkyl.

Embodiment A55

A compound of Embodiment A54 wherein each $R^{11a}$ and $R^{11b}$ is independently H or methyl.

Embodiment A56

A compound of Formula 1A or any one of Embodiments A1 through A55 wherein each $R^{12}$ is independently H, $C_1$-$C_6$ alkyl or $C_1$-$C_6$ haloalkyl.

Embodiment A57

A compound Embodiment A56 wherein each $R^{12}$ is independently H, methyl or halomethyl.

Embodiment A58

A compound of Formula 1A or any one of Embodiments A1 through A57 wherein each $R^{3b}$ is independently cyano, $C_1$-$C_2$ alkyl, cyclopropyl or $C_2$-$C_3$ alkoxyalkyl.

Embodiment A59

A compound of Embodiment A58 wherein each $R^{3b}$ is methyl.

Embodiment A60

A compound of Formula 1A or any one of Embodiments A1 through A59 wherein $R^6$ is H, hydroxy, $C_1$-$C_3$ alkyl, $C_1$-$C_3$ haloalkyl, $C_2$-$C_3$ alkoxyalkyl, —CH(=O), —$OR^7$, —$OS(=O)_2M^1$, —$S(=O)_nR^8$ or —$C(=W)R^9$.

Embodiment A61

A compound of Embodiments A60 wherein $R^6$ is H, methyl, halomethyl or —$OR^7$.

Embodiment A62

A compound of Embodiment A61 wherein $R^6$ is H.

Embodiment A63

A compound of Formula 1A or any one of Embodiments A1 through A62 wherein $R^7$ is H, $C_1$-$C_3$ alkyl, $C_2$-$C_6$ alkenyl, $C_1$-$C_3$ haloalkyl, cyclopropyl, $C_2$-$C_3$ cyanoalkyl, $C_2$-$C_6$ alkoxyalkyl, —S(=O)$_2$OM$^1$ or —C(=W)R$^9$.

Embodiment A64

A compound of Embodiment A63 wherein R$^7$ is H, $C_1$-$C_3$ alkyl, $C_1$-$C_3$ haloalkyl, cyclopropyl, $C_2$-$C_3$ cyanoalkyl, —S(=O)$_2$OM$^1$ or —C(=W)R$^9$.

Embodiment A65

A compound of Embodiment A64 wherein R$^7$ is H, $C_1$-$C_3$ alkyl, $C_1$-$C_3$ haloalkyl, —S(=O)$_2$OM$^1$ or —C(=W)R$^9$.

Embodiment A66

A compound of Embodiment A65 wherein R$^7$ is H, methyl or —C(=W)R$^9$.

Embodiment A67

A compound Embodiment A66 wherein R$^7$ is H or methyl.

Embodiment A68

A compound Embodiment A67 wherein R$^7$ is H.

Embodiment A69

A compound of Formula 1A or any one of Embodiments A1 through A68 wherein R$^8$ is methyl.

Embodiment A70

A compound Formula 1A or any one of Embodiments A1 through A69 wherein R$^9$ is methyl or methoxy.

Embodiment A71

A compound of Embodiment A70 wherein R$^9$ is methyl.

Embodiment A72

A compound of Formula 1A or any one of Embodiments A1 through A72 wherein W is O.

Embodiment A73

A compound of Formula 1A or any one of Embodiments A1 through A72 wherein M$^1$ is Na or K.

Embodiment A74

A compound of Embodiment A73 wherein M$^1$ is Na.

Embodiments of this invention, including Embodiments A1-A74 above as well as any other embodiments described herein, can be combined in any manner, and the descriptions of variables in the embodiments pertain not only to the compounds of Formula 1A but also to the starting compounds and intermediate compounds useful for preparing the compounds of Formula 1A. In addition, embodiments of this invention, including Embodiments A1-A74 above as well as any other embodiments described herein, and any combination thereof, pertain to the compositions and methods of the present invention.

Combinations of Embodiments A1-A74 are illustrated by:

Embodiment F

A compound of Formula 1A wherein
Q$^1$ is a phenyl ring substituted with 1 to 3 substituents independently selected from R$^{3a}$;
Q$^2$ is a phenyl ring substituted with 1 to 3 substituents independently selected from R$^{3a}$; or a pyrazolyl, imidazolyl, pyridinyl, pyridazinyl, pyrazinyl or pyrimidinyl ring, each ring optionally substituted with up to 3 substituents independently selected from R$^{3a}$ on carbon atom ring members and R$^{3b}$ on nitrogen atom ring members;
X is O, S, N(R$^6$) or C(=O);
R$^1$ is $C_1$-$C_2$ alkyl, —CH$_2$F, —CH$_2$Cl or cyclopropyl;
R$^2$ is H, halogen, cyano, $C_1$-$C_2$ alkyl, $C_2$-$C_4$ alkenyl, halomethyl, cyanomethyl, hydroxymethyl, $C_2$-$C_3$ alkoxyalkyl, $C_1$-$C_2$ alkoxy or $C_1$-$C_2$ haloalkoxy;
each R$^{3a}$ is independently halogen, cyano, $C_1$-$C_2$ alkyl, $C_1$-$C_2$ haloalkyl, cyclopropyl, $C_1$-$C_2$ alkoxy, $C_1$-$C_2$ alkylthio, $C_2$-$C_3$ alkylcarbonyl or —U—V-T;
each R$^{3b}$ is independently cyano, $C_1$-$C_2$ alkyl, cyclopropyl or $C_2$-$C_3$ alkoxyalkyl;
R$^6$ is H, hydroxy, —CH(=O), $C_1$-$C_3$ alkyl, $C_1$-$C_3$ haloalkyl, $C_2$-$C_3$ alkoxyalkyl, —OR$^7$, —S(=O)$_2$OM$^1$, —S(=O)$_n$R$^8$ or —C(=W)R$^9$;
R$^7$ is H, $C_1$-$C_3$ alkyl, $C_2$-$C_6$ alkenyl, $C_1$-$C_3$ haloalkyl, cyclopropyl, $C_2$-$C_3$ cyanoalkyl, $C_2$-$C_6$ alkoxyalkyl, —S(=O)$_2$OM$^1$ or —C(=W)R$^9$;
R$^8$ is methyl;
R$^9$ is methyl or methoxy;
each U is independently O, N(R$^{10}$) or a direct bond;
each R$^{10}$ is independently H or methyl;
each V is independently $C_1$-$C_3$ alkylene, wherein up to 1 carbon atom is selected from C(=O);
each T is independently N(R$^{11a}$)(R$^{11b}$) or OR$^{12}$;
each R$^{11a}$ and R$^{11b}$ is independently H or methyl;
each R$^{12}$ is independently H, $C_1$-$C_6$ alkyl or $C_1$-$C_6$ haloalkyl;
W is O; and
M$^1$ is Na or K.

Embodiment G

A compound of Embodiment F wherein
Q$^2$ is a phenyl ring substituted with 1 to 3 substituents independently selected from R$^{3a}$; or a pyrazolyl, imidazolyl or pyridinyl ring, each ring optionally substituted with 1 to 3 substituents independently selected from R$^{3a}$ on carbon atom ring members and R$^{3b}$ on nitrogen atom ring members;
R$^1$ is methyl, —CH$_2$F or —CH$_2$Cl;
R$^2$ is halogen, cyano, $C_1$-$C_2$ alkyl, halomethyl, cyanomethyl, hydroxymethyl, $C_1$-$C_2$ alkoxy or $C_1$-$C_2$ haloalkoxy;
each R$^{3a}$ is independently halogen, cyano, methyl, halomethyl, cyclopropyl, methoxy, methylthio, methylcarbonyl or —U—V-T;
each R$^{3b}$ is methyl;
R$^6$ is H, methyl, halomethyl or —OR$^7$;
R$^7$ is H, $C_1$-$C_3$ alkyl, $C_1$-$C_3$ haloalkyl, —S(=O)$_2$OM$^1$ or —C(=W)R$^9$;
each U is independently O, NH or a direct bond;
each V is $C_1$-$C_3$ alkylene; and
each R$^{12}$ is independently H, methyl or halomethyl.

Embodiment H

A compound of Embodiment G wherein
Q$^2$ is a phenyl ring substituted with 1 to 3 substituents independently selected from R$^{3a}$;
R$^1$ is methyl;
R$^2$ is halogen, cyano, methyl, halomethyl or methoxy;
each R$^{3a}$ is independently halogen, cyano, methyl, halomethyl or methoxy;
R$^7$ is H, methyl, or —C(=W)R$^9$; and
R$^9$ is methyl.

Embodiment I

A compound of Embodiment H wherein
X is O, S, NH or C(=O);
R$^2$ is Br, Cl, methyl or methoxy; and
each R$^{3a}$ is independently halogen, cyano or methoxy.

Embodiment J

A compound of Embodiment I wherein
R$^2$ methyl;
each R$^{3a}$ is independently Br, Cl, F, cyano or methoxy; and
one of Q$^1$ and Q$^2$ is substituted with 2 to 3 substituents and the other of Q$^1$ and Q$^2$ is substituted with 1 to 2 substituents.

Specific embodiments include compounds of Formula 1A selected from the group consisting of:
5-(2-chloro-4-methoxyphenyl)-4-(2,4-difluorophenoxy)-1,3-dimethyl-1H-pyrazole;
4-(2-chloro-4-fluorophenoxy)-5-(2-chloro-4-methoxyphenyl)-1,3-dimethyl-1H-pyrazole;
3-chloro-4-[4-(2-chloro-4-fluorophenoxy)-1,3-dimethyl-1H-pyrazol-5-yl]benzonitrile;
4-[[5-(2-chloro-4-fluorophenyl)-1,3-dimethyl-1H-pyrazol-4-yl]amino]-3,5-difluorobenzonitrile;
N,5-bis(2-chloro-4-fluorophenyl)-1,3-dimethyl-1H-pyrazol-4-amine;
3-chloro-4-[[5-(2-chloro-4-fluorophenyl)-1,3-dimethyl-1H-pyrazol-4-yl]oxy]benzonitrile;
5-(2-chloro-4-fluorophenyl)-N-(2,4-dichlorophenyl)-1,3-dimethyl-1H-pyrazole-4-amine;
5-(2-chloro-4-fluorophenyl)-N-(4-chloro-2-fluorophenyl)-1,3-dimethyl-1H-pyrazole-4-amine;
4-(2-chloro-4-fluorobenzoyl)-5-(2,4-difluorophenyl)-1-methyl-1H-pyrazole-3-carbonitrile;
N-(2-bromo-4-fluorophenyl)-5-(2-chloro-4-fluorophenyl)-1,3-dimethyl-1H-pyrazole-4-amine;
N-(2,4-dichlorophenyl)-5-(2,4-difluorophenyl)-1,3-dimethyl-1H-pyrazol-4-amine; and
[5-(2,4-dichlorophenyl)-1,3-dimethyl-1H-pyrazol-4-yl](2,4-difluorophenyl)methanone.

Of note are compounds of Formula 1 and Formula 1A (including all stereoisomers), N-oxides, and salts thereof (including but not limited to Embodiments 1-59 and A1-A74 above) wherein R$^2$ is halogen, cyano, C$_1$-C$_2$ alkyl, haloethyl, cyanomethyl, hydroxymethyl, cyclopropyl, halocyclopropyl, methylthio or methoxy.

Of further note are compounds of Formula 1 and Formula 1A (including all stereoisomers), N-oxides, and salts thereof (including but not limited to Embodiments 1-59 and A1-A74 above) wherein R$^7$ is H, C$_1$-C$_6$ alkyl, C$_1$-C$_6$ haloalkyl, C$_2$-C$_6$ alkenyl, C$_3$-C$_6$ alkynyl, C$_3$-C$_6$ cycloalkyl, C$_2$-C$_6$ cyanoalkyl, —CH(=O), —S(=O)$_2$OM$^1$ or —C(=W)R$^9$.

Additionally, of note are compounds of Formula 1 and Formula 1A (including all stereoisomers), N-oxides, and salts thereof (including but not limited to Embodiments 1-59 and A1-A74 above) wherein when each Q$^1$ and Q$^2$ is a phenyl ring substituted with 1 to 5 substituents independently selected from R$^{3a}$, then Q$^2$ is substituted with at least one R$^{3a}$ substituent at an ortho position.

Also of note are compounds of Formula 1 (including all stereoisomers), N-oxides, and salts thereof (including but not limited to Embodiments 1-59 above) wherein R$^4$ is halogen, —OR$^7$ This invention provides a fungicidal composition comprising a compound of Formula 1 or Formula 1A (including all stereoisomers, N-oxides, and salts thereof), and at least one other fungicide. Of note as embodiments of such compositions are compositions comprising a compound corresponding to any of the compound embodiments described above.

This invention provides a fungicidal composition comprising a compound of Formula 1 or Formula 1A (including all stereoisomers, N-oxides, and salts thereof) (i.e. in a fungicidally effective amount), and at least one additional component selected from the group consisting of surfactants, solid diluents and liquid diluents. Of note as embodiments of such compositions are compositions comprising a compound corresponding to any of the compound embodiments described above.

This invention provides a method for controlling plant diseases caused by fungal plant pathogens comprising applying to the plant or portion thereof, or to the plant seed, a fungicidally effective amount of a compound of Formula 1 or Formula 1A (including all stereoisomers, N-oxides, and salts thereof). Of note as embodiments of such methods are methods comprising applying a fungicidally effective amount of a compound corresponding to any of the compound embodiments describe above. Of particular note are embodiments where the compounds are applied as compositions of this invention.

One or more of the following methods and variations as described in Schemes 1-9 can be used to prepare the compounds of Formula 1 and compounds of Formula 1A. The definitions of Q$^1$, Q$^2$, R$^1$, R$^2$, R$^4$, R$^5$ and X in the compounds of Formulae 1-17 below are as defined above in the Summary of the Invention unless otherwise noted.

Certain compounds of Formula 1 and Formula 1A can be prepared as shown in Scheme 1. In this method a compound of Formula 2 is first treated with an organometallic agent of Formula 3 such an alkyl lithium base (e.g., n-butyllithium, s-butyllithium or lithium diisopropylamide) or a Grignard reagent in a solvent such as toluene, ethyl ether, tetrahydrofuran or dimethoxymethane at temperatures ranging from about −78° C. to ambient temperature. Anions of Formula 2a (i.e. metallated intermediates of Formula 2 generated in situ) are then contacted with an electrophile of Formulae 4 or 5. The use and choice of an appropriate electrophile of Formulae 4 or 5 will depend on the compound of Formula 1 or Formula 1A desired and will be apparent to one skilled in chemical synthesis. For example, aldehydes of the formula Q$^1$CHO provide compounds Formula 1 wherein R$^4$ is OH and R$^5$ is H; benzoyl chlorides of formula Q$^1$C(=O)Cl or benzamides of formula Q$^1$C(=O)N(Me)OMe provide compounds Formula 1A wherein X is C(=O), chlorosulfides of formula Q$^1$SCl or disulfies formula of Q$^1$S—S-Q$^1$ provide compounds Formula 1A wherein X is S, and nitrosobenzenes of formula Q$^1$N(=O) provide compounds Formula 1A wherein X is N(OH). In cases where the electrophile is Q$^1$C(=O)Cl, the addition of a second organometallic agent such as zinc chloride, zinc bromide or a monovalent copper salt such as copper(I) iodide or copper(I) cyanide before the addition of the electrophile promotes reactivity. There are a wide-variety of general methods described in the synthetic literature for metallationialkylation reactions which can be readily adapted to prepare compounds of the present invention. In the present disclosure, Example 4, Step D, Example 6 and Example 9, Step E illustrate the method of Scheme 1.

*Letters* 2009, 11, 1659-1662, *Journal of the American Chemical Society* 2006, 128, 9998-9999, and *Acta Chemica Scandinavica* 1991, 45, 925-929. Also, Examples 8 and 11 illustrate the preparation of a compound of Formula 1a from the corresponding ketone of Formula 1Aa.

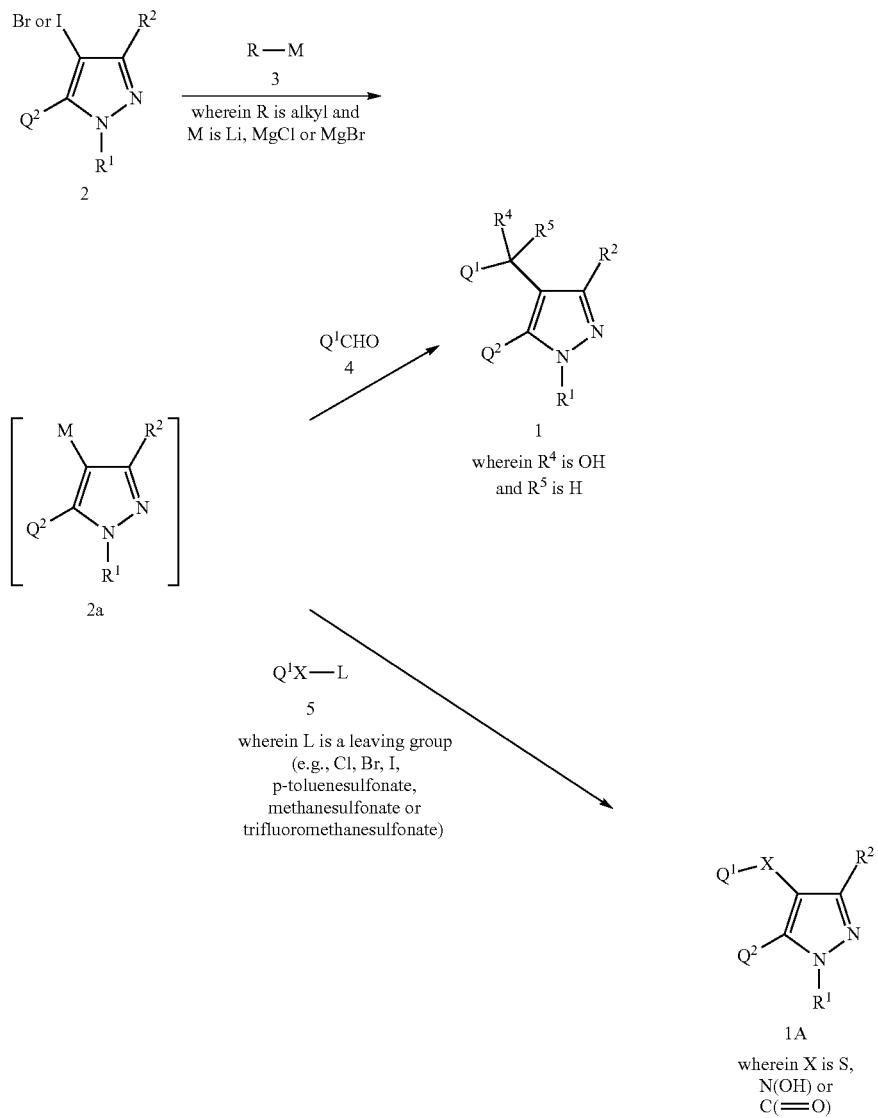

Electrophiles of Formulae 4 and 5 are commercially available and can be prepared by methods known in the art. Compounds of Formula 2 are known and can be prepared by the method disclosed in Scheme 3 below, and by a variety of methods disclosed in the chemical literature.

As shown in Scheme 2, compounds of Formula 1a (i.e. Formula 1 wherein $R^4$ is OH and $R^5$ is H) can be reduced to provide the keto compounds of Formula 1Aa (i.e. Formula 1A wherein X is C(=O)) using standard reduction techniques. Typical reaction conditions involve contacting a boron-based reducing agent such as sodium borohydride or sodium triacetoxyborohydride with the compound of Formula 1Aa in a solvent such as lower alcohols or tetrahydrofuran. Other techniques known to those skilled in the art may also be employed. For relevant references see, for example, *Organic*

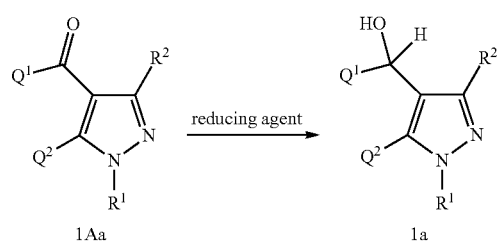

As shown in Scheme 3, keto compounds of Formula 1Aa (i.e. Formula 1A wherein X is C(=O)) can also be treated with alkylmagnesium halides to provide compounds of Formula 1b (i.e. Formula 1 wherein $R^4$ is OH and $R^5$ is $C_1$-$C_4$ alkyl). Typically the reaction use run in presence of zinc chloride and in a solvent such as diethyl ether or tetrahydrofuran at temperatures from about 0-100° C. (for references see, for example, *Organic Lett.* 2009, 11, 1659-1662, *J. Am. Chem. Soc.* 2006, 128, 9998-9999, and *Acta Chemica Scandinavica* 1991, 45, 925-929).

Scheme 3

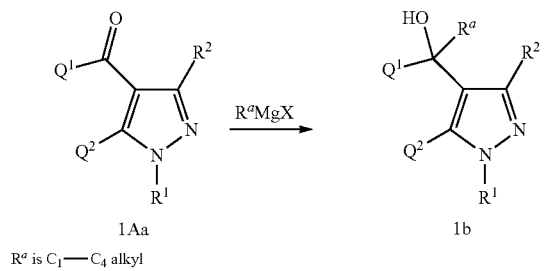

$R^a$ is $C_1$—$C_4$ alkyl

In an alternate approach to the method of Scheme 1, pyrazoles of Formula 1Aa (i.e. Formula 1A wherein X is C(=O)) can be prepared from compounds of Formula 6 using Friedel-Crafts acylation conditions as illustrated in Scheme 4. In this method, the compound of Formula 6 is contacted with an acid chloride of Formula 7 in the presence of a Lewis acid (e.g., aluminum chloride, boron trifluoride diethyl etherate or tin tetrachloride) in a solvent such as dichloromethane, tetrachloroethane, or nitrobenzene, at temperatures ranging between about 0 to 200° C. Present Example 7 and Example 10, Step C illustrate the method of Scheme 4.

Scheme 4

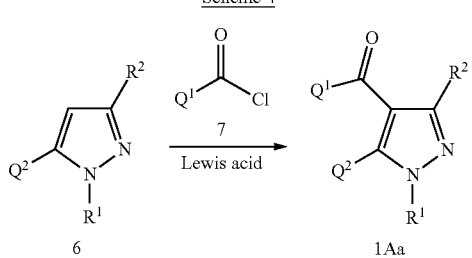

As shown in Scheme 5, Compounds of Formula 1c (i.e. Formula 1 wherein $R^4$ is OH) can be converted to the compounds of Formula 1d (i.e. Formula 1 wherein $R^4$ is halogen) using a variety of conditions published in the chemical literature. For example, treatment of a compound of Formula 1c with a fluorinating agent (e.g., bis(2-methoxyethyl)aminosulfur (Deoxo-Fluor®), diethylaminosulfur trifluoride (DAST), HF-pyridine (Olah's reagent) or sulfur tetrafluoride) provides compounds of Formula Formula 1d wherein $R^4$ is F. For reaction conditions see C. J. Wang, *Organic Reactions* 2005, Vol. 34 (Wiley, New York, 1951) Chapter 2, pp. 319-321; also, present Example 5 illustrates the preparation of a compound of Formula 1d wherein $R^4$ is F and $R^5$ is H. Compounds of Formula 1d wherein $R^4$ is Br can be prepared by treating the corresponding compound of Formula 1c with hydrobromic acid in a solvent such as glacial acetic acid using the method described by Beukers et al., *Journal of Medicinal Chemistry* 2004, 47(15), 3707-3709. Compounds of Formula 1d wherein $R^4$ is Cl can be prepared by treating the corresponding compound of Formula 1c with thionyl chloride or phosphorus pentachloride in presence of a base such as triethylamine or pyridine in a solvent such as dichloromethane or pyridine at 25-110° C. Compounds of Formula 1d wherein $R^4$ is I can be prepared by reacting corresponding compounds of Formula 1c with sodium iodide or potassium iodide in presence of $BF_3.Et_2O$ and an ether solvent such as 1,4-dioxane or with hydroiodic acid in a solvent such as acetonitrile at 25-70° C. according to general methods described in *Tetrahedron Letters* 2001, 42, 951-953 and *Journal of the American Chemical Society* 1965, 87, 539-42.

Scheme 5

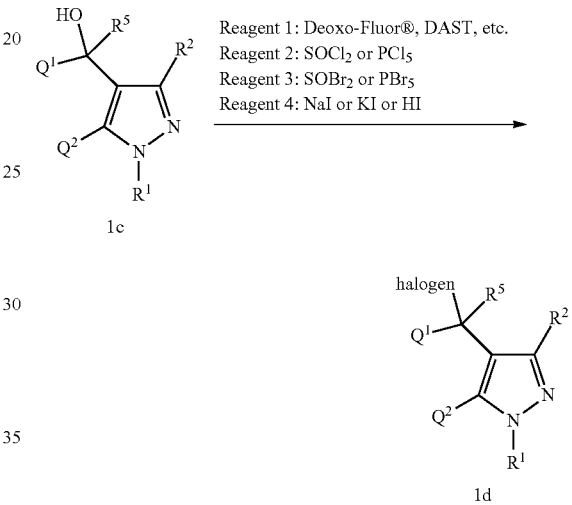

halogen is F if Reagent 1 is used
halogen is Cl is Reagent 2 is used
halogen is Br if Reagent 3 is used
halogen is I if Reagent 4 is used As shown in Scheme 6, pyrazole intermediates of Formula 2 are readily prepared from corresponding pyrazoles of Formula 6 by treatment with a halogenating agent. Suitable halogenating agents for this method include N-bromosuccinimide (NBS), N-iodosuccinimide (NIS), bromine, sodium bromite, thionyl chloride, oxalyl chloride, phenylphosphonic dichloride or phosgene. Particularly useful is N-bromosuccinimide (NBS) and N-iodo-succinimide (NIS). Suitable solvents for this reaction include, for example, N,N-dimethyl-formamide, N,N-dimethylacetamide, dichloromethane, chloroform, chlorobutane, benzene, xylenes, chlorobenzene, tetrahydrofuran, p-dioxane, acetonitrile, and the like. Optionally, an organic base such as triethylamine, pyridine, N,N-dimethylaniline, and the like can be added. Typical reaction temperatures range from about ambient temperature to 200° C. For representative procedures see Czarnocki et al., *Synthesis* 2006, 17, 2855-2864; Brana et al., *Journal of Medicinal Chemistry* 2005, 48, 6843-6854; Liu et al., *Journal of Medicinal Chemistry* 2007, 50, 3086-3100 and Chan et al., *Journal of Medicinal Chemistry* 2005, 48, 4420-4431. The method of Scheme 6 is also illustrated in Example 4, Step C, Example 3, Step C and Example 9, Step D.

Scheme 6

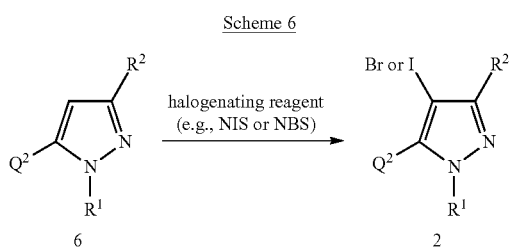

As shown in Scheme 7, compounds of Formula 6 can be prepared by reaction of a 4-bromo or 4-iodo pyrazole of Formula 8 under transition-metal-catalyzed cross-coupling reaction conditions. In this method reaction of a pyrazole of Formula 8 with a compound of formula $Q^2$-$M^1$ in the presence of a suitable palladium, copper or nickel catalyst, affords the corresponding compound of Formula 6. In this method compounds of formula $Q^2$-$M^1$ are organoboronic acids (e.g., $M^1$ is $B(OH)_2$), organoboronic esters (e.g., $M^1$ is $B(-OC(CH_3)_2C(CH_3)_2O-)$), organotrifluoroborates (e.g., $M^1$ is $BF_3K$), organotin reagents (e.g., M is $Sn(n-Bu)_3$, $Sn(Me)_3$), Grignard reagents (e.g., $M^1$ is MgBr or MgCl) or organozinc reagents (e.g., $M^1$ is ZnBr or ZnCl). Suitable metal catalysts include, but are not limited to: palladium(II) acetate, palladium(II) chloride, tetrakis(triphenylphosphine)-palladium(0), bis(triphenylphosphine)palladium(II) dichloride, dichloro[1,1'-bis(diphenyl-phosphino)ferrocene]palladium(II), bis(triphenylphosphine)dichloronickel(II) and copper(I) salts (e.g., copper(I) iodide, copper(I) bromide, copper(I) chloride, copper(I) cyanide or copper(I) triflate). Optimal conditions for each reaction will depend on the catalyst used and the counterion attached to the coupling reagent (i.e. $M^1$), as is understood by one skilled in the art. In some cases the addition of a ligand such as a substituted phosphine or a substituted bis-phosphinoalkane promotes reactivity. Also, the presence of a base such as an alkali carbonate, tertiary amine or alkali fluoride may be necessary for some reactions involving organoboron reagents of the formula $Q^2$-$M^1$. For reviews of this type of reaction see: E. Negishi, *Handbook of Organopalladium Chemistry for Organic Synthesis*, John Wiley and Sons, Inc., New York, 2002; N. Miyaura, *Cross-Coupling Reactions: A Practical Guide*, Springer, N.Y., 2002; H. C. Brown et al., *Organic Synthesis via Boranes*, Vol. 3, Aldrich Chemical Co., Milwaukee, Wis., 2002; Suzuki et al., *Chemical Review* 1995, 95, 2457-2483 and Molander et al., *Accounts of Chemical Research* 2007, 40, 275-286. Also, Example 9, Step C illustrates the synthesis of a compound of Formula 6 using the method of Scheme 7.

Scheme 7

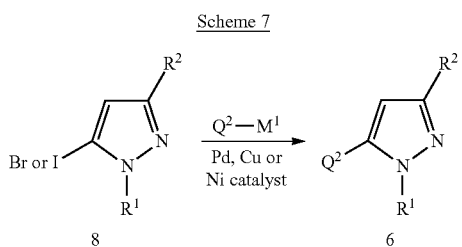

Alternatively, as shown in Scheme 8, compounds of Formula 6 can be prepared by cyclization of enones of Formula 9 with an appropriately substituted hydrazine of formula $NH_2NHR^1$ and subsequent oxidation of pyrazolines of Formula 10. Useful oxidizing reagents include bromine (for conditions see, for example, *Indian Journal of Heterocyclic Chemistry*, 2001, 11(1), 21-26), elemental sulfur, manganese dioxide, 2,3-dichloro-5,6-dicyanobenzoquinone (DDQ), chloranil (for conditions see, for example, *Russian Journal of Organic Chemistry* 2006, 42(8), 1113-1119) and oxygen optionally in the presence of a metal catalyst such as cobalt acetate (for conditions see, for example, *Tetrahedron* 2006, 62(11), 2492-2496, *Chinese Chemical Letters* 2008, 19(9), 1013-1016). Useful solvents for this reaction include N,N-dimethylformamide, tetrahydrofuran, toluene, water, dichloromethane, tetrachloroethane, and mixtures of these or similar solvents, at temperatures from ambient to 200° C. The reaction of hydrazines with enones and the preparation of the enones is well-known in the art (see, for example, *Berichte der Deutschen Chemischen Gesellschaft [Abteilung] B: Abhandlungen* 1925, 58B, 1974-86, and *Journal of the American Chemical Society* 1958, 80, 5524-7). Also, Example 4, Step B illustrates the synthesis of a compound of Formula 6 by the method of Scheme 8.

Scheme 8

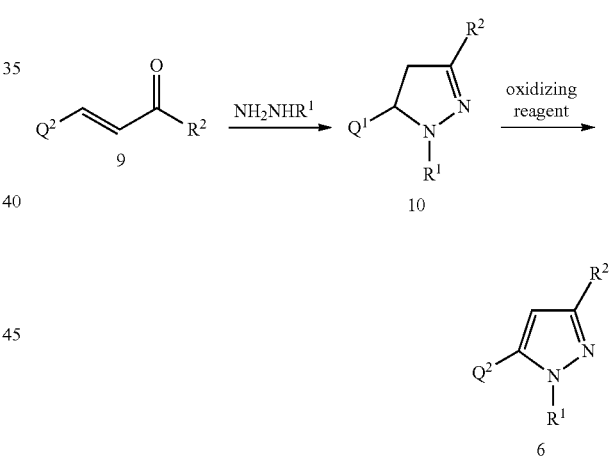

As shown in Scheme 9, compounds of Formula 8 can be prepared by alkylation of the corresponding pyrazole of Formula 11 with an alkylating agent of formula $R^1$-L wherein L is a leaving group such as halogen or (halo)alkylsulfonate (e.g., Cl, Br, I, p-toluenesulfonate, methanesulfonate or trifluoromethanesulfonate). General procedures for alkylations of this type are well-known in the art and can be readily adapted to prepare compounds of the present invention. Particularly useful alkylating agents for preparing compounds of Formula 8 wherein $R^1$ is methyl are diazomethane or iodomethane using general procedures known in the art, such as those described in *Journal of Heterocyclic Chemistry* 1988, 1307-1310. Example 9, Step B illustrates the method of Scheme 9 for the preparation of a compound of Formula 8 wherein $R^1$ is methyl.

Scheme 9

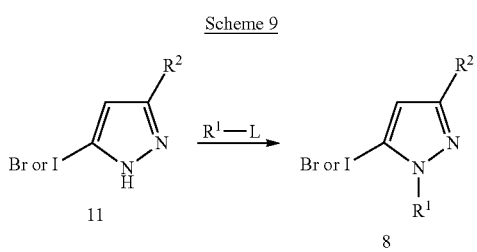

Starting compounds of Formula 11 are known and can be prepared by a variety of methods disclosed in the chemical literature. For a specific example, see Example 9, Step A.

As shown in Scheme 10, Compounds of Formula 1A can also be prepared by the reaction of compounds of Formula 12 (e.g., 4-aminopyrazoles of Formula 12 for X being $N(R^6)$, 4-hydroxypyrazoles (4-pyrazolones) of Formula 12 for X being O, and 4-mercaptopyrazoles of Formula 12 for X being S) with compounds of Formula 13 where L is a leaving group such as halogen or (halo)alkylsulfonate (e.g., Cl, Br, I, p-toluenesulfonate, methanesulfonate or trifluoromethanesulfonate), optionally in the presence of a metal catalyst, and generally in the presence of a base and a polar aprotic solvent such as N,N-dimethylformamide or dimethyl sulfoxide. Compounds of Formula 13 in which $Q^1$ is a phenyl ring substituted with electron-withdrawing substituents react with Formula 12 compounds by direct displacement of the leaving group L from the $Q^1$ ring to provide compounds of Formula 1A. Typically for these types of reactions L is F or Cl. Compounds of Formula 13 wherein $Q^1$ is phenyl not substituted with an electron-withdrawing substituent, or in general, to improve reaction rate, yield or product purity, the use of a metal catalyst (e.g., metal or metal salt) in amounts ranging from catalytic up to superstoichiometric can facilitate the desired reaction. Typically for these conditions, L is Br or I or a sulfonate such as $—OS(O)_2CF_3$ or $—OS(O)_2(CF_2)_3CF_3$. For example, the reaction can be run in the presence of a metal catalyst such as copper salt complexes (e.g., CuI with N,N'-dimethylethylenediamine, proline or bipyridyl), palladium complexes (e.g., tris-(dibenzylideneacetone)dipalladium(0)) or palladium salts (e.g., palladium acetate) with ligands such as 4,5-bis(diphenylphosphino)-9,9-dimethylxanthene, 2-dicyclohexyl-phosphino-2',4',6'-triisopropylbiphenyl or 2,2'-bis(diphenylphosphino)1,1'-binaphthalene, with a base such as potassium carbonate, cesium carbonate, sodium phenoxide or sodium tert-butoxide, in a solvent such as N,N-dimethylformamide, 1,2-dimethoxyethane, dimethyl sulfoxide, 1,4-dioxane or toluene, optionally containing an alcohol such as ethanol. The method of Scheme 10 is illustrated in Example 1, Step C and Example 2, Step G.

Scheme 10

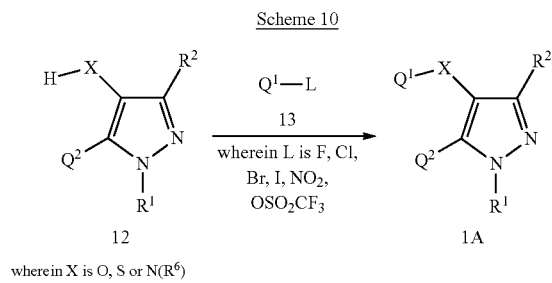

wherein X is O, S or $N(R^6)$

Compounds of Formula 12 are commercially available and their preparation is known in the art; see, for example, *Journal für Praktische Chemie* (*Liepzig*) 1911, 83, 171-182 and *Journal of the American Chemical Society* 1954, 76, 501-503. Also, present Example 1, Steps A through B and Example 2, Steps A through F illustrate methods for preparing 4-aminopyrazoles of Formula 12.

As illustrated in Scheme 11, compounds of Formula 1Ab (i.e. Formula 1A wherein X is NH) can also be prepared by reaction of compounds of Formula 14 with compounds of Formula 15 under metal-catalyzed conditions similar to those described above for Scheme 7.

Scheme 11

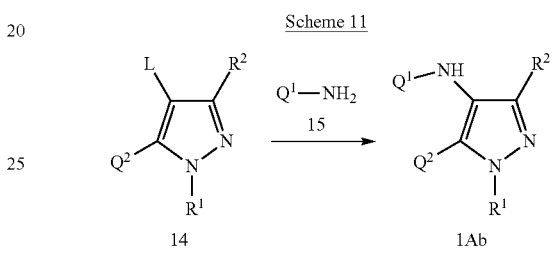

wherein L is Br, I, $OSO_2C_4F_9$, etc.

Compounds of Formula 14 are known and can be prepared by the method disclosed in Scheme 6, and by a variety of methods disclosed in the chemical literature.

As shown in Scheme 12, compounds of Formula 1A can also be prepared by reaction of a 5-bromo or 5-iodo pyrazole of Formula 16 with an organometallic compound of Formula 17 under transition-metal-catalyzed cross-coupling reaction conditions analogous to those described for Scheme 7. Reaction of a pyrazole of Formula 16 with a boronic acid, trialkyltin, zinc or organomagnesium reagent of Formula 16 in the presence of a palladium or nickel catalyst and optionally a ligand (e.g., triphenylphosphine, dibenzylideneacetone, dicyclohexyl(2',6'-dimethoxy[1,1'-biphenyl]-2-yl)phosphine) and a base, if needed, affords the corresponding compound of Formula 1A. For example, a compound of Formula 17 wherein M is $B(OH)_2$, $B(OC(CH_3)_2C(CH_3)_2O))$, $B(O-i-Pr)_3Li$ reacts with a 5-bromo- or 5-iodopyrazole of Formula 16 in the presence of dichlorobis(triphenylphosphine) palladium(II) and aqueous base such as sodium carbonate or potassium hydroxide, in solvents such as 1,4-dioxane, 1,2-dimethoxyethane, toluene or ethyl alcohol, or under anhydrous conditions with the use of a ligand such as phosphine oxide or phosphite ligand (e.g., diphenylphosphine oxide) and potassium fluoride in a solvent such as 1,4-dioxane to provide the corresponding compound of Formula 1A (for references, see *Angewandte Chemie, International Edition* 2008, 47(25), 4695-4698 and *Journal of the American Chemical Society* 2010, 132(40), 14073-14075). The method of Scheme 12 is illustrated in Example 3, Step D.

Scheme 12

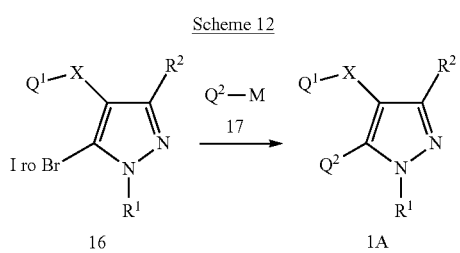

Compounds of Formula 16 can be prepared via halogenation methods analogous to those described for Scheme 6, and illustrated in Example 3, Step C.

It will be recognized by one skilled in the art that various functional groups can be converted into others to provide different compounds of Formula 1 or Formula 1A. For example, compounds of Formula 1 or Formula 1A in which $R^2$ is methyl, ethyl or cyclopropyl can be modified by free-radical halogenation to form compounds of Formula 1 or Formula 1A wherein $R^2$ is halomethyl or halocyclopropyl. The halomethyl compounds can be used as intermediates to prepare compounds of Formula 1 or Formula 1A wherein $R^2$ is hydroxymethyl or cyanomethyl. Compounds of Formula 1, Formula 1A or intermediates for their preparation may contain aromatic nitro groups, which can be reduced to amino groups, and then be converted via reactions well-known in the art, such as the Sandmeyer reaction, to various halides, providing other compounds of Formula 1 or Formula 1A. By similar known reactions, aromatic amines (anilines) can be converted via diazonium salts to phenols, which can then be alkylated to prepare compounds of Formula 1 or Formula 1A with alkoxy substituents. Likewise, aromatic halides such as bromides or iodides prepared via the Sandmeyer reaction can react with alcohols under copper-catalyzed conditions, such as the Ullmann reaction or known modifications thereof, to provide compounds of Formula 1 or Formula 1A that contain alkoxy substituents. Additionally, some halogen groups, such as fluorine or chlorine, can be displaced with alcohols under basic conditions to provide compounds of Formula 1 or Formula 1A containing the corresponding alkoxy substituents. The resultant alkoxy compounds can themselves be used in further reactions to prepare compounds of Formula 1 or Formula 1A wherein $R^{3a}$ is —U—V-T (see, for example, PCT Publication WO 2007/149448 A2). Compounds of Formula 1, Formula 1A or precursors thereof in which $R^2$ is halide, preferably bromide or iodide, are particularly useful intermediates for transition metal-catalyzed cross-coupling reactions to prepare compounds of Formula 1 or Formula 1A. These types of reactions are well documented in the literature; see, for example, Tsuji in *Transition Metal Reagents and Catalysts: Innovations in Organic Synthesis*, John Wiley and Sons, Chichester, 2002; Tsuji in *Palladium in Organic Synthesis*, Springer, 2005; and Miyaura and Buchwald in *Cross Coupling Reactions: A Practical Guide*, 2002; and references cited therein.

It is recognized that some reagents and reaction conditions described above for preparing compounds of Formula 1 or Formula 1A may not be compatible with certain functionalities present in the intermediates. In these instances, the incorporation of protection/deprotection sequences or functional group interconversions into the synthesis will aid in obtaining the desired products. The use and choice of the protecting groups will be apparent to one skilled in chemical synthesis (see, for example, Greene, T. W.; Wuts, P. G. M. *Protective Groups in Organic Synthesis*, 2nd ed.; Wiley: New York, 1991). One skilled in the art will recognize that, in some cases, after the introduction of a given reagent as it is depicted in any individual scheme, it may be necessary to perform additional routine synthetic steps not described in detail to complete the synthesis of compounds of Formula 1 and Formula 1A. One skilled in the art will also recognize that it may be necessary to perform a combination of the steps illustrated in the above schemes in an order other than that implied by the particular sequence presented to prepare the compounds of Formula 1 and or Formula 1A.

One skilled in the art will also recognize that compounds of Formula 1, Formula 1A and the intermediates described herein can be subjected to various electrophilic, nucleophilic, radical, organometallic, oxidation, and reduction reactions to add substituents or modify existing substituents.

Without further elaboration, it is believed that one skilled in the art using the preceding description can utilize the present invention to its fullest extent. The following Examples are, therefore, to be construed as merely illustrative, and not limiting of the disclosure in any way whatsoever. Steps in the following Examples illustrate a procedure for each step in an overall synthetic transformation, and the starting material for each step may not have necessarily been prepared by a particular preparative run whose procedure is described in other Examples or Steps. Percentages are by weight except for chromatographic solvent mixtures or where otherwise indicated. Parts and percentages for chromatographic solvent mixtures are by volume unless otherwise indicated. MPLC refers to medium pressure liquid chromatography on silica gel. $^1$H NMR spectra are reported in ppm downfield from tetramethylsilane; "s" means singlet, "d" means doublet, "t" means triplet, "m" means multiplet, "dd" means doublet of doublets, "dt" means doublet of triplets and "br s" means broad singlet.

Example 1

Preparation of 4-[[5-(2-chloro-4-fluorophenyl)-1,3-dimethyl-1H-pyrazol-4-yl]amino]-3,5-difluorobenzonitrile (Compound 40)

Step A: Preparation of 5-(2-chloro-4-fluorophenyl)-1,3-dimethyl-4-nitro-1H-pyrazole A mixture of 5-chloro-1,3-dimethyl-4-nitro-1H-pyrazole (2.50 g, 14.3 mmol), 2-chloro-4-fluorophenylboronic acid (2.98 g, 17.2 mmol), cesium carbonate (5.58 g, 17.2 mmol) and dichloro[1,1'-bis(diphenylphosphino)ferrocene]palladium(II) dichloro-methane complex (1:1) (1.16 g, 1.43 mmol) in dioxane (50 mL) was heated at 100° C. for approximately 2.5 days. After cooling to room temperature, the reaction mixture was filtered through a pad of Celite® (diatomaceous earth) on a sintered glass frit funnel and the filtrate was concentrated under reduced pressure. The resulting material was dissolved in ethyl acetate and filtered through a plug of silica on a sintered glass frit funnel and the filtrate was concentrated under reduced pressure. The resulting material was purified by silica gel column chromatography (5 to 40% gradient of ethyl acetate in hexanes as eluant) to provide the title compound (0.32 g).

$^1$H NMR (CDCl$_3$): δ 7.32-7.26 (m, 2H), 7.16-7.09 (m, 1H), 3.58 (s, 3H), 2.57 (s, 3H).

Step B: Preparation of 5-(2-chloro-4-fluorophenyl)-1,3-dimethyl-1H-pyrazol-4-amine A mixture of 5-(2-chloro-4-fluorophenyl)-1,3-dimethyl-4-nitro-1H-pyrazole (i.e. the product of Step A) (0.2 g, 0.74 mmol), iron powder (0.2 g, 3.6 mmol) and saturated aqueous ammonium chloride solution (1 mL) in ethanol (5 mL) was heated at 80° C. for 4 h. After cooling to room temperature, the reaction mixture was diluted with ethyl acetate and filtered through a pad of Celite® (diatomaceous earth) on a sintered glass frit funnel. The filtrate was concentrated under reduced pressure and the resulting material was purified by silica gel column chromatography (ethyl acetate as eluant) to provide the title compound (0.14 g).

$^1$H NMR (CDCl$_3$): δ 7.36-7.20 (m, 2H), 7.17-7.05 (m, 1H), 3.57 (s, 3H), 2.66 (br s, 2H), 2.24 (s, 3H).

Step C: Preparation of 4-[[5-(2-chloro-4-fluorophenyl)-1,3-dimethyl-1H-pyrazol-4-yl]amino]-3,5-difluorobenzonitrile A mixture of 5-(2-chloro-4-fluorophenyl)-1,3-dimethyl-1H-pyrazol-4-amin (i.e. the product of Step B) (0.25 g, 1.0 mmol), 3,4,5-trifluorobenzonitrile (0.188 g, 1.2 mmol) and cesium carbonate (0.390 g, 1.2 mmol) in acetonitrile (3 mL) was heated at 210° C. in a Biotage Initiator™ microwave apparatus for 2 h. After cooling to room temperature, the reaction mixture was diluted with ethyl acetate and filtered through a pad of silica gel on a sintered glass frit funnel. The filtrate was concentrated under reduced pressure and the resulting material was purified by silica gel chromatography (30% ethyl acetate in hexanes as eluant) to provide the title compound, a compound of the present invention, as a solid (0.065 g).

$^1$H NMR (CDCl$_3$): δ 7.34-7.16 (m, 2H), 7.04 (m, 3H), 5.27 (br s, 1H), 3.64 (s, 3H), 2.18 (s, 3H).

Example 2

Preparation of 4-(4-chloro-2-fluorophenyl)-5-(2-chloro-4-fluorophenyl)-1,3-dimethyl-1H-pyrazol-4-amine (Compound 45)

Step A: Preparation of methyl 3-(methylamino)-2-butenoate

To a mixture of methyl acetoacetate (23.2 g, 0.2 mol) in water (15 mL) at 10° C. was added dropwise methylamine (40% aqueous solution, 18.6 g, 0.24 mol). The reaction mixture was allowed to warm to room temperature and stirred for 2 h. The resulting solid precipitate was collected by filtration and washed with ice water (2×), and then dried in a vacuum oven at 55° C. overnight to provide the title compound as a white solid (20.9 g).

$^1$H NMR (CDCl$_3$): δ 8.45 (br s, 1H, NH), 4.47 (s, 1H), 3.62 (s, 3H), 2.91 (d, 3H), 1.92 (s, 3H).

Step B: Preparation of methyl 2-chloro-4-fluoro-α-[1-(methylamino)ethylidene]-β-oxobenzenepropanoate To a mixture of methyl 3-(methylamino)-2-butenoate (i.e. the product of Step A) (10.25 g, 79.43 mmol) and triethylamine (13.26 mL, 9.63 g, 95.31 mmol) in toluene (125 mL) at 0° C. was added dropwise 2-chloro-4-fluorobenzoyl chloride (15.25 g, 79.48 mol) in toluene (25 mL) over 30 minutes while maintaining the temperature of the reaction mixture between about 0 to 5° C. The reaction mixture was allowed to warm to room temperature and stirred over night. The reaction mixture was filtered and the filtrate was concentrated under reduced pressure. The resulting dark yellow oil was triturated with hexanes and filtered to provide the title compound as a white solid (15.91 g).

$^1$H NMR (CDCl$_3$): δ 12.60 (s, 1H), 7.20-6.90 (m, 3H), 3.30 (s, 3H), 3.11 (s, 3H), 2.35 (s, 3H).

Step C: Preparation of methyl 5-(2-chloro-4-fluorophenyl)-1,3-dimethyl-1H-pyrazole-4-carboxylate A mixture of methyl 2-chloro-4-fluoro-α-[1-(methylamino)ethylidene]-β-oxobenzenepropanoate (i.e. the product of Step B) (15.91 g, 55.82 mmol) and methylhydrazine (3 mL, 56 mmol) in diethyl ether (150 mL) was stirred at room temperature for 48 h. The reaction mixture was concentrated under reduced pressure to provide the title compound as a colorless oil (15 g).

$^1$H NMR (CDCl$_3$): δ 7.32-7.25 (m, 2H), 7.10 (dt, 1H), 3.59 (s, 3H), 2.64 (s, 3H), 2.51 (s, 3H).

Step D: Preparation of 5-(2-chloro-4-fluorophenyl)-1,3-dimethyl-1H-pyrazole-4-carboxylic acid A mixture of methyl 5-(2-chloro-4-fluorophenyl)-1,3-dimethyl-1H-pyrazole-4-carboxylate (i.e. the product of Step C) (12.33 g, 43.7 mol) and sodium hydroxide (1 N, 70 mL) in methanol (70 mL) was heated at reflux for 2 h. The reaction mixture was cooled to about 0° C., and then the pH of the reaction mixture was adjusted to 3 by the addition of aqueous hydrochloric acid solution (1 N). The reaction mixture was extracted with ethyl acetate (3×70 mL) and the combined extracts were washed with saturated aqueous sodium chloride solution, dried over magnesium sulfate and filtered. The filtrate was concentrated under reduced pressure to provide the title compound as a white solid (11.14 g).

$^1$H NMR (CDCl$_3$): δ 12.00 (br s, 1H), 7.70-7.45 (m, 2H), 7.35 (dt, 1H), 3.48 (s, 3H), 2.37 (s, 3H).

Step E: Preparation of methyl N-[5-(2-chloro-4-fluorophenyl)-1,3-dimethyl-1H-pyrazol-4-yl]carbamate A mixture of 5-(2-chloro-4-fluorophenyl)-1,3-dimethyl-1H-pyrazole-4-carboxylic acid (i.e. the product of Step D) (10.14 g, 37.8 mmol), diphenyl phosphoryl azide (8.15 mL, 10.4 g, 37.8 mmol) and triethylamine (6.32 mL, 4.59 g, 45.4 mmol) in toluene (100 mL) was stirred at room temperature for 2 h. After 2 h, the reaction mixture was added dropwise to toluene (100 mL) and heated at reflux for 2 h. The reaction mixture was cooled to about 70° C., methanol (30 mL) was added dropwise, and the mixture was again heated at reflux for an additional 40 minutes. The reaction mixture was diluted with water (100 mL), extracted with ethyl acetate (2×40 mL) and the combined extracts were washed with saturated aqueous sodium chloride solution, dried over magnesium sulfate and filtered. The filtrate was concentrated under reduced pressure to provide the title compound as a light yellow solid (9.77 g).

$^1$H NMR (CDCl$_3$): δ 7.42-7.26 (m, 2H), 7.08 (dt, 1H), 5.68 (br s, 1H, NH), 3.66 (br s, 3H), 3.62 (s, 3H), 2.24 (s, 3H).

Step F: Preparation of 5-(2-chloro-4-fluorophenyl)-1,3-dimethyl-1H-pyrazol-4-amine A mixture of N-[5-(2-chloro-4-fluorophenyl)-1,3-dimethyl-1H-pyrazol-4-yl]carbamate (i.e. the product of Step E) (7.07 g, 23.8 mmol) and aqueous sodium hydroxide (1 N, 70 mL) in methanol (70 mL) was heated at reflux for 20 h. The reaction mixture was concentrated under reduced pressure, diluted with water and extracted with ethyl acetate (2×30 mL). The combined organic layers were extracted with hydrochloric acid (1 N, 2×30 mL), and the pH of the combined aqueous extracts was adjusted to 10 with the addition of sodium hydroxide (1 N). The aqueous mixture was extracted with ethyl acetate (2×40 mL). The combined organic extracts were washed with saturated aqueous sodium chloride solution, dried over magnesium sulfate, filtered and concentrated under reduced pressure to provide the title compound as a viscous yellow oil (4.36 g).

$^1$H NMR (CDCl$_3$): δ 7.35-7.28 (m, 2H), 7.11 (m, 1H), 3.57 (s, 3H), 2.60 (br s, 2H, NH$_2$), 2.23 (s, 3H).

Step G: Preparation of 4-(4-chloro-2-fluorophenyl)-5-(2-chloro-4-fluorophenyl)-1,3-dimethyl-1H-pyrazol-4-amine A mixture of 5-(2-chloro-4-fluorophenyl)-1,3-dimethyl-1H-pyrazol-4-amine (i.e. the product of Step F) (7.07 g, 23.8 mmol), 4-chloro-2-fluoroiodobenzene (256 μL, 2.0 mmol), sodium tert-butoxide (0.192 g, 2.0 mmol) and [1,1'-bis(diphenylphosphino)ferrocene]-dichloropalladium(II) (0.117 g, 0.16 mmol) in toluene (5 mL) was heated at 180° C. in a Biotage Initiator™ microwave apparatus for 1 h. The resulting material was purified by flash chromatography on a silica gel (40 g), Varian Bond Elute SI® column (30% ethyl acetate in hexanes as eluant) to provide the title compound, a compound of the present invention, as a dark purple/brown oil (164 mg).

$^1$H NMR (CDCl$_3$): δ 7.26-7.15 (m, 2H), 7.03-6.95 (m, 2H), 6.75 (dt, 1H), 6.45-6.40 (m, 1H), 5.20 (s, 1H, NH), 3.67 (s, 3H), 2.13 (s, 3H).

Example 3

Preparation of 4-(2-chloro-4-fluorophenoxy)-5-(2,4-difluorophenyl)-1,3-dimethyl-1H-pyrazole (Compound 5)

Step A: Preparation of 1-(2-chloro-4-fluorophenoxy)-2-propanone

A mixture of 2-chloro-4-fluorophenol (3.00 g, 20.4 mmol), chloroacetone (2.12 mL, 26.6 mmol), potassium carbonate (4.24 g, 30.7 mmol) and potassium iodide (0.20 g, catalytic) in acetone (30 mL) was heated at reflux for 4 h, cooled and filtered. The filtrate was concentrated under reduced pressure to provide the title compound as a yellow solid (4.05 g).

$^1$H NMR (CDCl$_3$): δ 7.16 (dd, J=8.0, 3.0 Hz, 1H), 6.93 (m, 1H), 6.76 (m, 1H), 4.53 (s, 2H), 2.34 (s, 3H).

Step B: Preparation of 4-(2-chloro-4-fluorophenoxy)-1,3-dimethyl-1H-pyrazole

A mixture of 1-(2-chloro-4-fluorophenoxy)-2-propanone (i.e. the product of Step A) (1.40 g, 6.93 mmol) and N,N-dimethylformamide dimethyl acetal (1.38 mL, 10.4 mmol) was heated to 90° C. for 3 h, and then concentrated under reduced pressure. The resulting material was diluted with ethanol (15 mL), and then methylhydrazine (0.49 mL, 9.0 mmol) and acetic acid (0.1 mL) were added. After 15 h, the reaction mixture was concentrated under reduced pressure and the resulting material was purified by silica gel column chromatography (5 to 40% gradient of ethyl acetate in hexanes as eluant) to provide the title compound as a brown yellow oil (680 mg).

$^1$H NMR (CDCl$_3$): δ 7.16 (m, 2H), 6.78-6.88 (m, 2H), 3.81 (s, 3H), 2.10 (s, 3H).

Step C: Preparation of 5-bromo-4-(2-chloro-4-fluorophenoxy)-1,3-dimethyl-1H-pyrazole To a mixture of 4-(2-chloro-4-fluorophenyoxy)-1,3-dimethyl-1H-pyrazole (i.e. the product of Step B) (680 mg, 2.82 mmol) and sodium carbonate (389 mg, 3.67 mmol) in dichloromethane (12 mL) at −40° C. was added a solution of bromine (474 mg, 2.96 mmol) in dichloromethane (1 mL). After the addition was complete, the reaction mixture temperature was maintained at about −30 to −20° C. for 5 h. The reaction mixture was diluted with dichloromethane (50 mL) and washed with water (2×10 mL), aqueous sodium chloride solution, dried over sodium sulfate, filtered and concentrated under reduced pressure to provide the title compound as a yellow solid (720 mg).

$^1$H NMR (CDCl$_3$): δ 7.18 (dd, J=8.0, 3.0 Hz, 1H), 6.87 (m, 1H), 6.67 (m, 1H), 3.82 (s, 3H), 2.10 (s, 3H).

Step D: Preparation of 4-(2-chloro-4-fluorophenoxy)-5-(2,4-difluorophenyl)-1,3-dimethyl-1H-pyrazole A mixture of 5-bromo-4-(2-chloro-4-fluorophenoxy)-1,3-dimethyl-1H-pyrazole (i.e. the product of Step C) (250 mg, 0.78 mmol) in 1,2-dimethoxyethane/water (5 mL, 2:1) was sparged with a subsurface stream of argon for 30 minutes, and then 2,4-difluorophenylboronic acid (371 mg, 2.34 mmol), potassium carbonate (1.08 g, 7.82 mmol) and tetrakis(triphenylphosphine)palladium (90 mg, 0.078 mmol) were added. The reaction mixture was heated to 80° C. for 15 h, and then cooled and extracted with ethyl acetate. The organic layer was washed with water and saturated aqueous sodium chloride solution, dried over sodium sulfate, filtered and concentrated under reduced pressure. The resulting material was purified by silica gel column chromatography (5 to 30% gradient of ethyl acetate in hexanes as eluant) to provide the title compound, a compound of the present invention, as a pale yellow solid (150 mg) melting at 70-72° C.

$^1$H NMR (CDCl$_3$): δ 7.27 (m, 1H), 7.07 (dd, J=8.0, 3.0 Hz, 1H), 6.90 (m, 2H), 6.79 (m, 1H), 6.69 (m, 1H), 3.71 (s, 3H), 2.12 (s, 3H).

Example 4

Preparation of α-(2,4-difluorophenyl)-5-(2,6-difluorophenyl)-1,3-dimethyl-1H-pyrazole-4-methanol (Compound 14)

Step A: Preparation of 4-(2,6-difluorophenyl)-3-buten-2-one

To a mixture of 2,6-difluorobenzaldehyde (10.0 g, 70 mmol) in acetone (85 mL) was added sodium hydroxide (1 N solution, 106 mL). After stirring at room temperature for 1.5 h, the reaction mixture was diluted with saturated aqueous sodium chloride solution and extracted with chloroform (2×150 mL). The combined organic layers were dried over magnesium sulfate, filtered and concentrated under reduced pressure. The resulting material was purified by MPLC (0 to 20% gradient of ethyl acetate in hexanes as eluant) to afford the title product as a solid (8.1 g).

$^1$H NMR (CDCl$_3$): δ 7.61 (d, 1H), 7.16 (m, 1H), 6.98 (m, 3H), 2.39 (s, 3H).

Step B: Preparation of 5-(2,6-difluorophenyl)-1,3-dimethyl-1H-pyrazole

To a mixture of 4-(2,6-difluorophenyl)-3-buten-2-one (i.e. the product of Step A) (8.1 g, 44.5 mmol) in ethanol (50 mL) was added methylhydrazine (2.1 g, 49 mmol). After 24 h, the reaction mixture was concentrated under reduced pressure. To the resulting oil (10.1 g) was added 1,1,2,2-tetrachloroethane (65 mL) and manganese oxide (41.7 g, 480 mmol). The reaction mixture was heated at 140° C. for 20 minutes, and then cooled to room temperature and filtered through a pad of Celite® (diatomaceous earth) on a sintered glass frit funnel rinsing with dichloromethane (2×20 mL). The filtrate was concentrated under reduced pressure and the resulting material was purified by MPLC (10 to 50% gradient of ethyl acetate in hexanes as eluant) to provide the title compound as a light yellow solid (4.02 g).

$^1$H NMR (CDCl$_3$): δ 7.38 (m, 1H), 7.01 (m, 2H), 6.17 (s, 1H), 3.71 (s, 3H), 2.32 (s, 3H).

Step C: Preparation of 4-bromo-5-(2,6-difluorophenyl)-1,3-dimethyl-1H-pyrazole To a mixture of 5-(2,6-difluorophenyl)-1,3-dimethyl-1H-pyrazole (i.e. the product of Step B) (1.53 g, 7.3 mmol) in N,N-dimethylformamide (20 mL) at 0° C. was added portionwise N-bromosuccinimide (1.37 g, 7.7 mmol). After the addition was complete, the reaction mixture was allowed to warm to room temperature and stirred for 1 h. The reaction mixture was diluted with ice water (20 mL) and saturated aqueous sodium bisulfite solution (15 mL), briefly stirred, and then partitioned between water (75 mL) and ethyl acetate (100 mL). The layers were separated and the aqueous layer was extracted with ethyl acetate (100 mL). The combined organic layers were washed with saturated aqueous sodium chloride solution (100 mL), dried over magnesium sulfate, filtered and concentrated under reduced pressure. The resulting material was purified by MPLC (10 to 40% gradient of ethyl acetate in hexanes as eluant) to provide the title compound as a solid (1.84 g).

$^1$H NMR (CDCl$_3$): δ 7.52-7.42 (m, 1H), 7.10-7.01 (m, 2H), 3.71 (s, 3H), 2.30 (s, 3H).

Step D: Preparation of α-(2,4-difluorophenyl)-5-(2,6-difluorophenyl)-1,3-dimethyl-1H-pyrazole-4-methanol To a mixture of 4-bromo-5-(2,6-difluorophenyl)-1,3-dimethyl-1H-pyrazole (i.e. the product of Step C) (500 mg, 1.7 mmol) in tetrahydrofuran (15 mL) at −78° C. was added dropwise n-butyllithium (2.0 M in hexanes, 0.76 mL, 1.9 mmol). The reaction mixture was stirred at −78° C. for about 20 minutes, and then a solution of 2,4-difluorobenzaldehyde (153 µL, 1.4 mmol) in tetrahydrofuran (1 mL) was added dropwise. After the addition was complete, the reaction mixture was stirred at about −78° C. for about 15 minutes, and then diluted with saturated aqueous ammonium chloride solution (1 mL) and allowed to warm to room temperature. The resulting mixture was poured onto a solid phase extraction tube (Varian Chem Elute®, prepacked with diatomaceous earth) eluting with ethyl acetate (50 mL). The ethyl acetate eluant was concentrated under reduced pressure and the resulting material was purified by MPLC (20 to 50% gradient of ethyl acetate in hexanes as eluant) to provide the title compound, a compound of the present invention, as a solid (560 mg).

$^1$H NMR (CDCl$_3$): δ 7.41-7.32 (m, 2H), 7.01-6.90 (m, 1H), 6.89-6.82 (m, 1H), 6.68-6.56 (m, 2H), 5.82 (d, 1H), 3.60 (s, 3H), 2.26 (s, 3H), 2.08 (br s, 1H).

Example 5

Preparation of 5-(2,6-difluorophenyl)-4-[(2,4-difluorophenyl)fluoromethyl]-1,3-dimethyl-1H-pyrazole (Compound 68)

To a mixture of α-(2,4-difluorophenyl)-5-(2,6-difluorophenyl)-1,3-dimethyl-1H-pyrazole-4-methanol (i.e. the product of Example 4) (70 mg, 0.20 mmol) in dichloromethane (2 mL) at −78° C. was added bis(2-methoxyethyl)aminosulfur trifluoride (Deoxo-Fluor®) (40 µL, 0.24 mmol). The reaction mixture was stirred overnight at room temperature, and then cooled to −78° C. and saturated aqueous sodium bicarbonate solution (3 mL) was added dropwise. The resulting mixture was extracted with dichloromethane (3×) and the combined organic layers were dried over magnesium sulfate, filtered and concentrated under reduced pressure. The resulting material was purified by MPLC (50% ethyl acetate in hexanes as eluant) to provide the title compound, a compound of the present invention, as a solid (30 mg)

$^1$H NMR (CDCl$_3$): δ 7.40-7.31 (m, 1H), 7.28-7.20 (m, 1H), 6.98-6.82 (m, 2H), 6.70-6.62 (m, 2H), 6.52 (d, 1H), 3.61 (s, 3H), 2.20 (s, 3H).

Example 6

Preparation of 4-[(4-chlorophenyl)thio]-5-(2,6-difluorophenyl)-1,3-dimethyl-1H-pyrazole (Compound 56)

To a mixture of 4-bromo-5-(2,6-difluorophenyl)-1,3-dimethyl-1H-pyrazole (i.e. the product of Step C, Example 4) (250 mg, 0.87 mmol) in tetrahydrofuran at −78° C. was added dropwise n-butyllithium (2.5 M in hexanes, 0.38 ml, 0.96 mmol). The reaction mixture was stirred at about −78 to 0° C. for 15 minutes, and then 4,4'-dichlorodiphenyl disulfide (0.25 g, 0.87 mmol) in tetrahydrofuran (1 mL) was added. After about 10 minutes, the reaction mixture was diluted with saturated aqueous ammonium chloride solution and allowed to warm to room temperature. The resulting mixture was poured onto a solid phase extraction tube (Varian Chem Elute®, prepacked with diatomaceous earth) eluting with ethyl acetate. The ethyl acetate eluant was concentrated under reduced pressure and the resulting material was purified by MPLC (10 to 50% gradient of ethyl acetate in hexanes as eluant) to provide the title compound, a compound of the present invention, as an oil (130 mg).

$^1$H NMR (CDCl$_3$): δ 7.45-7.38 (m, 1H), 7.15-7.10 (d, 2H), 7.01-6.92 (m, 2H), 6.93-6.85 (d, 2H), 3.75 (s, 3H), 2.22 (s, 3H).

Example 7

Preparation of (2,4-difluorophenyl)-[5-(2,4-difluorophenyl)-1,3-dimethyl-1H-pyrazol-4-yl]methanone (Compound 32)

To a mixture of aluminum chloride (380 mg, 2.88 mmol) in tetrachloroethane (10 mL) at about 0° C. was added 2,4-difluorobenzoyl chloride (0.36 mL, 2.88 mmol). The reaction mixture was stirred for about 30 minutes, and then a mixture of 5-(2,4-difluorophenyl)-1,3-dimethyl-1H-pyrazole (prepared by the method analogous to Example 4, Steps A-B starting with 2,4-difluorobenzaldehyde) in tetrachloroethane (0.5 mL) was added. The reaction mixture was allowed to warm to room temperature, stirred for 1 h, and then heated at reflux for 24 h. The reaction mixture was cooled to room temperature, poured over a mixture of ice/hydrochloric acid and extracted with dichloromethane (3×). The combined organic layers were washed with saturated sodium chloride solution, dried over magnesium sulfate, filtered and concentrated under reduced pressure. The resulting material was purified by MPLC (50% ethyl acetate in hexanes as eluant) to provide the title compound, a compound of the present invention, as a solid (0.16 g).
$^1$H NMR (CDCl$_3$) δ 7.28-7.38 (m, 1H), 7.08-7.01 (m, 1H), 6.79-6.70 (m, 3H), 6.50-6.42 (m, 1H), 3.67 (s, 3H), 2.48 (s, 3H).

Example 8

Preparation of α-(2,4-difluorophenyl)-5-(2,4-difluorophenyl)-1,3-dimethyl-1H-pyrazole-4-methanol (Compound 72)

To a mixture of (2,4-difluorophenyl)-[5-(2,4-difluorophenyl)-1,3-dimethyl-1H-pyrazol-4-yl]methanone (i.e. the product of Example 7) (80 mg, 0.23 mmol) in ethanol (3 mL) at about 0° C. was added sodium borohydride (38 mg, 0.92 mmol). The reaction mixture was stirred at room temperature for 2 h, and then diluted with ice/hydrochloric acid (about 1 mL). The resulting mixture was poured onto a solid phase extraction tube (Varian Chem Elute®, prepacked with diatomaceous earth) eluting with ethyl acetate (75 mL). The ethyl acetate eluant was concentrated under reduced pressure and the resulting material was purified by MPLC (20 to 70% gradient of ethyl acetate in hexanes as eluant) to provide the title compound, a compound of the present invention, as a solid (63 mg).
$^1$H NMR (CD$_3$OD): δ 8.01-6.62 (m, 6H), 5.85 and 5.71 (two s, 1H) 3.54 and 3.50 (two s, 3H), 2.26 and 2.13 (two s, 3H).

Example 9

Preparation of 3-bromo-5-(2-chloro-4-fluorophenyl)-α-(2,4-difluorophenyl)-1-methyl-1H-pyrazole-4-methanol (Compound 30)

Step A: Preparation of 3,5-dibromo-1H-pyrazole

To mixture of 3,4,5-tribromo-1H-pyrazole (10.0 g, 32.8 mmol) in tetrahydrofuran (130 mL) at −70° C. under an atmosphere of argon was added n-butyllithium (28.8 mL, 72.1 mmol, 2.5 M in hexanes) over 20 minutes. The reaction mixture was stirred at −70° C. for 2 h, and then methanol/tetrahydrofuran (20 mL/30 mL) was added dropwise. The reaction mixture was allowed to warm to room temperature and concentrated under reduced pressure. The resulting material was diluted with diethyl ether (500 mL), washed with aqueous hydrochloric acid (1 N, 25 mL) and saturated aqueous sodium chloride solution (20 mL), dried over sodium sulfate, filtered and concentrated under reduced pressure to provide the title compound as a yellow solid (6.20 g)
$^1$H NMR (DMSO-d$_6$): δ 6.23 (s, 1H).

Step B: Preparation of 3,5-dibromo-1-methyl-1H-pyrazole

To a mixture of sodium hydride (2.74 g 60% in mineral oil, 68.6 mmol) in tetrahydrofuran (40 mL) at 0° C. was added 3,5-dibromo-1H-pyrazole (i.e. the product of Step A) (6.20 g, 27.4 mmol) in tetrahydrofuran (25 mL) over a period of 10 minutes. The reaction mixture was stirred for 1 h at 0° C., and then iodomethane (3.42 mL, 54.9 mmol) was added dropwise. After 3 h the reaction mixture was allowed to warm to room temperature, saturated aqueous ammonium chloride solution (10 mL) was added and the resulting mixture was extracted with ethyl acetate (2×100 mL). The combined organic layers were washed with water and with saturated aqueous sodium chloride solution, dried over sodium sulfate, filtered and concentrated under reduced pressure to provide the title compound as a brownish-yellow solid (6.0 g)
$^1$H NMR (CDCl$_3$): δ 6.29 (s, 1H), 3.85 (s, 3H).

Step C: Preparation of 3-bromo-5-(2-chloro-4-fluorophenyl)-1-methyl-1H-pyrazole

A mixture of 3,5-dibromo-1-methyl-1H-pyrazole (i.e. the product of Step B) (2.00 g, 8.33 mmol) in toluene (40 mL) was sparged with a stream of argon for 45 minutes, and then 2-chloro-4-fluorophenylboronic acid (1.59 g, 9.11 mmol), potassium phosphate tribasic (5.30 g, 25.0 mmol) and tetrakis (triphenylphosphine)palladium(0) (0.48 g, 0.41 mmol) were added. The reaction mixture was heated at 90° C. for 3 h, and then cooled to room temperature and diluted with ethyl acetate (250 mL). The mixture was washed with water (25 mL) and saturated aqueous sodium chloride solution, dried over sodium sulfate, filtered and concentrated under reduced pressure. The resulting material was purified by silica gel chromatography (5 to 40% gradient of ethyl acetate in hexanes as eluant) to provide the title compound as a white solid (620 mg).
$^1$H NMR (CDCl$_3$): δ 7.32-7.27 (m, 2H), 7.09 (m, 1H), 6.28 (s, 1H), 3.67 (s, 3H).

Step D: Preparation of 3-bromo-5-(2-chloro-4-fluorophenyl)-4-iodo-1-methyl-1H-pyrazole To a mixture of 3-bromo-5-(2-chloro-4-fluorophenyl)-1-methyl-1H-pyrazole (i.e. the product of Step C) (620 mg, 2.14 mmol) in N,N-dimethylformamide (8 mL) at 60° C. was added N-iodosuccinimide (963 mg, 4.28 mmol). The reaction mixture was stirred at 60° C. for 3 h, and then diluted with ethyl acetate, washed with water and saturated aqueous sodium chloride solution, dried over sodium sulfate and concentrated under reduced pressure. The material was purified by silica gel chromatography (5 to 30% gradient of ethyl acetate in hexanes as eluant) to provide the title compound as a pale yellow solid (515 mg) melting at 139-141° C.
$^1$H NMR (CDCl$_3$): δ 7.30 (m, 2H), 7.15 (m, 2H), 3.72 (s, 3H).

Step E: Preparation of 3-bromo-5-(2-chloro-4-fluorophenyl)-α-(2,4-difluorophenyl)-1-methyl-1H-pyrazole-4-methanol To a mixture of 3-bromo-5-(2-chloro-4-fluorophenyl)-4-iodo-1-methyl-1H-pyrazole (i.e. the product of Step D) (250 mg, 0.602 mmol) in tetrahydrofuran (3 mL) at −78° C. was added dropwise n-butyllithium (2.5 M solution in hexanes, 0.36 mL, 0.90 mmol). Stirring was continued for 1 h at −78 to −40° C., and then the reaction mixture was cooled to −78° C. and 2,4-difluorobenzaldehyde (103 mg, 0.72 mmol) in tetrahydrofuran (2 mL) was added dropwise. The reaction mixture was allowed to warm to room temperature and stirred for 3 h, and then saturated aqueous ammonium chloride solution was added and the mixture was extracted with ethyl acetate (2×20 mL). The combined organic layers were washed with water and saturated aqueous sodium chloride solution, dried over sodium sulfate and concentrated under reduced pressure. The resulting material was purified by silica gel chromatography (10 to 50% gradient of ethyl acetate in hexanes as eluant) to provide the title compound, a compound of the present invention, as an off-white solid (35 mg).

$^1$H NMR (CDCl$_3$): δ 7.22 (m, 2H), 6.87 (m, 1H), 6.77 (m, 1H), 6.63 (m, 2H), 5.90 (d, J=4.7 Hz, 1H), 3.53 (s, 3H), 2.17 (d, J=4.7 Hz, 1H).

Example 10

Preparation of 4-(2-chloro-4-fluorobenzoyl)-5-(2,6-difluorophenyl)-1-methyl-1H-pyrazole-3-carbonitrile (Compound 52)

Step A: Preparation of ethyl 5-(2,6-difluorophenyl)-1-methyl-1H-pyrazole-3-carboxylate To a mixture of 2,6-difluoroacetophenone (4.7 g, 0.03 mol) and 1,2-diethyl ethanedioate (4.8 g, 0.033 mol) in ethanol (33 mL) was added sodium tert-butoxide (3.17 g, 0.033 mol). After 1 h, more ethanol (30 mL) was added to the reaction mixture and stirring was continued for 1 h. The reaction mixture was partitioned between hydrochloric acid (1 N) and diethyl ether. The organic phase was separated, dried over magnesium sulfate, filtered, and concentrated under reduced pressure to half its original volume. To the resulting mixture was added methylhydrazine (1.52 g, 0.033 mol) and stirring was continued overnight. The reaction mixture was concentrated under reduced pressure and the resulting material was purified by silica gel chromatography (5 to 20% gradient of ethyl acetate in methylene chloride as eluant) to provide the title compound as a solid (1.0 g).

$^1$H NMR (CDCl$_3$): δ 7.56-7.38 (m, 1H) 7.06 (m, 2H) 6.95 (s, 1H), 4.43 (d, 2H) 3.86 (s, 3H), 1.42 (t, 3H).

Step B: Preparation of 5-(2,6-difluorophenyl)-1-methyl-1H-pyrazole-3-carbonitrile To a mixture of ammonium chloride (0.42 g, 7.52 mmol) in toluene (10 mL) at 0° C. was added dropwise trimethyl aluminum (2 M in toluene, 3.76 mL, 7.52 mmol). After the addition was complete, the reaction mixture was stirred at 0° C. for 1 h, warmed to room temperature, and then a mixture of ethyl 5-(2,6-difluorophenyl)-1-methyl-1H-pyrazole-3-carboxylate (i.e. the product of Step A) (1 g, 3.76 mmol) in toluene (5 mL) was added and the mixture was heated at 110° C. for 4 h. The reaction mixture was allowed to cool to room temperature, partitioned between aqueous hydrochloric acid (1 N) and diethyl ether (about 20 mL) and the organic phase was separated. The aqueous phase was extracted with diethyl ether and the combined organic layers were dried over magnesium sulfate, filtered and concentrated under reduced pressure. The resulting material was purified by silica gel column chromatography (10 to 20% gradient of ethyl acetate in hexanes) to provide the title compound as a solid (0.4 g).

$^1$H NMR (CDCl$_3$): δ 7.61-7.41 (m, 1H), 7.08 (m, 2H), 6.80 (s, 1H), 3.85 (s, 3H).

Step C: Preparation of 4-(2-chloro-4-fluorobenzoyl)-5-(2,6-difluorophenyl)-1-methyl-1H-pyrazole-3-carbonitrile To a mixture of aluminum chloride (0.18 g, 1.36 mmol) in 1,2-dichloroethane (2 mL) was added a mixture of 2-chloro-4-fluorobenzoyl chloride (0.26 g, 1.36 mmol) and 5-(2,6-difluorophenyl)-1-methyl-1H-pyrazole-3-carbonitrile (i.e. the product of Step B) (0.15 g, 0.68 mmol) in dichloroethane (1 mL). The reaction mixture was heated at 180° C. in a Biotage Initiator™ microwave apparatus for 30 minutes. The resulting mixture was poured directly onto a Varian Bond Elute SIC) column and eluted with methylene chloride followed by 30% ethyl acetate in hexanes to provide the title compound, a compound of the present invention, as a solid (0.07 g).

$^1$H NMR (CDCl$_3$): δ 8.12-8.03 (m, 1H), 7.41-7.57 (m, 1H), 7.40-7.33 (m, 1H), 7.12-7.04 (m, 1H), 6.91-7.03 (m, 2H), 3.85 (s, 3H).

Example 11

Preparation of 4-[(2-chloro-4-fluorophenyl)hydroxymethyl]-5-(2,6-difluorophenyl)-1-methyl-1H-pyrazole-3-carbonitrile (Compound 53)

To a mixture of 4-(2-chloro-4-fluorobenzoyl)-5-(2,6-difluorophenyl)-1-methyl-1H-pyrazole-3-carbonitrile (i.e. the product of Example 10) (0.05 g, 0.13 mmol) in ethanol (2 mL) was added sodium borohydride (0.005 g, 0.13 mmol). The reaction was stirred for 30 minutes, and then hydrochloric acid (1 N) (0.5 mL) was added and the mixture was concentrated under reduced pressure. The resulting material was diluted with methylene chloride (5 mL) and filter through a Celite® (diatomaceous earth) extraction tube rinsing with methylene chloride (15 mL). The filtrate was concentrated under reduced pressure and the resulting material purified by flash chromatography on a silica gel, Varian Bond Elute SI® column (10 to 50% gradient of ethyl acetate in hexanes as eluant) to provide the title compound, a compound of the present invention, as a solid (0.03 g).

$^1$H NMR (CDCl$_3$): δ 7.63-7.54 (m, 1H), 7.53-7.40 (m, 1H), 7.06-6.91 (m, 3H), 6.90-6.81 (m, 1H), 6.01 (d, 1H), 3.73 (s, 3H), 2.51 (d, 1H).

Example 12

Preparation of 5-(2,6-difluorophenyl)-α-(4-fluoro-2-methylphenyl)-3-methoxy-1-methyl-1H-pyrazole-4-methanol (Compound 157)

Step A: Preparation of methyl 3-(2,6-difluorophenyl)-2-propynoate

To a mixture of (diazomethyl)trimethylsilane (2.0 M in hexanes, 25 mL, 50 mmol) in tetrahydrofuran (100 mL) at −78° C. was added n-butyllithium (2.5 M in hexanes, 20 mL, 50 mmol) over 5 minutes. After the addition was complete, the reaction mixture temperature was maintained at about −78° C. for 30 minutes and then 2,6-difluorobenzaldehyde (7.1 g, 50 mmol) was added portionwise. The reaction mixture was maintained at −78° C. for an additional 30 minutes and then allowed to warm to room temperature, during which time gas evolution occurred. The reaction mixture was again cooled to −78° C. and n-butyllithium (2.5 M in hexanes, 28 mL, 70 mmol) was added over 5 minutes. After 15 minutes at −78° C., methyl chloroformate (7.8 mL, 100 mmol) was added to the reaction mixture. After 30 minutes, the reaction mixture was allowed to warm to 0° C., and then partitioned between diethyl ether and saturated ammonium chloride solution. The organic phase was separated, dried over magnesium sulfate, filtered and concentrated under reduced pressure. The resulting material was purified by silica gel chromatography (0 to 100% gradient of ethyl acetate in hexanes as eluant) to provide the title compound (8.0 g).

¹H NMR (CDCl₃): δ 7.48-7.33 (m, 1H), 7.06-6.81 (m, 2H), 3.87 (s, 3H).

Step B: Preparation of 5-(2,6-difluorophenyl)-1,2-dihydro-1-methyl-3H-prazol-3-one A mixture of methyl 3-(2,6-difluorophenyl)-2-propynoate (5.0 g, 25.5 mmol) (i.e. the product of Step A) and methylhydrazine (1.6 mL, 30.6 mmol) in a solution of ethanol/water (25 mL, 1:1 mixture) was heated at 70° C. overnight. The reaction mixture was concentrated under reduced pressure and the resulting material purified by silica gel chromatography (90% hexanes in ethyl acetate as eluant) to provide the title compound (2.5 g).
¹H NMR (CDCl₃): δ 11.85 (br s, 1H), 7.51-7.32 (m, 1H), 7.08-6.95 (m, 2H), 5.79 (s, 1H), 3.61 (s, 3H).

Step C: Preparation of 5-(2,6-difluorophenyl)-3-methoxy-1-methyl-1H-pyrazole

A mixture of 5-(2,6-difluorophenyl)-1,2-dihydro-1-methyl-3H-prazol-3-one (2.0 g, 9.6 mmol) (i.e. the product of Step B), potassium carbonate (1.9 g, 14 mmol) and iodomethane (0.75 mL, 12 mmol) in acetonitrile (20 mL) was heated at 70° C. for 4 h and then allowed to cool to room temperature. After about 48 h, the reaction was diluted with dichloromethane and the resulting mixture was filtered through a pad of Celite® (diatomaceous earth) on a sintered glass frit funnel. The filtrate was concentrated under reduced pressure and the resulting material was purified by silica gel chromatography (0 to 100% gradient of ethyl acetate in hexanes as eluant) to provide the title compound (1.3 g).
¹H NMR (CDCl₃): δ 7.48-7.34 (m, 1H), 7.09-6.93 (m, 2H), 5.79 (s, 1H), 3.92 (s, 3H), 3.62 (s, 3H).

Step D: Preparation of 5-(2,6-difluorophenyl)-3-methoxy-1-methyl-1H-pyrazole-4-carboxaldehyde To a mixture of 5-(2,6-difluorophenyl)-3-methoxy-1-methyl-1H-pyrazole (0.5 g, 2.2 mmol) (i.e. the product of Step C) in dimethylformamide (5 mL) at 80° C. was added phosphorus oxychloride (0.31 ml, 3.3 mmol). After 2 h the reaction mixture was allowed to cool to room temperature. The reaction mixture was diluted with sodium hydroxide (1 N, about 5 mL) and water. The resulting mixture was extracted with diethyl ether (2×) and the combined organic layers were washed with water, dried over magnesium sulfate, filtered and concentrated under reduced pressure. The resulting material was purified by silica gel chromatography (0 to 100% gradient of ethyl acetate in dichloromethane as eluant) to provide the title compound (0.5 g).
¹H NMR (CDCl₃): δ 9.65 (s, 1H), 7.59-7.44 (m, 1H), 7.12-7.02 (m, 2H), 4.05 (s, 3H), 3.63 (s, 3H).

Step E: Preparation of 5-(2,6-difluorophenyl)-α-(4-fluoro-2-methylphenyl)-3-methoxy-1-methyl-1H-pyrazole-4-methanol To a mixture of 5-(2,6-difluorophenyl)-3-methoxy-1-methyl-1H-pyrazole-4-carboxaldehyde (0.25 g, 0.99 mmol) (i.e. the product of Step D) in tetrahydrofuran (5 mL) at −30° C. was added 4-fluoro-2-methylphenylmagnesium bromide (0.5 M in hexanes, 2.0 mL, 1.0 mmol). The reaction mixture was allowed to warm to 0° C., quenched with saturated ammonium chloride solution and concentrated under reduced pressure. The resulting material was diluted with dichloromethane and water, poured onto a solid phase extraction tube (Varian Chem Elute®, prepacked with diatomaceous earth) and eluted with dichloromethane. The dichloromethane eluant was concentrated under reduced pressure and the resulting material purified by silica gel chromatography (0 to 100% gradient of ethyl acetate in dichloromethane as eluant) to provide the title compound (0.3 g).
¹H NMR (CDCl₃): δ 7.40-7.20 (m, 2H), 6.93-6.80 (m, 1H), 6.80-6.68 (m, 1H), 6.67-6.58 (m, 1H), 6.58-6.48 (m, 1H), 5.87-5.75 (m, 1H), 4.01 (s, 3H), 3.47 (s, 3H), 2.50-2.37 (m, 1H), 2.05 (s, 3H).

By the procedures described herein together with methods known in the art, the compounds disclosed in the Tables that follow can be prepared. The following abbreviations are used in the Table which follows: Me means methyl, Et means ethyl, n-Pr means n-propyl, c-Pr means cyclopropyl, Ph means phenyl, MeO means methoxy, EtO means ethoxy, —CN means cyano and —NO₂ means nitro.

TABLE 1

| $(R^{3a})_p$ | $(R^{3a})_p$ | $(R^{3a})_p$ | $(R^{3a})_p$ | $(R^{3a})_p$ |
|---|---|---|---|---|
| 2-F | 2-F, 4-Cl | 2-Cl, 4-MeO | 2,4-di-Br, 6-F | 2-F, 4-MeNH(CH₂)₃O |
| 3-F | 2-Cl, 4-F | 2-F, 4-MeO | 2-Br, 4-Cl, 6-F | 2-F, 4-Me₂N(CH₂)₃O |
| 4-F | 2-F, 4-Br | 2-Cl, 4-EtO | 2-I, 4,6-di-F | 2-Cl, 4-MeO(CH₂)₃O |
| 2-Cl | 2-Cl, 4-Br | 2-F, 4-EtO | 4-I, 2,6-di-F | 2,6-di-F, 4-MeNH(CH₂)₃O |
| 3-Cl | 2-Br, 4-Cl | 2,4,5-tri-F | 2,6-di-Cl, 4-CN | 2,6-di-F, 4-MeNH(CH₂)₃ |
| 4-Cl | 2-Br, 4-F | 2,3,5-tri-F | 2,6-di-F, 4-CN | 2,6-di-F, 4-Me₂N(CH₂)₃O |
| 2-Br | 2-I, 4-F | 2,3,6-tri-F | 2,6-di-Cl, 4-MeO | 2,6-di-F, 4-MeO(CH₂)₃O |
| 3-Br | 2-Me, 4-F | 2,4,6-tri-F | 2,6-di-F, 4-MeO | 2,6-di-F, 3-MeNH(CH₂)₃O |
| 4-Br | 2-Cl, 4-CN | 2,4,6-tri-Cl | 2,6-di-Cl, 4-EtO | 2,6-di-F, 3-MeNH(CH₂)₃ |
| 4-Me | 2-F, 4-CN | 2-Cl, 4,6-di-F | 2,6-di-F, 4-EtO | 2,6-di-F, 3-Me₂N(CH₂)₃O |
| 2,6-di-F | 2-Br, 4-CN | 2,6-di-Cl, 4-F | 2-Br, 4-F, 6-Cl | 2,6-di-F, 3-MeO(CH₂)₃O |
| 2,4-di-F | 2-CF₃, 4-F | 2,4-di-Cl, 6-F | 2-Cl, 4-Br, 6-F | 2-Cl-6-F, 4-MeNH(CH₂)₃O |
| 2,4-di-Cl | 2-Me, 4-MeO | 4-Cl, 2,6-di-F | 4-MeNH(CH₂)₃O | 2-Cl-6-F, 4-MeNH(CH₂)₃ |

TABLE 1-continued

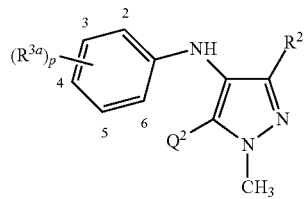

| $(R^{3a})_p$ | $(R^{3a})_p$ | $(R^{3a})_p$ | $(R^{3a})_p$ | $(R^{3a})_p$ |
|---|---|---|---|---|
| 2,6-di-Cl | 2-Me, 4-EtO | 2-Br, 4,6-di-F | 4-Me$_2$N(CH$_2$)$_3$O | 2-Cl-6-F, 4-Me$_2$N(CH$_2$)$_3$O |
| 2,4-di-Me | 2-Br, 4-MeO | 4-Br, 2,6-di-F | 4-MeO(CH$_2$)$_3$O | 2-Cl-6-F, 4-MeO(CH$_2$)$_3$O |

$Q^2$ is 2,6-di-F—Ph and $R^2$ is Me.

The present disclosure also includes Tables 1A through 164A, each of which is constructed the same as Table 1 above, except that the row heading in Table 1 (i.e. "$Q^2$ is 2,6-di-F-Ph and $R^2$ is Me.") is replaced with the respective row heading shown below. For Example, in Table 1A the row heading is "$Q^2$ is 2,6-di-F-Ph and $R^2$ is Cl", and $(R^3)_p$ is as defined in Table 1 above. Thus, the first entry in Table 1A specifically discloses 3-chloro-5-(2,6-difluorophenyl)-N-(2-fluorophenyl)-1-methyl-1H-pyrazole-4-amine. Tables 2A through 164A are constructed similarly.

| Table | Row Heading |
|---|---|
| 1A | $Q^2$ is 2,6-di-F-Ph and $R^2$ is Cl. |
| 2A | $Q^2$ is 2,6-di-F-Ph and $R^2$ is Br. |
| 3A | $Q^2$ is 2,6-di-F-Ph and $R^2$ is Et. |
| 4A | $Q^2$ is 2,6-di-F-Ph and $R^2$ is CN. |
| 5A | $Q^2$ is 2,4-di-F-Ph and $R^2$ is Me. |
| 6A | $Q^2$ is 2,4-di-F-Ph and $R^2$ is Cl. |
| 7A | $Q^2$ is 2,4-di-F-Ph and $R^2$ is Br. |
| 8A | $Q^2$ is 2,4-di-F-Ph and $R^2$ is Et. |
| 9A | $Q^2$ is 2,4-di-F-Ph and $R^2$ is CN. |
| 10A | $Q^2$ is 2,4,6-tri-F-Ph and $R^2$ is Me. |
| 11A | $Q^2$ is 2,4,6-tri-F-Ph and $R^2$ is Cl. |
| 12A | $Q^2$ is 2,4,6-tri-F-Ph and $R^2$ is Br. |
| 13A | $Q^2$ is 2,4,6-tri-F-Ph and $R^2$ is Et. |
| 14A | $Q^2$ is 2,4,6-tri-F-Ph and $R^2$ is CN. |
| 15A | $Q^2$ is 2,6-di-F-4-MeO-Ph and $R^2$ is Me. |
| 16A | $Q^2$ is 2,6-di-F-4-MeO-Ph and $R^2$ is Cl. |
| 17A | $Q^2$ is 2,6-di-F-4-MeO-Ph and $R^2$ is Br. |
| 18A | $Q^2$ is 2,6-di-F-4-MeO-Ph and $R^2$ is Et. |
| 19A | $Q^2$ is 2,6-di-F-4-Me-Ph and $R^2$ is CN. |
| 20A | $Q^2$ is 2,6-di-F-4-EtO-Ph and $R^2$ is Me. |
| 21A | $Q^2$ is 2,6-di-F-4-EtO-Ph and $R^2$ is Cl. |
| 22A | $Q^2$ is 2,6-di-F-4-EtO-Ph and $R^2$ is Br. |
| 23A | $Q^2$ is 2,6-di-F-4-EtO-Ph and $R^2$ is Et. |
| 24A | $Q^2$ is 2,6-di-F-4-EtO-Ph and $R^2$ is CN. |
| 25A | $Q^2$ is 2,6-di-F-4-CN-Ph and $R^2$ is Me. |
| 26A | $Q^2$ is 2,6-di-F-4-CN-Ph and $R^2$ is Cl. |
| 27A | $Q^2$ is 2,6-di-F-4-CN-Ph and $R^2$ is Br. |
| 28A | $Q^2$ is 2,6-di-F-4-CN-Ph and $R^2$ is Et. |
| 29A | $Q^2$ is 2,6-di-F-4-CN-Ph and $R^2$ is CN. |
| 30A | $Q^2$ is 2-Cl-4-F-Ph and $R^2$ is Me. |
| 31A | $Q^2$ is 2-Cl-4-F-Ph and $R^2$ is Cl. |
| 32A | $Q^2$ is 2-Cl-4-F-Ph and $R^2$ is Br. |
| 33A | $Q^2$ is 2-Cl-4-F-Ph and $R^2$ is Et. |
| 34A | $Q^2$ is 2-Cl-4-F-Ph and $R^2$ is CN. |
| 35A | $Q^2$ is 2-Cl-6-F-Ph and $R^2$ is Me. |
| 36A | $Q^2$ is 2-Cl-6-F-Ph and $R^2$ is Cl. |
| 37A | $Q^2$ is 2-Cl-6-F-Ph and $R^2$ is Br. |
| 38A | $Q^2$ is 2-Cl-6-F-Ph and $R^2$ is Et. |
| 39A | $Q^2$ is 2-Cl-6-F-Ph and $R^2$ is CN. |
| 40A | $Q^2$ is 2-Cl-4,6-di-F-Ph and $R^2$ is Me. |
| 41A | $Q^2$ is 2-Cl-4,6-di-F-Ph and $R^2$ is Cl. |
| 42A | $Q^2$ is 2-Cl-4,6-di-F-Ph and $R^2$ is Br. |
| 43A | $Q^2$ is 2-Cl-4,6-di-F-Ph and $R^2$ is Et. |
| 44A | $Q^2$ is 2-Cl-4,6-di-F-Ph and $R^2$ is CN. |
| 45A | $Q^2$ is 4-Cl-2,6-di-F-Ph and $R^2$ is Me. |
| 46A | $Q^2$ is 4-Cl-2,6-di-F-Ph and $R^2$ is Cl. |
| 47A | $Q^2$ is 4-Cl-2,6-di-F-Ph and $R^2$ is Br. |
| 48A | $Q^2$ is 4-Cl-2,6-di-F-Ph and $R^2$ is Et. |
| 49A | $Q^2$ is 4-Cl-2,6-di-F-Ph and $R^2$ is CN. |
| 50A | $Q^2$ is 2-Br-4-F-Ph and $R^2$ is Me. |
| 51A | $Q^2$ is 2-Br-4-F-Ph and $R^2$ is Cl. |
| 52A | $Q^2$ is 2-Br-4-F-Ph and $R^2$ is Br. |
| 53A | $Q^2$ is 2-Br-4-F-Ph and $R^2$ is Et. |
| 54A | $Q^2$ is 2-Br-4-F-Ph and $R^2$ is CN. |
| 55A | $Q^2$ is 2-Br-6-F-Ph and $R^2$ is Me. |
| 56A | $Q^2$ is 2-Br-6-F-Ph and $R^2$ is Cl. |
| 57A | $Q^2$ is 2-Br-6-F-Ph and $R^2$ is Br. |
| 58A | $Q^2$ is 2-Br-6-F-Ph and $R^2$ is Et. |
| 59A | $Q^2$ is 2-Br-6-F-Ph and $R^2$ is CN. |
| 60A | $Q^2$ is 2-Me-4-F-Ph and $R^2$ is Me. |
| 61A | $Q^2$ is 2-Me-4-F-Ph and $R^2$ is Cl. |
| 62A | $Q^2$ is 2-Me-4-F-Ph and $R^2$ is Br. |
| 63A | $Q^2$ is 2-Me-4-F-Ph and $R^2$ is Et. |
| 64A | $Q^2$ is 2-Me-4-F-Ph and $R^2$ is CN. |
| 65A | $Q^2$ is 2-I-4-F-Ph and $R^2$ is Me. |
| 66A | $Q^2$ is 2-I-4-F-Ph and $R^2$ is Cl. |
| 67A | $Q^2$ is 2-I-4-F-Ph and $R^2$ is Br. |
| 68A | $Q^2$ is 2-I-4-F-Ph and $R^2$ is Et. |
| 69A | $Q^2$ is 2-I-4-F-Ph and $R^2$ is CN. |
| 70A | $Q^2$ is 2-F-Ph and $R^2$ is Me. |
| 71A | $Q^2$ is 2-F-Ph and $R^2$ is Cl. |
| 72A | $Q^2$ is 2-F-Ph and $R^2$ is Br. |
| 73A | $Q^2$ is 2-F-Ph and $R^2$ is Et. |
| 74A | $Q^2$ is 2-F-Ph and $R^2$ is CN. |
| 75A | $Q^2$ is 2-Cl-Ph and $R^2$ is Me. |
| 76A | $Q^2$ is 2-Cl-Ph and $R^2$ is Cl. |
| 77A | $Q^2$ is 2-Cl-Ph and $R^2$ is Br. |
| 78A | $Q^2$ is 2-Cl-Ph and $R^2$ is Et. |
| 79A | $Q^2$ is 2-Cl-Ph an $R^2$ is CN. |
| 80A | $Q^2$ is 2-Br-Ph and $R^2$ is Me. |
| 81A | $Q^2$ is 2-Br-Ph and $R^2$ is Cl. |
| 82A | $Q^2$ is 2-Br-Ph and $R^2$ is Br. |
| 83A | $Q^2$ is 2-Br-Ph and $R^2$ is Et. |
| 84A | $Q^2$ is 2-Br-Ph and $R^2$ is CN. |
| 85A | $Q^2$ is 2-F-4-Cl-Ph and $R^2$ is Me. |
| 86A | $Q^2$ is 2-F-4-Cl-Ph and $R^2$ is Cl. |
| 87A | $Q^2$ is 2-F-4-Cl-Ph and $R^2$ is Br. |
| 88A | $Q^2$ is 2-F-4-Cl-Ph and $R^2$ is Et. |
| 89A | $Q^2$ is 2-F-4-Cl-Ph and $R^2$ is CN. |
| 90A | $Q^2$ is 2,4-di-Cl-Ph and $R^2$ is Me. |
| 91A | $Q^2$ is 2,4-di-Cl-Ph and $R^2$ is Cl. |
| 92A | $Q^2$ is 2,4-di-Cl-Ph and $R^2$ is Br. |
| 93A | $Q^2$ is 2,4-di-Cl-Ph and $R^2$ is Et. |
| 94A | $Q^2$ is 2,4-di-Cl-Ph and $R^2$ is CN. |
| 95A | $Q^2$ is 2,6-di-Cl-Ph and $R^2$ is Me. |
| 96A | $Q^2$ is 2,6-di-Cl-Ph and $R^2$ is Cl. |
| 97A | $Q^2$ is 2,6-di-Cl-Ph and $R^2$ is Br. |
| 98A | $Q^2$ is 2,6-di-Cl-Ph and $R^2$ is Et. |

-continued

| Table | Row Heading |
|---|---|
| 99A | $Q^2$ is 2,6-di-Cl-Ph and $R^2$ is CN. |
| 100A | $Q^2$ is 2-F-4-MeO-Ph and $R^2$ is Me. |
| 101A | $Q^2$ is 2-F-4-MeO-Ph and $R^2$ is Cl. |
| 102A | $Q^2$ is 2-F-4-MeO-Ph and $R^2$ is Br. |
| 103A | $Q^2$ is 2-F-4-MeO-Ph and $R^2$ is Et. |
| 104A | $Q^2$ is 2-F-4-MeO-Ph and $R^2$ is CN. |
| 105A | $Q^2$ is 2-F-4-EtO-Ph and $R^2$ is Me. |
| 106A | $Q^2$ is 2-F-4-EtO-Ph and $R^2$ is Cl. |
| 107A | $Q^2$ is 2-F-4-EtO-Ph and $R^2$ is Br. |
| 108A | $Q^2$ is 2-F-4-EtO-Ph and $R^2$ is Et. |
| 109A | $Q^2$ is 2-F-4-EtO-Ph and $R^2$ is CN. |
| 110A | $Q^2$ is 2-Cl-4-MeO-Ph and $R^2$ is Me. |
| 111A | $Q^2$ is 2-Cl-4-MeO-Ph and $R^2$ is Cl. |
| 112A | $Q^2$ is 2-Cl-4-MeO-Ph and $R^2$ is Br. |
| 113A | $Q^2$ is 2-Cl-4-MeO-Ph and $R^2$ is Et. |
| 114A | $Q^2$ is 2-Cl-4-MeO-Ph and $R^2$ is CN. |
| 115A | $Q^2$ is 2-Cl-4-EtO-Ph and $R^2$ is Me. |
| 116A | $Q^2$ is 2-Cl-4-EtO-Ph and $R^2$ is Cl. |
| 117A | $Q^2$ is 2-Cl-4-EtO-Ph and $R^2$ is Br. |
| 118A | $Q^2$ is 2-Cl-4-EtO-Ph and $R^2$ is Et. |
| 119A | $Q^2$ is 2-Cl-4-EtO-Ph and $R^2$ is CN. |
| 120A | $Q^2$ is 2-Br-4-MeO-Ph and $R^2$ is Me. |
| 121A | $Q^2$ is 2-Br-4-MeO-Ph and $R^2$ is Cl. |
| 122A | $Q^2$ is 2-Br-4-MeO-Ph and $R^2$ is Br. |
| 123A | $Q^2$ is 2-Br-4-MeO-Ph and $R^2$ is Et. |
| 124A | $Q^2$ is 2-Br-4-MeO-Ph and $R^2$ is CN. |
| 125A | $Q^2$ is 2-Br-4-EtO-Ph and $R^2$ is Me. |
| 126A | $Q^2$ is 2-Br-4-EtO-Ph and $R^2$ is Cl. |
| 127A | $Q^2$ is 2-Br-4-EtO-Ph and $R^2$ is Br. |
| 128A | $Q^2$ is 2-Br-4-EtO-Ph and $R^2$ is Et. |
| 129A | $Q^2$ is 2-Br-4-EtO-Ph and $R^2$ is CN. |
| 130A | $Q^2$ is 2-F-4-CN-Ph and $R^2$ is Me. |
| 131A | $Q^2$ is 2-F-4-CN-Ph and $R^2$ is Cl. |
| 132A | $Q^2$ is 2-F-4-CN-Ph and $R^2$ is Br. |
| 133A | $Q^2$ is 2-F-4-CN-Ph and $R^2$ is Et. |
| 134A | $Q^2$ is 2-F-4-CN-Ph and $R^2$ is CN. |
| 135A | $Q^2$ is 2-Cl-4-CN-Ph and $R^2$ is Me. |
| 136A | $Q^2$ is 2-Cl-4-CN-Ph and $R^2$ is Cl. |
| 137A | $Q^2$ is 2-Cl-4-CN-Ph and $R^2$ is Br. |
| 138A | $Q^2$ is 2-Cl-4-CN-Ph and $R^2$ is Et. |
| 139A | $Q^2$ is 2-Cl-4-CN-Ph and $R^2$ is CN. |
| 140A | $Q^2$ is 2-Br-4-CN-Ph and $R^2$ is Me. |
| 141A | $Q^2$ is 2-Br-4-CN-Ph and $R^2$ is Cl. |
| 142A | $Q^2$ is 2-Br-4-CN-Ph and $R^2$ is Br. |
| 143A | $Q^2$ is 2-Br-4-CN-Ph and $R^2$ is Et. |
| 144A | $Q^2$ is 2-Br-4-CN-Ph and $R^2$ is CN. |
| 145A | $Q^2$ is 3-Cl-2-pyridinyl and $R^2$ is Me. |
| 146A | $Q^2$ is 3-Cl-2-pyridinyl and $R^2$ is Cl. |
| 147A | $Q^2$ is 3-Cl-2-pyridinyl and $R^2$ is Br. |
| 148A | $Q^2$ is 3-Cl-2-pyridinyl and $R^2$ is Et. |
| 149A | $Q^2$ is 3-Cl-2-pyridinyl and $R^2$ is CN. |
| 150A | $Q^2$ is 3,5-di-Cl-2-pyridinyl and $R^2$ is Me. |
| 151A | $Q^2$ is 3,5-di-Cl-2-pyridinyl and $R^2$ is Cl. |
| 152A | $Q^2$ is 3,5-di-Cl-2-pyridinyl and $R^2$ is Br. |
| 153A | $Q^2$ is 3,5-di-Cl-2-pyridinyl and $R^2$ is Et. |
| 154A | $Q^2$ is 3,5-di-Cl-2-pyridinyl and $R^2$ is CN. |
| 155A | $Q^2$ is 2-Cl-3-thienyl and $R^2$ is Me. |
| 156A | $Q^2$ is 2-Cl-3-thienyl and $R^2$ is Cl. |
| 157A | $Q^2$ is 2-Cl-3-thienyl and $R^2$ is Br. |
| 158A | $Q^2$ is 2-Cl-3-thienyl and $R^2$ is Et. |
| 159A | $Q^2$ is 2-Cl-3-thienyl and $R^2$ is CN. |
| 160A | $Q^2$ is 2,5-di-Cl-3-thienyl and $R^2$ is Me. |
| 161A | $Q^2$ is 2,5-di-Cl-3-thienyl and $R^2$ is Cl. |
| 162A | $Q^2$ is 2,5-di-Cl-3-thienyand $R^2$ is Br. |
| 163A | $Q^2$ is 2,5-di-Cl-3-thienyl and $R^2$ is Et. |
| 164A | $Q^2$ is 2,5-di-Cl-3-thienyl and $R^2$ is CN. |

TABLE 2

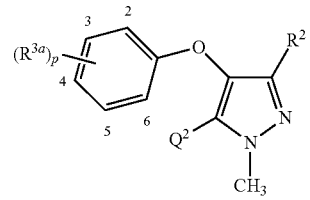

| $(R^{3a})_p$ | $(R^{3a})_p$ | $(R^{3a})_p$ | $(R^{3a})_p$ | $(R^{3a})_p$ |
|---|---|---|---|---|
| 2-F | 2-F, 4-Cl | 2-Cl, 4-MeO | 2,4-di-Br, 6-F | 2-F, 4-MeNH(CH$_2$)$_3$O |
| 3-F | 2-Cl, 4-F | 2-F, 4-MeO | 2-Br, 4-Cl, 6-F | 2-F, 4-Me$_2$N(CH$_2$)$_3$O |
| 4-F | 2-F, 4-Br | 2-Cl, 4-EtO | 2-I, 4,6-di-F | 2-Cl, 4-MeO(CH$_2$)$_3$O |
| 2-Cl | 2-Cl, 4-Br | 2-F, 4-EtO | 4-I, 2,6-di-F | 2,6-di-F, 4-MeNH(CH$_2$)$_3$O |
| 3-Cl | 2-Br, 4-Cl | 2,4,5-tri-F | 2,6-di-Cl, 4-CN | 2,6-di-F, 4-MeNH(CH$_2$)$_3$ |
| 4-Cl | 2-Br, 4-F | 2,3,5-tri-F | 2,6-di-F, 4-CN | 2,6-di-F, 4-Me$_2$N(CH$_2$)$_3$O |
| 2-Br | 2-I, 4-F | 2,3,6-tri-F | 2,6-di-Cl, 4-MeO | 2,6-di-F, 4-MeO(CH$_2$)$_3$O |
| 3-Br | 2-Me, 4-F | 2,4,6-tri-F | 2,6-di-F, 4-MeO | 2,6-di-F, 3-MeNH(CH$_2$)$_3$O |
| 4-Br | 2-Cl, 4-CN | 2,4,6-tri-Cl | 2,6-di-Cl, 4-EtO | 2,6-di-F, 3-MeNH(CH$_2$)$_3$ |
| 4-Me | 2-F, 4-CN | 2-Cl, 4,6-di-F | 2,6-di-F, 4-EtO | 2,6-di-F, 3-Me$_2$N(CH$_2$)$_3$O |
| 2,6-di-F | 2-Br, 4-CN | 2,6-di-Cl, 4-F | 2-Br, 4-F, 6-Cl | 2,6-di-F, 3-MeO(CH$_2$)$_3$O |
| 2,4-di-F | 2-CF$_3$, 4-F | 2,4-di-Cl, 6-F | 2-Cl, 4-Br, 6-F | 2-Cl-6-F, 5-MeNH(CH$_2$)$_3$O |
| 2,4-di-Cl | 2-Me, 4-MeO | 4-Cl, 2,6-di-F | 4-MeNH(CH$_2$)$_3$O | 2-Cl-6-F, 4-MeNH(CH$_2$)$_3$ |
| 2,6-di-Cl | 2-Me, 4-EtO | 2-Br, 4,6-di-F | 4-Me$_2$N(CH$_2$)$_3$O | 2-Cl-6-F, 4-Me$_2$N(CH$_2$)$_3$O |
| 2,4-di-Me | 2-Br, 4-MeO | 4-Br, 2,6-di-F | 4-MeO(CH$_2$)$_3$O | 2-Cl-6-F, 4-MeO(CH$_2$)$_3$O |

$Q^2$ is 2,6-di-F—Ph and $R^2$ is Me.

The present disclosure also includes Tables 1B through 164B, each of which is constructed the same as Table 2 above, except that the row heading in Table 2 (i.e. "$Q^2$ is 2,6-di-F-Ph and $R^2$ is Me") is replaced with the respective row heading shown below. For Example, in Table 1B the row heading is "$Q^2$ is 2,6-di-F-Ph and $R^2$ is Cl", and $(R^3)_p$ is as defined in Table 2 above. Thus, the first entry in Table 1B specifically discloses 3-chloro-5-(2,6-difluorophenyl)-4-(2-fluorophenyl)-1-methyl-1H-pyrazole. Tables 2B through 164B are constructed similarly.

| Table | Row Heading |
| --- | --- |
| 1B | $Q^2$ is 2,6-di-F-Ph and $R^2$ is Cl. |
| 2B | $Q^2$ is 2,6-di-F-Ph and $R^2$ is Br. |
| 3B | $Q^2$ is 2,6-di-F-Ph and $R^2$ is Et. |
| 4B | $Q^2$ is 2,6-di-F-Ph and $R^2$ is CN. |
| 5B | $Q^2$ is 2,4-di-F-Ph and $R^2$ is Me. |
| 6B | $Q^2$ is 2,4-di-F-Ph and $R^2$ is Cl. |
| 7B | $Q^2$ is 2,4-di-F-Ph and $R^2$ is Br. |
| 8B | $Q^2$ is 2,4-di-F-Ph and $R^2$ is Et. |
| 9B | $Q^2$ is 2,4-di-F-Ph and $R^2$ is CN. |
| 10B | $Q^2$ is 2,4,6-tri-F-Ph and $R^2$ is Me. |
| 11B | $Q^2$ is 2,4,6-tri-F-Ph and $R^2$ is Cl. |
| 12B | $Q^2$ is 2,4,6-tri-F-Ph and $R^2$ is Br. |
| 13B | $Q^2$ is 2,4,6-tri-F-Ph and $R^2$ is Et. |
| 14B | $Q^2$ is 2,4,6-tri-F-Ph and $R^2$ is CN. |
| 15B | $Q^2$ is 2,6-di-F-4-OMe-Ph and $R^2$ is Me. |
| 16B | $Q^2$ is 2,6-di-F-4-OMe-Ph and $R^2$ is Cl. |
| 17B | $Q^2$ is 2,6-di-F-4-OMe-Ph and $R^2$ is Br. |
| 18B | $Q^2$ is 2,6-di-F-4-OMe-Ph and $R^2$ is Et. |
| 19B | $Q^2$ is 2,6-di-F-4-OMe-Ph and $R^2$ is CN. |
| 20B | $Q^2$ is 2,6-di-F-4-OEt-Ph and $R^2$ is Me. |
| 21B | $Q^2$ is 2,6-di-F-4-OEt-Ph and $R^2$ is Cl. |
| 22B | $Q^2$ is 2,6-di-F-4-OEt-Ph and $R^2$ is Br. |
| 23B | $Q^2$ is 2,6-di-F-4-OEt-Ph and $R^2$ is Et. |
| 24B | $Q^2$ is 2,6-di-F-4-OEt-Ph and $R^2$ is CN. |
| 25B | $Q^2$ is 2,6-di-F-4-CN-Ph and $R^2$ is Me. |
| 26B | $Q^2$ is 2,6-di-F-4-CN-Ph and $R^2$ is Cl. |
| 27B | $Q^2$ is 2,6-di-F-4-CN-Ph and $R^2$ is Br. |
| 28B | $Q^2$ is 2,6-di-F-4-CN-Ph and $R^2$ is Et. |
| 29B | $Q^2$ is 2,6-di-F-4-CN-Ph and $R^2$ is CN. |
| 30B | $Q^2$ is 2-Cl-4-F-Ph and $R^2$ is Me. |
| 31B | $Q^2$ is 2-Cl-4-F-Ph and $R^2$ is Cl. |
| 32B | $Q^2$ is 2-Cl-4-F-Ph and $R^2$ is Br. |
| 33B | $Q^2$ is 2-Cl-4-F-Ph and $R^2$ is Et. |
| 34B | $Q^2$ is 2-Cl-4-F-Ph and $R^2$ is CN. |
| 35B | $Q^2$ is 2-Cl-6-F-Ph and $R^2$ is Me. |
| 36B | $Q^2$ is 2-Cl-6-F-Ph and $R^2$ is Cl. |
| 37B | $Q^2$ is 2-Cl-6-F-Ph and $R^2$ is Br. |
| 38B | $Q^2$ is 2-Cl-6-F-Ph and $R^2$ is Et. |
| 39B | $Q^2$ is 2-Cl-6-F-Ph and $R^2$ is CN. |
| 40B | $Q^2$ is 2-Cl-4,6-di-F-Ph and $R^2$ is Me. |
| 41B | $Q^2$ is 2-Cl-4,6-di-F-Ph and $R^2$ is Cl. |
| 42B | $Q^2$ is 2-Cl-4,6-di-F-Ph and $R^2$ is Br. |
| 43B | $Q^2$ is 2-Cl-4,6-di-F-Ph and $R^2$ is Et. |
| 44B | $Q^2$ is 2-Cl-4,6-di-F-Ph and $R^2$ is CN. |
| 45B | $Q^2$ is 4-Cl-2,6-di-F-Ph and $R^2$ is Me. |
| 46B | $Q^2$ is 4-Cl-2,6-di-F-Ph and $R^2$ is Cl. |
| 47B | $Q^2$ is 4-Cl-2,6-di-F-Ph and $R^2$ is Br. |
| 48B | $Q^2$ is 4-Cl-2,6-di-F-Ph and $R^2$ is Et. |
| 49B | $Q^2$ is 4-Cl-2,6-di-F-Ph and $R^2$ is CN. |
| 50B | $Q^2$ is 2-Br-4-F-Ph and $R^2$ is Me. |
| 51B | $Q^2$ is 2-Br-4-F-Ph and $R^2$ is Cl. |
| 52B | $Q^2$ is 2-Br-4-F-Ph and $R^2$ is Br. |
| 53B | $Q^2$ is 2-Br-4-F-Ph and $R^2$ is Et. |
| 54B | $Q^2$ is 2-Br-4-F-Ph and $R^2$ is CN. |
| 55B | $Q^2$ is 2-Br-6-F-Ph and $R^2$ is Me. |
| 56B | $Q^2$ is 2-Br-6-F-Ph and $R^2$ is Cl. |
| 57B | $Q^2$ is 2-Br-6-F-Ph and $R^2$ is Br. |
| 58B | $Q^2$ is 2-Br-6-F-Ph and $R^2$ is Et. |
| 59B | $Q^2$ is 2-Br-6-F-Ph and $R^2$ is CN. |
| 60B | $Q^2$ is 2-Me-4-F-Ph and $R^2$ is Me. |
| 61B | $Q^2$ is 2-Me-4-F-Ph and $R^2$ is Cl. |
| 62B | $Q^2$ is 2-Me-4-F-Ph and $R^2$ is Br. |
| 63B | $Q^2$ is 2-Me-4-F-Ph and $R^2$ is Et. |
| 64B | $Q^2$ is 2-Me-4-F-Ph and $R^2$ is CN. |
| 65B | $Q^2$ is 2-I-4-F-Ph and $R^2$ is Me. |
| 66B | $Q^2$ is 2-I-4-F-Ph and $R^2$ is Cl. |
| 67B | $Q^2$ is 2-I-4-F-Ph and $R^2$ is Br. |
| 68B | $Q^2$ is 2-I-4-F-Ph and $R^2$ is Et. |
| 69B | $Q^2$ is 2-I-4-F-Ph and $R^2$ is CN. |
| 70B | $Q^2$ is 2-F-Ph and $R^2$ is Me. |
| 71B | $Q^2$ is 2-F-Ph and $R^2$ is Cl. |
| 72B | $Q^2$ is 2-F-Ph and $R^2$ is Br. |
| 73B | $Q^2$ is 2-F-Ph and $R^2$ is Et. |
| 74B | $Q^2$ is 2-F-Ph and $R^2$ is CN. |
| 75B | $Q^2$ is 2-Cl-Ph and $R^2$ is Me. |
| 76B | $Q^2$ is 2-Cl-Ph and $R^2$ is Cl. |
| 77B | $Q^2$ is 2-Cl-Ph and $R^2$ is Br. |
| 78B | $Q^2$ is 2-Cl-Ph and $R^2$ is Et. |
| 79B | $Q^2$ is 2-Cl-Ph an $R^2$ is CN. |
| 80B | $Q^2$ is 2-Br-Ph and $R^2$ is Me. |
| 81B | $Q^2$ is 2-Br-Ph and $R^2$ is Cl. |
| 82B | $Q^2$ is 2-Br-Ph and $R^2$ is Br. |
| 83B | $Q^2$ is 2-Br-Ph and $R^2$ is Et. |
| 84B | $Q^2$ is 2-Br-Ph and $R^2$ is CN. |
| 85B | $Q^2$ is 2-F-4-Cl-Ph and $R^2$ is Me. |
| 86B | $Q^2$ is 2-F-4-Cl-Ph and $R^2$ is Cl. |
| 87B | $Q^2$ is 2-F-4-Cl-Ph and $R^2$ is Br. |
| 88B | $Q^2$ is 2-F-4-Cl-Ph and $R^2$ is Et. |
| 89B | $Q^2$ is 2-F-4-Cl-Ph and $R^2$ is CN. |
| 90B | $Q^2$ is 2,4-di-Cl-Ph and $R^2$ is Me. |
| 91B | $Q^2$ is 2,4-di-Cl-Ph and $R^2$ is Cl. |
| 92B | $Q^2$ is 2,4-di-Cl-Ph and $R^2$ is Br. |
| 93B | $Q^2$ is 2,4-di-Cl-Ph and $R^2$ is Et. |
| 94B | $Q^2$ is 2,4-di-Cl-Ph and $R^2$ is CN. |
| 95B | $Q^2$ is 2,6-di-Cl-Ph and $R^2$ is Me. |
| 96B | $Q^2$ is 2,6-di-Cl-Ph and $R^2$ is Cl. |
| 97B | $Q^2$ is 2,6-di-Cl-Ph and $R^2$ is Br. |
| 98B | $Q^2$ is 2,6-di-Cl-Ph and $R^2$ is Et. |
| 99B | $Q^2$ is 2,6-di-Cl-Ph and $R^2$ is CN. |
| 100B | $Q^2$ is 2-F-4-MeO-Ph and $R^2$ is Me. |
| 101B | $Q^2$ is 2-F-4-MeO-Ph and $R^2$ is Cl. |
| 102B | $Q^2$ is 2-F-4-MeO-Ph and $R^2$ is Br. |
| 103B | $Q^2$ is 2-F-4-MeO-Ph and $R^2$ is Et. |
| 104B | $Q^2$ is 2-F-4-MeO-Ph and $R^2$ is CN. |
| 105B | $Q^2$ is 2-F-4-EtO-Ph and $R^2$ is Me. |
| 106B | $Q^2$ is 2-F-4-EtO-Ph and $R^2$ is Cl. |
| 107B | $Q^2$ is 2-F-4-EtO-Ph and $R^2$ is Br. |
| 108B | $Q^2$ is 2-F-4-EtO-Ph and $R^2$ is Et. |
| 109B | $Q^2$ is 2-F-4-EtO-Ph and $R^2$ is CN. |
| 110B | $Q^2$ is 2-Cl-4-MeO-Ph and $R^2$ is Me. |
| 111B | $Q^2$ is 2-Cl-4-MeO-Ph and $R^2$ is Cl. |
| 112B | $Q^2$ is 2-Cl-4-MeO-Ph and $R^2$ is Br. |
| 113B | $Q^2$ is 2-Cl-4-MeO-Ph and $R^2$ is Et. |
| 114B | $Q^2$ is 2-Cl-4-MeO-Ph and $R^2$ is CN. |
| 115B | $Q^2$ is 2-Cl-4-EtO-Ph and $R^2$ is Me. |
| 116B | $Q^2$ is 2-Cl-4-EtO-Ph and $R^2$ is Cl. |
| 117B | $Q^2$ is 2-Cl-4-EtO-Ph and $R^2$ is Br. |
| 118B | $Q^2$ is 2-Cl-4-EtO-Ph and $R^2$ is Et. |
| 119B | $Q^2$ is 2-Cl-4-EtO-Ph and $R^2$ is CN. |
| 120B | $Q^2$ is 2-Br-4-MeO-Ph and $R^2$ is Me. |
| 121B | $Q^2$ is 2-Br-4-MeO-Ph and $R^2$ is Cl. |
| 122B | $Q^2$ is 2-Br-4-MeO-Ph and $R^2$ is Br. |
| 123B | $Q^2$ is 2-Br-4-MeO-Ph and $R^2$ is Et. |
| 124B | $Q^2$ is 2-Br-4-MeO-Ph and $R^2$ is CN. |
| 125B | $Q^2$ is 2-Br-4-EtO-Ph and $R^2$ is Me. |
| 126B | $Q^2$ is 2-Br-4-EtO-Ph and $R^2$ is Cl. |
| 127B | $Q^2$ is 2-Br-4-EtO-Ph and $R^2$ is Br. |
| 128B | $Q^2$ is 2-Br-4-EtO-Ph and $R^2$ is Et. |
| 129B | $Q^2$ is 2-Br-4-EtO-Ph and $R^2$ is CN. |
| 130B | $Q^2$ is 2-F-4-CN-Ph and $R^2$ is Me. |
| 131B | $Q^2$ is 2-F-4-CN-Ph and $R^2$ is Cl. |
| 132B | $Q^2$ is 2-F-4-CN-Ph and $R^2$ is Br. |
| 133B | $Q^2$ is 2-F-4-CN-Ph and $R^2$ is Et. |
| 134B | $Q^2$ is 2-F-4-CN-Ph and $R^2$ is CN. |
| 135B | $Q^2$ is 2-Cl-4-CN-Ph and $R^2$ is Me. |
| 136B | $Q^2$ is 2-Cl-4-CN-Ph and $R^2$ is Cl. |
| 137B | $Q^2$ is 2-Cl-4-CN-Ph and $R^2$ is Br. |
| 138B | $Q^2$ is 2-Cl-4-CN-Ph and $R^2$ is Et. |
| 139B | $Q^2$ is 2-Cl-4-CN-Ph and $R^2$ is CN. |
| 140B | $Q^2$ is 2-Br-4-CN-Ph and $R^2$ is Me. |
| 141B | $Q^2$ is 2-Br-4-CN-Ph and $R^2$ is Cl. |
| 142B | $Q^2$ is 2-Br-4-CN-Ph and $R^2$ is Br. |

-continued

| Table | Row Heading |
|---|---|
| 143B | $Q^2$ is 2-Br-4-CN-Ph and $R^2$ is Et. |
| 144B | $Q^2$ is 2-Br-4-CN-Ph and $R^2$ is CN. |
| 145B | $Q^2$ is 3-Cl-2-pyridinyl and $R^2$ is Me. |
| 146B | $Q^2$ is 3-Cl-2-pyridinyl and $R^2$ is Cl. |
| 147B | $Q^2$ is 3-Cl-2-pyridinyl and $R^2$ is Br. |
| 148B | $Q^2$ is 3-Cl-2-pyridinyl and $R^2$ is Et. |
| 149B | $Q^2$ is 3-Cl-2-pyridinyl, and $R^2$ is CN. |
| 150B | $Q^2$ is 3,5-di-Cl-2-pyridinyl and $R^2$ is Me. |
| 151B | $Q^2$ is 3,5-di-Cl-2-pyridinyl and $R^2$ is Cl. |
| 152B | $Q^2$ is 3,5-di-Cl-2-pyridinyl and $R^2$ is Br. |
| 153B | $Q^2$ is 3,5-di-Cl-2-pyridinyl and $R^2$ is Et. |
| 154B | $Q^2$ is 3,5-di-Cl-2-pyridinyl and $R^2$ is CN. |
| 155B | $Q^2$ is 2-Cl-3-thienyl and $R^2$ is Me. |
| 156B | $Q^2$ is 2-Cl-3-thienyl and $R^2$ is Cl. |
| 157B | $Q^2$ is 2-Cl-3-thienyl and $R^2$ is Br. |
| 158B | $Q^2$ is 2-Cl-3-thienyl and $R^2$ is Et. |
| 159B | $Q^2$ is 2-Cl-3-thienyl and $R^2$ is CN. |
| 160B | $Q^2$ is 2,5-di-Cl-3-thienyl and $R^2$ is Me. |
| 161B | $Q^2$ is 2,5-di-Cl-3-thienyl and $R^2$ is Cl. |
| 162B | $Q^2$ is 2,5-di-Cl-3-thienyl, and $R^2$ is Br. |
| 163B | $Q^2$ is 2,5-di-Cl-3-thienyl and $R^2$ is Et. |
| 164B | $Q^2$ is 2,5-di-Cl-3-thienyl and $R^2$ is CN. |

| Table | Row Heading |
|---|---|
| 1C | $Q^2$ is 2,6-di-F-Ph and $R^2$ is Cl. |
| 2C | $Q^2$ is 2,6-di-F-Ph and $R^2$ is Br. |
| 3C | $Q^2$ is 2,6-di-F-Ph and $R^2$ is Et. |
| 4C | $Q^2$ is 2,6-di-F-Ph and $R^2$ is CN. |
| 5C | $Q^2$ is 2,4-di-F-Ph and $R^2$ is Me. |
| 6C | $Q^2$ is 2,4-di-F-Ph and $R^2$ is Cl. |
| 7C | $Q^2$ is 2,4-di-F-Ph and $R^2$ is Br. |
| 8C | $Q^2$ is 2,4-di-F-Ph and $R^2$ is Et. |
| 9C | $Q^2$ is 2,4-di-F-Ph and $R^2$ is CN. |
| 10C | $Q^2$ is 2,4,6-tri-F-Ph and $R^2$ is Me. |
| 11C | $Q^2$ is 2,4,6-tri-F-Ph and $R^2$ is Cl. |
| 12C | $Q^2$ is 2,4,6-tri-F-Ph and $R^2$ is Br. |
| 13C | $Q^2$ is 2,4,6-tri-F-Ph and $R^2$ is Et. |
| 14C | $Q^2$ is 2,4,6-tri-F-Ph and $R^2$ is CN. |
| 15C | $Q^2$ is 2,6-di-F-4-OMe-Ph and $R^2$ is Me. |
| 16C | $Q^2$ is 2,6-di-F-4-OMe-Ph and $R^2$ is Cl. |
| 17C | $Q^2$ is 2,6-di-F-4-OMe-Ph and $R^2$ is Br. |
| 18C | $Q^2$ is 2,6-di-F-4-OMe-Ph and $R^2$ is Et. |
| 19C | $Q^2$ is 2,6-di-F-4-OMe-Ph and $R^2$ is CN. |
| 20C | $Q^2$ is 2,6-di-F-4-OEt-Ph and $R^2$ is Me. |
| 21C | $Q^2$ is 2,6-di-F-4-OEt-Ph and $R^2$ is Cl. |
| 22C | $Q^2$ is 2,6-di-F-4-OEt-Ph and $R^2$ is Br. |
| 23C | $Q^2$ is 2,6-di-F-4-OEt-Ph and $R^2$ is Et. |

TABLE 3

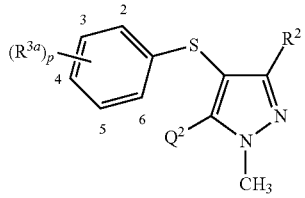

| $(R^{3a})_p$ | $(R^{3a})_p$ | $(R^{3a})_p$ | $(R^{3a})_p$ | $(R^{3a})_p$ |
|---|---|---|---|---|
| 2-F | 2-F, 4-Cl | 2-Cl, 4-MeO | 2,4-di-Br, 6-F | 2-F, 4-MeNH(CH$_2$)$_3$O |
| 3-F | 2-Cl, 4-F | 2-F, 4-MeO | 2-Br, 4-Cl, 6-F | 2-F, 4-Me$_2$N(CH$_2$)$_3$O |
| 4-F | 2-F, 4-Br | 2-Cl, 4-EtO | 2-I, 4,6-di-F | 2-Cl, 4-MeO(CH$_2$)$_3$O |
| 2-Cl | 2-Cl, 4-Br | 2-F, 4-EtO | 4-I, 2,6-di-F | 2,6-di-F, 4-MeNH(CH$_2$)$_3$O |
| 3-Cl | 2-Br, 4-Cl | 2,4,5-tri-F | 2,6-di-Cl, 4-CN | 2,6-di-F, 4-MeNH(CH$_2$)$_3$ |
| 4-Cl | 2-Br, 4-F | 2,3,5-tri-F | 2,6-di-F, 4-CN | 2,6-di-F, 4-Me$_2$N(CH$_2$)$_3$O |
| 2-Br | 2-I, 4-F | 2,3,6-tri-F | 2,6-di-Cl, 4-MeO | 2,6-di-F, 4-MeO(CH$_2$)$_3$O |
| 3-Br | 2-Me, 4-F | 2,4,6-tri-F | 2,6-di-F, 4-MeO | 2,6-di-F, 3-MeNH(CH$_2$)$_3$O |
| 4-Br | 2-Cl, 4-CN | 2,4,6-tri-Cl | 2,6-di-Cl, 4-EtO | 2,6-di-F, 3-MeNH(CH$_2$)$_3$ |
| 4-Me | 2-F, 4-CN | 2-Cl, 4,6-di-F | 2,6-di-F, 4-EtO | 2,6-di-F, 3-Me$_2$N(CH$_2$)$_3$O |
| 2,6-di-F | 2-Br, 4-CN | 2,6-di-Cl, 4-F | 2-Br, 4-F, 6-Cl | 2,6-di-F, 3-MeO(CH$_2$)$_3$O |
| 2,4-di-F | 2-CF$_3$, 4-F | 2,4-di-Cl, 6-F | 2-Cl, 4-Br, 6-F | 2-Cl-6-F, 4-MeNH(CH$_2$)$_3$O |
| 2,4-di-Cl | 2-Me, 4-MeO | 4-Cl, 2,6-di-F | 4-MeNH(CH$_2$)$_3$O | 2-Cl-6-F, 4-MeNH(CH$_2$)$_3$ |
| 2,6-di-Cl | 2-Me, 4-EtO | 2-Br, 4,6-di-F | 4-Me$_2$N(CH$_2$)$_3$O | 2-Cl-6-F, 4-Me$_2$N(CH$_2$)$_3$O |
| 2,4-di-Me | 2-Br, 4-MeO | 4-Br, 2,6-di-F | 4-MeO(CH$_2$)$_3$O | 2-Cl-6-F, 4-MeO(CH$_2$)$_3$O |

$Q^2$ is 2,6-di-F—Ph and $R^2$ is Me.

The present disclosure also includes Tables 1C through 164C, each of which is constructed the same as Table 3 above, except that the row heading in Table 3 (i.e. "$Q^2$ is 2,6-di-F-Ph and $R^2$ is Me") is replaced with the respective row heading shown below. For Example, in Table 1C the row heading is "$Q^2$ is 2,6-di-F-Ph and $R^2$ is Cl", and $(R^3)_p$ is as defined in Table 3 above. Thus, the first entry in Table 1C specifically discloses 3-chloro-5-(2,6-difluorophenyl)-4-[(2-fluorophenyl)thio]-1-methyl-1H-pyrazole. Tables 2C through 164C are constructed similarly.

-continued

| Table | Row Heading |
|---|---|
| 24C | $Q^2$ is 2,6-di-F-4-OEt-Ph and $R^2$ is CN. |
| 25C | $Q^2$ is 2,6-di-F-4-CN-Ph and $R^2$ is Me. |
| 26C | $Q^2$ is 2,6-di-F-4-CN-Ph and $R^2$ is Cl. |
| 27C | $Q^2$ is 2,6-di-F-4-CN-Ph and $R^2$ is Br. |
| 28C | $Q^2$ is 2,6-di-F-4-CN-Ph and $R^2$ is Et. |
| 29C | $Q^2$ is 2,6-di-F-4-CN-Ph and $R^2$ is CN. |
| 30C | $Q^2$ is 2-Cl-4-F-Ph and $R^2$ is Me. |
| 31C | $Q^2$ is 2-Cl-4-F-Ph and $R^2$ is Cl. |
| 32C | $Q^2$ is 2-Cl-4-F-Ph and $R^2$ is Br. |
| 33C | $Q^2$ is 2-Cl-4-F-Ph and $R^2$ is Et. |

-continued

| Table | Row Heading |
|---|---|
| 34C | Q² is 2-Cl-4-F-Ph and R² is CN. |
| 35C | Q² is 2-Cl-6-F-Ph and R² is Me. |
| 36C | Q² is 2-Cl-6-F-Ph and R² is Cl. |
| 37C | Q² is 2-Cl-6-F-Ph and R² is Br. |
| 38C | Q² is 2-Cl-6-F-Ph and R² is Et. |
| 39C | Q² is 2-Cl-6-F-Ph and R² is CN. |
| 40C | Q² is 2-Cl-4,6-di-F-Ph and R² is Me. |
| 41C | Q² is 2-Cl-4,6-di-F-Ph and R² is Cl. |
| 42C | Q² is 2-Cl-4,6-di-F-Ph and R² is Br. |
| 43C | Q² is 2-Cl-4,6-di-F-Ph and R² is Et. |
| 44C | Q² is 2-Cl-4,6-di-F-Ph and R² is CN. |
| 45C | Q² is 4-Cl-2,6-di-F-Ph and R² is Me. |
| 46C | Q² is 4-Cl-2,6-di-F-Ph and R² is Cl. |
| 47C | Q² is 4-Cl-2,6-di-F-Ph and R² is Br. |
| 48C | Q² is 4-Cl-2,6-di-F-Ph and R² is Et. |
| 49C | Q² is 4-Cl-2,6-di-F-Ph and R² is CN. |
| 50C | Q² is 2-Br-4-F-Ph and R² is Me. |
| 51C | Q² is 2-Br-4-F-Ph and R² is Cl. |
| 52C | Q² is 2-Br-4-F-Ph and R² is Br. |
| 53C | Q² is 2-Br-4-F-Ph and R² is Et. |
| 54C | Q² is 2-Br-4-F-Ph and R² is CN. |
| 55C | Q² is 2-Br-6-F-Ph and R² is Me. |
| 56C | Q² is 2-Br-6-F-Ph and R² is Cl. |
| 57C | Q² is 2-Br-6-F-Ph and R² is Br. |
| 58C | Q² is 2-Br-6-F-Ph and R² is Et. |
| 59C | Q² is 2-Br-6-F-Ph and R² is CN. |
| 60C | Q² is 2-Me-4-F-Ph and R² is Me. |
| 61C | Q² is 2-Me-4-F-Ph and R² is Cl. |
| 62C | Q² is 2-Me-4-F-Ph and R² is Br. |
| 63C | Q² is 2-Me-4-F-Ph and R² is Et. |
| 64C | Q² is 2-Me-4-F-Ph and R² is CN. |
| 65C | Q² is 2-I-4-F-Ph and R² is Me. |
| 66C | Q² is 2-I-4-F-Ph and R² is Cl. |
| 67C | Q² is 2-I-4-F-Ph and R² is Br. |
| 68C | Q² is 2-I-4-F-Ph and R² is Et. |
| 69C | Q² is 2-I-4-F-Ph and R² is CN. |
| 70C | Q² is 2-F-Ph and R² is Me. |
| 71C | Q² is 2-F-Ph and R² is Cl. |
| 72C | Q² is 2-F-Ph and R² is Br. |
| 73C | Q² is 2-F-Ph and R² is Et. |
| 74C | Q² is 2-F-Ph and R² is CN. |
| 75C | Q² is 2-Cl-Ph and R² is Me. |
| 76C | Q² is 2-Cl-Ph and R² is Cl. |
| 77C | Q² is 2-Cl-Ph and R² is Br. |
| 78C | Q² is 2-Cl-Ph and R² is Et. |
| 79C | Q² is 2-Cl-Ph an R² is CN. |
| 80C | Q² is 2-Br-Ph and R² is Me. |
| 81C | Q² is 2-Br-Ph and R² is Cl. |
| 82C | Q² is 2-Br-Ph and R² is Br. |
| 83C | Q² is 2-Br-Ph and R² is Et. |
| 84C | Q² is 2-Br-Ph and R² is CN. |
| 85C | Q² is 2-F-4-Cl-Ph and R² is Me. |
| 86C | Q² is 2-F-4-Cl-Ph and R² is Cl. |
| 87C | Q² is 2-F-4-Cl-Ph and R² is Br. |
| 88C | Q² is 2-F-4-Cl-Ph and R² is Et. |
| 89C | Q² is 2-F-4-Cl-Ph and R² is CN. |
| 90C | Q² is 2,4-di-Cl-Ph and R² is Me. |
| 91C | Q² is 2,4-di-Cl-Ph and R² is Cl. |
| 92C | Q² is 2,4-di-Cl-Ph and R² is Br. |
| 93C | Q² is 2,4-di-Cl-Ph and R² is Et. |
| 94C | Q² is 2,4-di-Cl-Ph and R² is CN. |
| 95C | Q² is 2,6-di-Cl-Ph and R² is Me. |
| 96C | Q² is 2,6-di-Cl-Ph and R² is Cl. |
| 97C | Q² is 2,6-di-Cl-Ph and R² is Br. |
| 98C | Q² is 2,6-di-Cl-Ph and R² is Et. |
| 99C | Q² is 2,6-di-Cl-Ph and R² is CN. |
| 100C | Q² is 2-F-4-MeO-Ph and R² is Me. |
| 101C | Q² is 2-F-4-MeO-Ph and R² is Cl. |
| 102C | Q² is 2-F-4-MeO-Ph and R² is Br. |
| 103C | Q² is 2-F-4-MeO-Ph and R² is Et. |
| 104C | Q² is 2-F-4-MeO-Ph and R² is CN. |
| 105C | Q² is 2-F-4-EtO-Ph and R² is Me. |
| 106C | Q² is 2-F-4-EtO-Ph and R² is Cl. |
| 107C | Q² is 2-F-4-EtO-Ph and R² is Br. |
| 108C | Q² is 2-F-4-EtO-Ph and R² is Et. |

-continued

| Table | Row Heading |
|---|---|
| 109C | Q² is 2-F-4-EtO-Ph and R² is CN. |
| 110C | Q² is 2-Cl-4-MeO-Ph and R² is Me. |
| 111C | Q² is 2-Cl-4-MeO-Ph and R² is Cl. |
| 112C | Q² is 2-Cl-4-MeO-Ph and R² is Br. |
| 113C | Q² is 2-Cl-4-MeO-Ph and R² is Et. |
| 114C | Q² is 2-Cl-4-MeO-Ph and R² is CN. |
| 115C | Q² is 2-Cl-4-EtO-Ph and R² is Me. |
| 116C | Q² is 2-Cl-4-EtO-Ph and R² is Cl. |
| 117C | Q² is 2-Cl-4-EtO-Ph and R² is Br. |
| 118C | Q² is 2-Cl-4-EtO-Ph and R² is Et. |
| 119C | Q² is 2-Cl-4-EtO-Ph and R² is CN. |
| 120C | Q² is 2-Br-4-MeO-Ph and R² is Me. |
| 121C | Q² is 2-Br-4-MeO-Ph and R² is Cl. |
| 122C | Q² is 2-Br-4-MeO-Ph and R² is Br. |
| 123C | Q² is 2-Br-4-MeO-Ph and R² is Et. |
| 124C | Q² is 2-Br-4-MeO-Ph and R² is CN. |
| 125C | Q² is 2-Br-4-EtO-Ph and R² is Me. |
| 126C | Q² is 2-Br-4-EtO-Ph and R² is Cl. |
| 127C | Q² is 2-Br-4-EtO-Ph and R² is Br. |
| 128C | Q² is 2-Br-4-EtO-Ph and R² is Et. |
| 129C | Q² is 2-Br-4-EtO-Ph and R² is CN. |
| 130C | Q² is 2-F-4-CN-Ph and R² is Me. |
| 131C | Q² is 2-F-4-CN-Ph and R² is Cl. |
| 132C | Q² is 2-F-4-CN-Ph and R² is Br. |
| 133C | Q² is 2-F-4-CN-Ph and R² is Et. |
| 134C | Q² is 2-F-4-CN-Ph and R² is CN. |
| 135C | Q² is 2-Cl-4-CN-Ph and R² is Me. |
| 136C | Q² is 2-Cl-4-CN-Ph and R² is Cl. |
| 137C | Q² is 2-Cl-4-CN-Ph and R² is Br. |
| 138C | Q² is 2-Cl-4-CN-Ph and R² is Et. |
| 139C | Q² is 2-Cl-4-CN-Ph and R² is CN. |
| 140C | Q² is 2-Br-4-CN-Ph and R² is Me. |
| 141C | Q² is 2-Br-4-CN-Ph and R² is Cl. |
| 142C | Q² is 2-Br-4-CN-Ph and R² is Br. |
| 143C | Q² is 2-Br-4-CN-Ph and R² is Et. |
| 144C | Q² is 2-Br-4-CN-Ph and R² is CN. |
| 145C | Q² is 3-Cl-2-pyridinyl and R² is Me. |
| 146C | Q² is 3-Cl-2-pyridinyl and R² is Cl. |
| 147C | Q² is 3-Cl-2-pyridinyl and R² is Br. |
| 148C | Q² is 3-Cl-2-pyridinyl and R² is Et. |
| 149C | Q² is 3-Cl-2-pyridinyl and R² is CN. |
| 150C | Q² is 3,5-di-Cl-2-pyridinyl and R² is Me. |
| 151C | Q² is 3,5-di-Cl-2-pyridinyl and R² is Cl. |
| 152C | Q² is 3,5-di-Cl-2-pyridinyl and R² is Br. |
| 153C | Q² is 3,5-di-Cl-2-pyridinyl and R² is Et. |
| 154C | Q² is 3,5-di-Cl-2-pyridinyl and R² is CN. |
| 155C | Q² is 2-Cl-3-thienyl and R² is Me. |
| 156C | Q² is 2-Cl-3-thienyl and R² is Cl. |
| 157C | Q² is 2-Cl-3-thienyl and R² is Br. |
| 158C | Q² is 2-Cl-3-thienyl and R² is Et. |
| 159C | Q² is 2-Cl-3-thienyl and R² is CN. |
| 160C | Q² is 2,5-di-Cl-3-thienyl and R² is Me. |
| 161C | Q² is 2,5-di-Cl-3-thienyl and R² is Cl. |
| 162C | Q² is 2,5-di-Cl-3-thienyl and R² is Br. |
| 163C | Q² is 2,5-di-Cl-3-thienyl and R² is Et. |
| 164C | Q² is 2,5-di-Cl-3-thienyl and R² is CN. |

TABLE 4

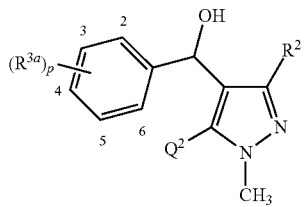

| $(R^{3a})_p$ | $(R^{3a})_p$ | $(R^{3a})_p$ | $(R^{3a})_p$ | $(R^{3a})_p$ |
|---|---|---|---|---|
| 2-F | 2-F, 4-Cl | 2-Cl, 4-MeO | 2,4-di-Br, 6-F | 2-F, 4-MeNH(CH$_2$)$_3$O |
| 3-F | 2-Cl, 4-F | 2-F, 4-MeO | 2-Br, 4-Cl, 6-F | 2-F, 4-Me$_2$N(CH$_2$)$_3$O |
| 4-F | 2-F, 4-Br | 2-Cl, 4-EtO | 2-I, 4,6-di-F | 2-Cl, 4-MeO(CH$_2$)$_3$O |
| 2-Cl | 2-Cl, 4-Br | 2-F, 4-EtO | 4-I, 2,6-di-F | 2,6-di-F, 4-MeNH(CH$_2$)$_3$O |
| 3-Cl | 2-Br, 4-Cl | 2,4,5-tri-F | 2,6-di-Cl, 4-CN | 2,6-di-F, 4-MeNH(CH$_2$)$_3$ |
| 4-Cl | 2-Br, 4-F | 2,3,5-tri-F | 2,6-di-F, 4-CN | 2,6-di-F, 4-Me$_2$N(CH$_2$)$_3$O |
| 2-Br | 2-I, 4-F | 2,3,6-tri-F | 2,6-di-Cl, 4-MeO | 2,6-di-F, 4-MeO(CH$_2$)$_3$O |
| 3-Br | 2-Me, 4-F | 2,4,6-tri-F | 2,6-di-F, 4-MeO | 2,6-di-F, 3-MeNH(CH$_2$)$_3$O |
| 4-Br | 2-Cl, 4-CN | 2,4,6-tri-Cl | 2,6-di-Cl, 4-EtO | 2,6-di-F, 3-MeNH(CH$_2$)$_3$ |
| 4-Me | 2-F, 4-CN | 2-Cl, 4,6-di-F | 2,6-di-F, 4-EtO | 2,6-di-F, 3-Me$_2$N(CH$_2$)$_3$O |
| 2,6-di-F | 2-Br, 4-CN | 2,6-di-Cl, 4-F | 2-Br, 4-F, 6-Cl | 2,6-di-F, 3-MeO(CH$_2$)$_3$O |
| 2,4-di-F | 2-CF$_3$, 4-F | 2,4-di-Cl, 6-F | 2-Cl, 4-Br, 6-F | 2-Cl-6-F, 5-MeNH(CH$_2$)$_3$O |
| 2,4-di-Cl | 2-Me, 4-MeO | 4-Cl, 2,6-di-F | 4-MeNH(CH$_2$)$_3$O | 2-Cl-6-F, 4-MeNH(CH$_2$)$_3$ |
| 2,6-di-Cl | 2-Me, 4-EtO | 2-Br, 4,6-di-F | 4-Me$_2$N(CH$_2$)$_3$O | 2-Cl-6-F, 4-Me$_2$N(CH$_2$)$_3$O |
| 2,4-di-Me | 2-Br, 4-MeO | 4-Br, 2,6-di-F | 4-MeO(CH$_2$)$_3$O | 2-Cl-6-F, 4-MeO(CH$_2$)$_3$O |

$Q^2$ is 2,6-di-F—Ph and $R^2$ is Me.

The present disclosure also includes Tables 1D through 164D, each of which is constructed the same as Table 4 above, except that the row heading in Table 4 (i.e. "$Q^2$ is 2,6-di-F-Ph and $R^2$ is Me") is replaced with the respective row heading shown below. For Example, in Table 1D the row heading is "$Q^2$ is 2,6-di-F-Ph and $R^2$ is Cl", and $(R^3)_p$ is as defined in Table 4 above. Thus, the first entry in Table 1D specifically discloses 3-chloro-5-(2,6-difluorophenyl)-α-(2-fluorophenyl)-1-methyl-1H-pyrazole-4-methanol. Tables 2D through 164D are constructed similarly.

| Table | Row Heading |
|---|---|
| 1D | $Q^2$ is 2,6-di-F-Ph and $R^2$ is Cl. |
| 2D | $Q^2$ is 2,6-di-F-Ph and $R^2$ is Br. |
| 3D | $Q^2$ is 2,6-di-F-Ph and $R^2$ is Et. |
| 4D | $Q^2$ is 2,6-di-F-Ph and $R^2$ is CN. |
| 5D | $Q^2$ is 2,4-di-F-Ph and $R^2$ is Me. |
| 6D | $Q^2$ is 2,4-di-F-Ph and $R^2$ is Cl. |
| 7D | $Q^2$ is 2,4-di-F-Ph and $R^2$ is Br. |
| 8D | $Q^2$ is 2,4-di-F-Ph and $R^2$ is Et. |
| 9D | $Q^2$ is 2,4-di-F-Ph and $R^2$ is CN. |
| 10D | $Q^2$ is 2,4,6-tri-F-Ph and $R^2$ is Me. |
| 11D | $Q^2$ is 2,4,6-tri-F-Ph and $R^2$ is Cl. |
| 12D | $Q^2$ is 2,4,6-tri-F-Ph and $R^2$ is Br. |
| 13D | $Q^2$ is 2,4,6-tri-F-Ph and $R^2$ is Et. |
| 14D | $Q^2$ is 2,4,6-tri-F-Ph and $R^2$ is CN. |
| 15D | $Q^2$ is 2,6-di-F-4-OMe-Ph and $R^2$ is Me. |
| 16D | $Q^2$ is 2,6-di-F-4-OMe-Ph and $R^2$ is Cl. |
| 17D | $Q^2$ is 2,6-di-F-4-OMe-Ph and $R^2$ is Br. |
| 18D | $Q^2$ is 2,6-di-F-4-OMe-Ph and $R^2$ is Et |
| 19D | $Q^2$ is 2,6-di-F-4-OMe-Ph and $R^2$ is CN |
| 20D | $Q^2$ is 2,6-di-F-4-OEt-Ph and $R^2$ is Me. |
| 21D | $Q^2$ is 2,6-di-F-4-OEt-Ph and $R^2$ is Cl. |
| 22D | $Q^2$ is 2,6-di-F-4-OEt-Ph and $R^2$ is Br. |
| 23D | $Q^2$ is 2,6-di-F-4-OEt-Ph and $R^2$ is Et. |
| 24D | $Q^2$ is 2,6-di-F-4-OEt-Ph and $R^2$ is CN. |
| 25D | $Q^2$ is 2,6-di-F-4-CN-Ph and $R^2$ is Me. |
| 26D | $Q^2$ is 2,6-di-F-4-CN-Ph and $R^2$ is Cl. |
| 27D | $Q^2$ is 2,6-di-F-4-CN-Ph and $R^2$ is Br. |
| 28D | $Q^2$ is 2,6-di-F-4-CN-Ph and $R^2$ is Et. |
| 29D | $Q^2$ is 2,6-di-F-4-CN-Ph and $R^2$ is CN. |
| 30D | $Q^2$ is 2-Cl-4-F-Ph and $R^2$ is Me. |
| 31D | $Q^2$ is 2-Cl-4-F-Ph and $R^2$ is Cl. |
| 32D | $Q^2$ is 2-Cl-4-F-Ph and $R^2$ is Br. |
| 33D | $Q^2$ is 2-Cl-4-F-Ph and $R^2$ is Et. |
| 34D | $Q^2$ is 2-Cl-4-F-Ph and $R^2$ is CN. |
| 35D | $Q^2$ is 2-Cl-6-F-Ph and $R^2$ is Me. |
| 36D | $Q^2$ is 2-Cl-6-F-Ph and $R^2$ is Cl. |
| 37D | $Q^2$ is 2-Cl-6-F-Ph and $R^2$ is Br. |
| 38D | $Q^2$ is 2-Cl-6-F-Ph and $R^2$ is Et. |
| 39D | $Q^2$ is 2-Cl-6-F-Ph and $R^2$ is CN. |
| 40D | $Q^2$ is 2-Cl-4,6-di-F-Ph and $R^2$ is Me. |
| 41D | $Q^2$ is 2-Cl-4,6-di-F-Ph and $R^2$ is Cl. |
| 42D | $Q^2$ is 2-Cl-4,6-di-F-Ph and $R^2$ is Br. |
| 43D | $Q^2$ is 2-Cl-4,6-di-F-Ph and $R^2$ is Et. |
| 44D | $Q^2$ is 2-Cl-4,6-di-F-Ph and $R^2$ is CN. |
| 45D | $Q^2$ is 4-Cl-2,6-di-F-Ph and $R^2$ is Me. |
| 46D | $Q^2$ is 4-Cl-2,6-di-F-Ph and $R^2$ is Cl. |
| 47D | $Q^2$ is 4-Cl-2,6-di-F-Ph and $R^2$ is Br. |
| 48D | $Q^2$ is 4-Cl-2,6-di-F-Ph and $R^2$ is Et. |
| 49D | $Q^2$ is 4-Cl-2,6-di-F-Ph and $R^2$ is CN. |
| 50D | $Q^2$ is 2-Br-4-F-Ph and $R^2$ is Me. |
| 51D | $Q^2$ is 2-Br-4-F-Ph and $R^2$ is Cl. |
| 52D | $Q^2$ is 2-Br-4-F-Ph and $R^2$ is Br. |
| 53D | $Q^2$ is 2-Br-4-F-Ph and $R^2$ is Et. |
| 54D | $Q^2$ is 2-Br-4-F-Ph and $R^2$ is CN. |
| 55D | $Q^2$ is 2-Br-6-F-Ph and $R^2$ is Me. |
| 56D | $Q^2$ is 2-Br-6-F-Ph and $R^2$ is Cl. |
| 57D | $Q^2$ is 2-Br-6-F-Ph and $R^2$ is Br. |
| 58D | $Q^2$ is 2-Br-6-F-Ph and $R^2$ is Et. |
| 59D | $Q^2$ is 2-Br-6-F-Ph and $R^2$ is CN. |
| 60D | $Q^2$ is 2-Me-4-F-Ph and $R^2$ is Me. |
| 61D | $Q^2$ is 2-Me-4-F-Ph and $R^2$ is Cl. |
| 62D | $Q^2$ is 2-Me-4-F-Ph and $R^2$ is Br. |
| 63D | $Q^2$ is 2-Me-4-F-Ph and $R^2$ is Et. |
| 64D | $Q^2$ is 2-Me-4-F-Ph and $R^2$ is CN. |
| 65D | $Q^2$ is 2-I-4-F-Ph and $R^2$ is Me. |
| 66D | $Q^2$ is 2-I-4-F-Ph and $R^2$ is Cl. |
| 67D | $Q^2$ is 2-I-4-F-Ph and $R^2$ is Br. |
| 68D | $Q^2$ is 2-I-4-F-Ph and $R^2$ is Et. |
| 69D | $Q^2$ is 2-I-4-F-Ph and $R^2$ is CN. |
| 70D | $Q^2$ is 2-F-Ph and $R^2$ is Me. |
| 71D | $Q^2$ is 2-F-Ph and $R^2$ is Cl. |
| 72D | $Q^2$ is 2-F-Ph and $R^2$ is Br. |
| 73D | $Q^2$ is 2-F-Ph and $R^2$ is Et. |
| 74D | $Q^2$ is 2-F-Ph and $R^2$ is CN. |

-continued

| Table | Row Heading |
|---|---|
| 75D | Q² is 2-Cl-Ph and R² is Me. |
| 76D | Q² is 2-Cl-Ph and R² is Cl. |
| 77D | Q² is 2-Cl-Ph and R² is Br. |
| 78D | Q² is 2-Cl-Ph and R² is Et. |
| 79D | Q² is 2-Cl-Ph an R² is CN |
| 80D | Q² is 2-Br-Ph and R² is Me. |
| 81D | Q² is 2-Br-Ph and R² is Cl. |
| 82D | Q² is 2-Br-Ph and R² is Br. |
| 83D | Q² is 2-Br-Ph and R² is Et. |
| 84D | Q² is 2-Br-Ph and R² is CN. |
| 85D | Q² is 2-F-4-Cl-Ph and R² is Me. |
| 86D | Q² is 2-F-4-Cl-Ph and R² is Cl. |
| 87D | Q² is 2-F-4-Cl-Ph and R² is Br. |
| 88D | Q² is 2-F-4-Cl-Ph and R² is Et. |
| 89D | Q² is 2-F-4-Cl-Ph and R² is CN. |
| 90D | Q² is 2,4-di-Cl-Ph and R² is Me. |
| 91D | Q² is 2,4-di-Cl-Ph and R² is Cl. |
| 92D | Q² is 2,4-di-Cl-Ph and R² is Br. |
| 93D | Q² is 2,4-di-Cl-Ph and R² is Et. |
| 94D | Q² is 2,4-di-Cl-Ph and R² is CN. |
| 95D | Q² is 2,6-di-Cl-Ph and R² is Me. |
| 96D | Q² is 2,6-di-Cl-Ph and R² is Cl. |
| 97D | Q² is 2,6-di-Cl-Ph and R² is Br. |
| 98D | Q² is 2,6-di-Cl-Ph and R² is Et. |
| 99D | Q² is 2,6-di-Cl-Ph and R² is CN. |
| 100D | Q² is 2-F-4-MeO-Ph and R² is Me. |
| 101D | Q² is 2-F-4-MeO-Ph and R² is Cl. |
| 102D | Q² is 2-F-4-MeO-Ph and R² is Br. |
| 103D | Q² is 2-F-4-MeO-Ph and R² is Et. |
| 104D | Q² is 2-F-4-MeO-Ph and R² is CN. |
| 105D | Q² is 2-F-4-EtO-Ph and R² is Me. |
| 106D | Q² is 2-F-4-EtO-Ph and R² is Cl. |
| 107D | Q² is 2-F-4-EtO-Ph and R² is Br. |
| 108D | Q² is 2-F-4-EtO-Ph and R² is Et. |
| 109D | Q² is 2-F-4-EtO-Ph and R² is CN. |
| 110D | Q² is 2-Cl-4-MeO-Ph and R² is Me. |
| 111D | Q² is 2-Cl-4-MeO-Ph and R² is Cl. |
| 112D | Q² is 2-Cl-4-MeO-Ph and R² is Br. |
| 113D | Q² is 2-Cl-4-MeO-Ph and R² is Et. |
| 114D | Q² is 2-Cl-4-MeO-Ph and R² is CN. |
| 115D | Q² is 2-Cl-4-EtO-Ph and R² is Me. |
| 116D | Q² is 2-Cl-4-EtO-Ph and R² is Cl. |
| 117D | Q² is 2-Cl-4-EtO-Ph and R² is Br. |
| 118D | Q² is 2-Cl-4-EtO-Ph and R² is Et. |
| 119D | Q² is 2-Cl-4-EtO-Ph and R² is CN. |
| 120D | Q² is 2-Br-4-MeO-Ph and R² is Me. |

-continued

| Table | Row Heading |
|---|---|
| 121D | Q² is 2-Br-4-MeO-Ph and R² is Cl. |
| 122D | Q² is 2-Br-4-MeO-Ph and R² is Br. |
| 123D | Q² is 2-Br-4-MeO-Ph and R² is Et. |
| 124D | Q² is 2-Br-4-MeO-Ph and R² is CN. |
| 125D | Q² is 2-Br-4-EtO-Ph and R² is Me. |
| 126D | Q² is 2-Br-4-EtO-Ph and R² is Cl. |
| 127D | Q² is 2-Br-4-EtO-Ph and R² is Br. |
| 128D | Q² is 2-Br-4-EtO-Ph and R² is Et. |
| 129D | Q² is 2-Br-4-EtO-Ph and R² is CN. |
| 130D | Q² is 2-F-4-CN-Ph and R² is Me. |
| 131D | Q² is 2-F-4-CN-Ph and R² is Cl. |
| 132D | Q² is 2-F-4-CN-Ph and R² is Br. |
| 133D | Q² is 2-F-4-CN-Ph and R² is Et. |
| 134D | Q² is 2-F-4-CN-Ph and R² is CN. |
| 135D | Q² is 2-Cl-4-CN-Ph and R² is Me. |
| 136D | Q² is 2-Cl-4-CN-Ph and R² is Cl. |
| 137D | Q² is 2-Cl-4-CN-Ph and R² is Br. |
| 138D | Q² is 2-Cl-4-CN-Ph and R² is Et. |
| 139D | Q² is 2-Cl-4-CN-Ph and R² is CN. |
| 140D | Q² is 2-Br-4-CN-Ph and R² is Me. |
| 141D | Q² is 2-Br-4-CN-Ph and R² is Cl. |
| 142D | Q² is 2-Br-4-CN-Ph and R² is Br. |
| 143D | Q² is 2-Br-4-CN-Ph and R² is Et. |
| 144D | Q² is 2-Br-4-CN-Ph and R² is CN. |
| 145D | Q² is 3-Cl-2-pyridinyl and R² is Me. |
| 146D | Q² is 3-Cl-2-pyridinyl and R² is Cl. |
| 147D | Q² is 3-Cl-2-pyridinyl and R² is Br. |
| 148D | Q² is 3-Cl-2-pyridinyl and R² is Et. |
| 149D | Q² is 3-Cl-2-pyridinyl and R² is CN. |
| 150D | Q² is 3,5-di-Cl-2-pyridinyl and R² is Me. |
| 151D | Q² is 3,5-di-Cl-2-pyridinyl and R² is Cl. |
| 152D | Q² is 3,5-di-Cl-2-pyridinyl and R² is Br. |
| 153D | Q² is 3,5-di-Cl-2-pyridinyl and R² is Et. |
| 154D | Q² is 3,5-di-Cl-2-pyridinyl and R² is CN. |
| 155D | Q² is 2-Cl-3-thienyl and R² is Me. |
| 156D | Q² is 2-Cl-3-thienyl and R² is Cl. |
| 157D | Q² is 2-Cl-3-thienyl and R² is Br. |
| 158D | Q² is 2-Cl-3-thienyl and R² is Et. |
| 159D | Q² is 2-Cl-3-thienyl and R² is CN. |
| 160D | Q² is 2,5-di-Cl-3-thienyl and R² is Me. |
| 161D | Q² is 2,5-di-Cl-3-thienyl and R² is Cl. |
| 162D | Q² is 2,5-di-Cl-3-thienyl and R² is Br. |
| 163D | Q² is 2,5-di-Cl-3-thienyl and R² is Et. |
| 164D | Q² is 2,5-di-Cl-3-thienyl and R² is CN. |

TABLE 5

| $(R^{3a})_p$ | $(R^{3a})_p$ | $(R^{3a})_p$ | $(R^{3a})_p$ | $(R^{3a})_p$ |
|---|---|---|---|---|
| 2-F | 2-F, 4-Cl | 2-Cl, 4-MeO | 2,4-di-Br, 6-F | 2-F, 4-MeNH(CH₂)₃O |
| 3-F | 2-Cl, 4-F | 2-F, 4-MeO | 2-Br, 4-Cl, 6-F | 2-F, 4-Me₂N(CH₂)₃O |
| 4-F | 2-F, 4-Br | 2-Cl, 4-EtO | 2-I, 4,6-di-F | 2-Cl, 4-MeO(CH₂)₃O |
| 2-Cl | 2-Cl, 4-Br | 2-F, 4-EtO | 4-I, 2,6-di-F | 2,6-di-F, 4-MeNH(CH₂)₃O |
| 3-Cl | 2-Br, 4-Cl | 2,4,5-tri-F | 2,6-di-Cl, 4-CN | 2,6-di-F, 4-MeNH(CH₂)₃ |
| 4-Cl | 2-Br, 4-F | 2,3,5-tri-F | 2,6-di-F, 4-CN | 2,6-di-F, 4-Me₂N(CH₂)₃ |
| 2-Br | 2-I, 4-F | 2,3,6-tri-F | 2,6-di-Cl, 4-MeO | 2,6-di-F, 4-MeO(CH₂)₃O |
| 3-Br | 2-Me, 4-F | 2,4,6-tri-F | 2,6-di-F, 4-MeO | 2,6-di-F, 3-MeNH(CH₂)₃O |
| 4-Br | 2-Cl, 4-CN | 2,4,6-tri-Cl | 2,6-di-Cl, 4-EtO | 2,6-di-F, 3-MeNH(CH₂)₃ |
| 4-Me | 2-F, 4-CN | 2-Cl, 4,6-di-F | 2,6-di-F, 4-EtO | 2,6-di-F, 3-Me₂N(CH₂)₃O |
| 2,6-di-F | 2-Br, 4-CN | 2,6-di-Cl, 4-F | 2-Br, 4-F, 6-Cl | 2,6-di-F, 3-MeO(CH₂)₃O |
| 2,4-di-F | 2-CF₃, 4-F | 2,4-di-Cl, 6-F | 2-Cl, 4-Br, 6-F | 2-Cl-6-F, 5-MeNH(CH₂)₃O |
| 2,4-di-Cl | 2-Me, 4-MeO | 4-Cl, 2,6-di-F | 4-MeNH(CH₂)₃O | 2-Cl-6-F, 4-MeNH(CH₂)₃ |

TABLE 5-continued

| $(R^{3a})_p$ | $(R^{3a})_p$ | $(R^{3a})_p$ | $(R^{3a})_p$ | $(R^{3a})_p$ |
|---|---|---|---|---|
| 2,6-di-Cl | 2-Me, 4-EtO | 2-Br, 4,6-di-F | 4-Me$_2$N(CH$_2$)$_3$O | 2-Cl-6-F, 4-Me$_2$N(CH$_2$)$_3$O |
| 2,4-di-Me | 2-Br, 4-MeO | 4-Br, 2,6-di-F | 4-MeO(CH$_2$)$_3$O | 2-Cl-6-F, 4-MeO(CH$_2$)$_3$O |

$Q^2$ is 2,6-di-F—Ph and $R^2$ is Me.

The present disclosure also includes Tables 1E through 164E, each of which is constructed the same as Table 5 above, except that the row heading in Table 5 (i.e. "$Q^2$ is 2,6-di-F-Ph and $R^2$ is Me") is replaced with the respective row heading shown below. For Example, in Table 1E the row heading is "$Q^2$ is 2,6-di-F-Ph and $R^2$ is Cl", and $(R^3)_p$ is as defined in Table 5 above. Thus, the first entry in Table 1E specifically discloses (3-chloro-5-(2,6-difluorophenyl)-1-methyl-1H-pyrazol-4-yl](2-fluorophenyl)methanol. Tables 2E through 164E are constructed similarly.

| Table | Row Heading |
|---|---|
| 1E | $Q^2$ is 2,6-di-F-Ph and $R^2$ is Cl. |
| 2E | $Q^2$ is 2,6-di-F-Ph and $R^2$ is Br. |
| 3E | $Q^2$ is 2,6-di-F-Ph and $R^2$ is Et. |
| 4E | $Q^2$ is 2,6-di-F-Ph and $R^2$ is CN. |
| 5E | $Q^2$ is 2,4-di-F-Ph and $R^2$ is Me. |
| 6E | $Q^2$ is 2,4-di-F-Ph and $R^2$ is Cl. |
| 7E | $Q^2$ is 2,4-di-F-Ph and $R^2$ is Br. |
| 8E | $Q^2$ is 2,4-di-F-Ph and $R^2$ is Et. |
| 9E | $Q^2$ is 2,4-di-F-Ph and $R^2$ is CN. |
| 10E | $Q^2$ is 2,4,6-tri-F-Ph and $R^2$ is Me. |
| 11E | $Q^2$ is 2,4,6-tri-F-Ph and $R^2$ is Cl. |
| 12E | $Q^2$ is 2,4,6-tri-F-Ph and $R^2$ is Br. |
| 13E | $Q^2$ is 2,4,6-tri-F-Ph and $R^2$ is Et. |
| 14E | $Q^2$ is 2,4,6-tri-F-Ph and $R^2$ is CN. |
| 15E | $Q^2$ is 2,6-di-F-4-OMe-Ph and $R^2$ is Me. |
| 16E | $Q^2$ is 2,6-di-F-4-OMe-Ph and $R^2$ is Cl. |
| 17E | $Q^2$ is 2,6-di-F-4-OMe-Ph and $R^2$ is Br. |
| 18E | $Q^2$ is 2,6-di-F-4-OMe-Ph and $R^2$ is Et |
| 19E | $Q^2$ is 2,6-di-F-4-OMe-Ph and $R^2$ is CN |
| 20E | $Q^2$ is 2,6-di-F-4-OEt-Ph and $R^2$ is Me. |
| 21E | $Q^2$ is 2,6-di-F-4-OEt-Ph and $R^2$ is Cl. |
| 22E | $Q^2$ is 2,6-di-F-4-OEt-Ph and $R^2$ is Br. |
| 23E | $Q^2$ is 2,6-di-F-4-OEt-Ph and $R^2$ is Et. |
| 24E | $Q^2$ is 2,6-di-F-4-OEt-Ph and $R^2$ is CN. |
| 25E | $Q^2$ is 2,6-di-F-4-CN-Ph and $R^2$ is Me. |
| 26E | $Q^2$ is 2,6-di-F-4-CN-Ph and $R^2$ is Cl. |
| 27E | $Q^2$ is 2,6-di-F-4-CN-Ph and $R^2$ is Br. |
| 28E | $Q^2$ is 2,6-di-F-4-CN-Ph and $R^2$ is Et. |
| 29E | $Q^2$ is 2,6-di-F-4-CN-Ph and $R^2$ is CN. |
| 30E | $Q^2$ is 2-Cl-4-F-Ph and $R^2$ is Me. |
| 31E | $Q^2$ is 2-Cl-4-F-Ph and $R^2$ is Cl. |
| 32E | $Q^2$ is 2-Cl-4-F-Ph and $R^2$ is Br. |
| 33E | $Q^2$ is 2-Cl-4-F-Ph and $R^2$ is Et. |
| 34E | $Q^2$ is 2-Cl-4-F-Ph and $R^2$ is CN. |
| 35E | $Q^2$ is 2-Cl-6-F-Ph and $R^2$ is Me. |
| 36E | $Q^2$ is 2-Cl-6-F-Ph and $R^2$ is Cl. |
| 37E | $Q^2$ is 2-Cl-6-F-Ph and $R^2$ is Br. |
| 38E | $Q^2$ is 2-Cl-6-F-Ph and $R^2$ is Et. |
| 39E | $Q^2$ is 2-Cl-6-F-Ph and $R^2$ is CN. |
| 40E | $Q^2$ is 2-Cl-4,6-di-F-Ph and $R^2$ is Me. |
| 41E | $Q^2$ is 2-Cl-4,6-di-F-Ph and $R^2$ is Cl. |
| 42E | $Q^2$ is 2-Cl-4,6-di-F-Ph and $R^2$ is Br. |
| 43E | $Q^2$ is 2-Cl-4,6-di-F-Ph and $R^2$ is Et. |
| 44E | $Q^2$ is 2-Cl-4,6-di-F-Ph and $R^2$ is CN. |
| 45E | $Q^2$ is 4-Cl-2,6-di-F-Ph and $R^2$ is Me. |
| 46E | $Q^2$ is 4-Cl-2,6-di-F-Ph and $R^2$ is Cl. |
| 47E | $Q^2$ is 4-Cl-2,6-di-F-Ph and $R^2$ is Br. |
| 48E | $Q^2$ is 4-Cl-2,6-di-F-Ph and $R^2$ is Et. |
| 49E | $Q^2$ is 4-Cl-2,6-di-F-Ph and $R^2$ is CN. |
| 50E | $Q^2$ is 2-Br-4-F-Ph and $R^2$ is Me. |
| 51E | $Q^2$ is 2-Br-4-F-Ph and $R^2$ is Cl. |
| 52E | $Q^2$ is 2-Br-4-F-Ph and $R^2$ is Br. |
| 53E | $Q^2$ is 2-Br-4-F-Ph and $R^2$ is Et. |
| 54E | $Q^2$ is 2-Br-4-F-Ph and $R^2$ is CN. |
| 55E | $Q^2$ is 2-Br-6-F-Ph and $R^2$ is Me. |
| 56E | $Q^2$ is 2-Br-6-F-Ph and $R^2$ is Cl. |
| 57E | $Q^2$ is 2-Br-6-F-Ph and $R^2$ is Br. |
| 58E | $Q^2$ is 2-Br-6-F-Ph and $R^2$ is Et. |
| 59E | $Q^2$ is 2-Br-6-F-Ph and $R^2$ is CN. |
| 60E | $Q^2$ is 2-Me-4-F-Ph and $R^2$ is Me. |
| 61E | $Q^2$ is 2-Me-4-F-Ph and $R^2$ is Cl. |
| 62E | $Q^2$ is 2-Me-4-F-Ph and $R^2$ is Br. |
| 63E | $Q^2$ is 2-Me-4-F-Ph and $R^2$ is Et. |
| 64E | $Q^2$ is 2-Me-4-F-Ph and $R^2$ is CN. |
| 65E | $Q^2$ is 2-I-4-F-Ph and $R^2$ is Me. |
| 66E | $Q^2$ is 2-I-4-F-Ph and $R^2$ is Cl. |
| 67E | $Q^2$ is 2-I-4-F-Ph and $R^2$ is Br. |
| 68E | $Q^2$ is 2-I-4-F-Ph and $R^2$ is Et. |
| 69E | $Q^2$ is 2-I-4-F-Ph and $R^2$ is CN. |
| 70E | $Q^2$ is 2-F-Ph and $R^2$ is Me. |
| 71E | $Q^2$ is 2-F-Ph and $R^2$ is Cl. |
| 72E | $Q^2$ is 2-F-Ph and $R^2$ is Br. |
| 73E | $Q^2$ is 2-F-Ph and $R^2$ is Et. |
| 74E | $Q^2$ is 2-F-Ph and $R^2$ is CN. |
| 75E | $Q^2$ is 2-Cl-Ph and $R^2$ is Me. |
| 76E | $Q^2$ is 2-Cl-Ph and $R^2$ is Cl. |
| 77E | $Q^2$ is 2-Cl-Ph and $R^2$ is Br. |
| 78E | $Q^2$ is 2-Cl-Ph and $R^2$ is Et. |
| 79E | $Q^2$ is 2-Cl-Ph an $R^2$ is CN. |
| 80E | $Q^2$ is 2-Br-Ph and $R^2$ is Me. |
| 81E | $Q^2$ is 2-Br-Ph and $R^2$ is Cl. |
| 82E | $Q^2$ is 2-Br-Ph and $R^2$ is Br. |
| 83E | $Q^2$ is 2-Br-Ph and $R^2$ is Et. |
| 84E | $Q^2$ is 2-Br-Ph and $R^2$ is CN. |
| 85E | $Q^2$ is 2-F-4-Cl-Ph and $R^2$ is Me. |
| 86E | $Q^2$ is 2-F-4-Cl-Ph and $R^2$ is Cl. |
| 87E | $Q^2$ is 2-F-4-Cl-Ph and $R^2$ is Br. |
| 88E | $Q^2$ is 2-F-4-Cl-Ph and $R^2$ is Et. |
| 89E | $Q^2$ is 2-F-4-Cl-Ph and $R^2$ is CN. |
| 90E | $Q^2$ is 2,4-di-Cl-Ph and $R^2$ is Me. |
| 91E | $Q^2$ is 2,4-di-Cl-Ph and $R^2$ is Cl. |
| 92E | $Q^2$ is 2,4-di-Cl-Ph and $R^2$ is Br. |
| 93E | $Q^2$ is 2,4-di-Cl-Ph and $R^2$ is Et. |
| 94E | $Q^2$ is 2,4-di-Cl-Ph and $R^2$ is CN. |
| 95E | $Q^2$ is 2,6-di-Cl-Ph and $R^2$ is Me. |
| 96E | $Q^2$ is 2,6-di-Cl-Ph and $R^2$ is Cl. |
| 97E | $Q^2$ is 2,6-di-Cl-Ph and $R^2$ is Br. |
| 98E | $Q^2$ is 2,6-di-Cl-Ph and $R^2$ is Et. |
| 99E | $Q^2$ is 2,6-di-Cl-Ph and $R^2$ is CN. |
| 100E | $Q^2$ is 2-F-4-MeO-Ph and $R^2$ is Me. |

-continued

| Table | Row Heading |
|---|---|
| 101E | $Q^2$ is 2-F-4-MeO-Ph and $R^2$ is Cl. |
| 102E | $Q^2$ is 2-F-4-MeO-Ph and $R^2$ is Br. |
| 103E | $Q^2$ is 2-F-4-MeO-Ph and $R^2$ is Et. |
| 104E | $Q^2$ is 2-F-4-MeO-Ph and $R^2$ is CN. |
| 105E | $Q^2$ is 2-F-4-EtO-Ph and $R^2$ is Me. |
| 106E | $Q^2$ is 2-F-4-EtO-Ph and $R^2$ is Cl. |
| 107E | $Q^2$ is 2-F-4-EtO-Ph and $R^2$ is Br. |
| 108E | $Q^2$ is 2-F-4-EtO-Ph and $R^2$ is Et. |
| 109E | $Q^2$ is 2-F-4-EtO-Ph and $R^2$ is CN. |
| 110E | $Q^2$ is 2-Cl-4-MeO-Ph and $R^2$ is Me. |
| 111E | $Q^2$ is 2-Cl-4-MeO-Ph and $R^2$ is Cl. |
| 112E | $Q^2$ is 2-Cl-4-MeO-Ph and $R^2$ is Br. |
| 113E | $Q^2$ is 2-Cl-4-MeO-Ph and $R^2$ is Et. |
| 114E | $Q^2$ is 2-Cl-4-MeO-Ph and $R^2$ is CN. |
| 115E | $Q^2$ is 2-Cl-4-EtO-Ph and $R^2$ is Me. |
| 116E | $Q^2$ is 2-Cl-4-EtO-Ph and $R^2$ is Cl. |
| 117E | $Q^2$ is 2-Cl-4-EtO-Ph and $R^2$ is Br. |
| 118E | $Q^2$ is 2-Cl-4-EtO-Ph and $R^2$ is Et. |
| 119E | $Q^2$ is 2-Cl-4-EtO-Ph and $R^2$ is CN. |
| 120E | $Q^2$ is 2-Br-4-MeO-Ph and $R^2$ is Me. |
| 121E | $Q^2$ is 2-Br-4-MeO-Ph and $R^2$ is Cl. |
| 122E | $Q^2$ is 2-Br-4-MeO-Ph and $R^2$ is Br. |
| 123E | $Q^2$ is 2-Br-4-MeO-Ph and $R^2$ is Et. |
| 124E | $Q^2$ is 2-Br-4-MeO-Ph and $R^2$ is CN. |
| 125E | $Q^2$ is 2-Br-4-EtO-Ph and $R^2$ is Me. |
| 126E | $Q^2$ is 2-Br-4-EtO-Ph and $R^2$ is Cl. |
| 127E | $Q^2$ is 2-Br-4-EtO-Ph and $R^2$ is Br. |
| 128E | $Q^2$ is 2-Br-4-EtO-Ph and $R^2$ is Et. |
| 129E | $Q^2$ is 2-Br-4-EtO-Ph and $R^2$ is CN. |
| 130E | $Q^2$ is 2-F-4-CN-Ph and $R^2$ is Me. |
| 131E | $Q^2$ is 2-F-4-CN-Ph and $R^2$ is Cl. |
| 132E | $Q^2$ is 2-F-4-CN-Ph and $R^2$ is Br. |
| 133E | $Q^2$ is 2-F-4-CN-Ph and $R^2$ is Et. |
| 134E | $Q^2$ is 2-F-4-CN-Ph and $R^2$ is CN. |
| 135E | $Q^2$ is 2-Cl-4-CN-Ph and $R^2$ is Me. |
| 136E | $Q^2$ is 2-Cl-4-CN-Ph and $R^2$ is Cl. |
| 137E | $Q^2$ is 2-Cl-4-CN-Ph and $R^2$ is Br. |
| 138E | $Q^2$ is 2-Cl-4-CN-Ph and $R^2$ is Et. |
| 139E | $Q^2$ is 2-Cl-4-CN-Ph and $R^2$ is CN. |
| 140E | $Q^2$ is 2-Br-4-CN-Ph and $R^2$ is Me. |
| 141E | $Q^2$ is 2-Br-4-CN-Ph and $R^2$ is Cl. |
| 142E | $Q^2$ is 2-Br-4-CN-Ph and $R^2$ is Br. |
| 143E | $Q^2$ is 2-Br-4-CN-Ph and $R^2$ is Et. |
| 144E | $Q^2$ is 2-Br-4-CN-Ph and $R^2$ is CN. |
| 145E | $Q^2$ is 3-Cl-2-pyridinyl and $R^2$ is Me. |
| 146E | $Q^2$ is 3-Cl-2-pyridinyl and $R^2$ is Cl. |
| 147E | $Q^2$ is 3-Cl-2-pyridinyl and $R^2$ is Br. |
| 148E | $Q^2$ is 3-Cl-2-pyridinyl and $R^2$ is Et. |
| 149E | $Q^2$ is 3-Cl-2-pyridinyl and $R^2$ is CN. |
| 150E | $Q^2$ is 3,5-di-Cl-2-pyridinyl and $R^2$ is Me. |
| 151E | $Q^2$ is 3,5-di-Cl-2-pyridinyl and $R^2$ is Cl. |
| 152E | $Q^2$ is 3,5-di-Cl-2-pyridinyl and $R^2$ is Br. |
| 153E | $Q^2$ is 3,5-di-Cl-2-pyridinyl and $R^2$ is Et. |
| 154E | $Q^2$ is 3,5-di-Cl-2-pyridinyl and $R^2$ is CN. |
| 155E | $Q^2$ is 2-Cl-3-thienyl and $R^2$ is Me. |
| 156E | $Q^2$ is 2-Cl-3-thienyl and $R^2$ is Cl. |
| 157E | $Q^2$ is 2-Cl-3-thienyl and $R^2$ is Br. |
| 158E | $Q^2$ is 2-Cl-3-thienyl and $R^2$ is Et. |
| 159E | $Q^2$ is 2-Cl-3-thienyl and $R^2$ is CN. |
| 160E | $Q^2$ is 2,5-di-Cl-3-thienyl and $R^2$ is Me. |
| 161E | $Q^2$ is 2,5-di-Cl-3-thienyl and $R^2$ is Cl. |
| 162E | $Q^2$ is 2,5-di-Cl-3-thienyl and $R^2$ is Br. |
| 163E | $Q^2$ is 2,5-di-Cl-3-thienyl and $R^2$ is Et. |
| 164E | $Q^2$ is 2,5-di-Cl-3-thienyl and $R^2$ is CN. |

Formulation/Utility

A compound of this invention will generally be used as a fungicidal active ingredient in a composition, i.e. formulation, with at least one additional component selected from the group consisting of surfactants, solid diluents and liquid diluents, which serves as a carrier. The formulation or composition ingredients are selected to be consistent with the physical properties of the active ingredient, mode of application and environmental factors such as soil type, moisture and temperature.

Useful formulations include both liquid and solid compositions. Liquid compositions include solutions (including emulsifiable concentrates), suspensions, emulsions (including microemulsions and/or suspoemulsions) and the like, which optionally can be thickened into gels. The general types of aqueous liquid compositions are soluble concentrate, suspension concentrate, capsule suspension, concentrated emulsion, microemulsion and suspo-emulsion. The general types of nonaqueous liquid compositions are emulsifiable concentrate, microemulsifiable concentrate, dispersible concentrate and oil dispersion.

The general types of solid compositions are dusts, powders, granules, pellets, prills, pastilles, tablets, filled films (including seed coatings) and the like, which can be water-dispersible ("wettable") or water-soluble. Films and coatings formed from film-forming solutions or flowable suspensions are particularly useful for seed treatment. Active ingredient can be (micro)encapsulated and further formed into a suspension or solid formulation; alternatively the entire formulation of active ingredient can be encapsulated (or "overcoated"). Encapsulation can control or delay release of the active ingredient. An emulsifiable granule combines the advantages of both an emulsifiable concentrate formulation and a dry granular formulation. High-strength compositions are primarily used as intermediates for further formulation.

Sprayable formulations are typically extended in a suitable medium before spraying.

Such liquid and solid formulations are formulated to be readily diluted in the spray medium, usually water. Spray volumes can range from about one to several thousand liters per hectare, but more typically are in the range from about ten to several hundred liters per hectare. Sprayable formulations can be tank mixed with water or another suitable medium for foliar treatment by aerial or ground application, or for application to the growing medium of the plant. Liquid and dry formulations can be metered directly into drip irrigation systems or metered into the furrow during planting. Liquid and solid formulations can be applied onto seeds of crops and other desirable vegetation as seed treatments before planting to protect developing roots and other subterranean plant parts and/or foliage through systemic uptake.

The formulations will typically contain effective amounts of active ingredient, diluent and surfactant within the following approximate ranges which add up to 100 percent by weight.

| | Weight Percent | | |
|---|---|---|---|
| | Active Ingredient | Diluent | Surfactant |
| Water-Dispersible and Water-soluble Granules, Tablets and Powders | 0.001-90 | 0-99.999 | 0-15 |
| Oil Dispersions, Suspensions, Emulsions, Solutions (including Emulsifiable Concentrates) | 1-50 | 40-99 | 0-50 |
| Dusts | 1-25 | 70-99 | 0-5 |
| Granules and Pellets | 0.001-95 | 5-99.999 | 0-15 |
| High Strength Compositions | 90-99 | 0-10 | 0-2 |

Solid diluents include, for example, clays such as bentonite, montmorillonite, attapulgite and kaolin, gypsum, cellulose, titanium dioxide, zinc oxide, starch, dextrin, sugars (e.g., lactose, sucrose), silica, talc, mica, diatomaceous earth, urea, calcium carbonate, sodium carbonate and bicarbonate, and sodium sulfate. Typical solid diluents are described in Watkins et al., *Handbook of Insecticide Dust Diluents and Carriers,* 2nd Ed., Dorland Books, Caldwell, N.J.

Liquid diluents include, for example, water, N,N-dimethylalkanamides (e.g., N,N-dimethylformamide), limonene, dimethyl sulfoxide, N-alkylpyrrolidones (e.g., N-methylpyrrolidinone), ethylene glycol, triethylene glycol, propylene glycol, dipropylene glycol, polypropylene glycol, propylene carbonate, butylene carbonate, paraffins (e.g., white mineral oils, normal paraffins, isoparaffins), alkylbenzenes, alkylnaphthalenes, glycerine, glycerol triacetate, sorbitol, aromatic hydrocarbons, dearomatized aliphatics, alkylbenzenes, alkylnaphthalenes, ketones such as cyclohexanone, 2-heptanone, isophorone and 4-hydroxy-4-methyl-2-pentanone, acetates such as isoamyl acetate, hexyl acetate, heptyl acetate, octyl acetate, nonyl acetate, tridecyl acetate and isobornyl acetate, other esters such as alkylated lactate esters, dibasic esters and γ-butyrolactone, and alcohols, which can be linear, branched, saturated or unsaturated, such as methanol, ethanol, n-propanol, isopropyl alcohol, n-butanol, isobutyl alcohol, n-hexanol, 2-ethylhexanol, n-octanol, decanol, isodecyl alcohol, isooctadecanol, cetyl alcohol, lauryl alcohol, tridecyl alcohol, oleyl alcohol, cyclohexanol, tetrahydrofurfuryl alcohol, diacetone alcohol and benzyl alcohol. Liquid diluents also include glycerol esters of saturated and unsaturated fatty acids (typically $C_6$-$C_{22}$), such as plant seed and fruit oils (e.g., oils of olive, castor, linseed, sesame, corn (maize), peanut, sunflower, grapeseed, safflower, cottonseed, soybean, rapeseed, coconut and palm kernel), animal-sourced fats (e.g., beef tallow, pork tallow, lard, cod liver oil, fish oil), and mixtures thereof. Liquid diluents also include alkylated fatty acids (e.g., methylated, ethylated, butylated) wherein the fatty acids may be obtained by hydrolysis of glycerol esters from plant and animal sources, and can be purified by distillation. Typical liquid diluents are described in Marsden, *Solvents Guide,* 2nd Ed., Interscience, New York, 1950.

The solid and liquid compositions of the present invention often include one or more surfactants. When added to a liquid, surfactants (also known as "surface-active agents") generally modify, most often reduce, the surface tension of the liquid. Depending on the nature of the hydrophilic and lipophilic groups in a surfactant molecule, surfactants can be useful as wetting agents, dispersants, emulsifiers or defoaming agents.

Surfactants can be classified as nonionic, anionic or cationic. Nonionic surfactants useful for the present compositions include, but are not limited to: alcohol alkoxylates such as alcohol alkoxylates based on natural and synthetic alcohols (which may be branched or linear) and prepared from the alcohols and ethylene oxide, propylene oxide, butylene oxide or mixtures thereof; amine ethoxylates, alkanolamides and ethoxylated alkanolamides; alkoxylated triglycerides such as ethoxylated soybean, castor and rapeseed oils; alkylphenol alkoxylates such as octylphenol ethoxylates, nonylphenol ethoxylates, dinonyl phenol ethoxylates and dodecyl phenol ethoxylates (prepared from the phenols and ethylene oxide, propylene oxide, butylene oxide or mixtures thereof); block polymers prepared from ethylene oxide or propylene oxide and reverse block polymers where the terminal blocks are prepared from propylene oxide; ethoxylated fatty acids; ethoxylated fatty esters and oils; ethoxylated methyl esters; ethoxylated tristyrylphenol (including those prepared from ethylene oxide, propylene oxide, butylene oxide or mixtures thereof); fatty acid esters, glycerol esters, lanolin-based derivatives, polyethoxylate esters such as polyethoxylated sorbitan fatty acid esters, polyethoxylated sorbitol fatty acid esters and polyethoxylated glycerol fatty acid esters; other sorbitan derivatives such as sorbitan esters; polymeric surfactants such as random copolymers, block copolymers, alkyd peg (polyethylene glycol) resins, graft or comb polymers and star polymers; polyethylene glycols (pegs); polyethylene glycol fatty acid esters; silicone-based surfactants; and sugar-derivatives such as sucrose esters, alkyl polyglycosides and alkyl polysaccharides.

Useful anionic surfactants include, but are not limited to: alkylaryl sulfonic acids and their salts; carboxylated alcohol or alkylphenol ethoxylates; diphenyl sulfonate derivatives; lignin and lignin derivatives such as lignosulfonates; maleic or succinic acids or their anhydrides; olefin sulfonates; phosphate esters such as phosphate esters of alcohol alkoxylates, phosphate esters of alkylphenol alkoxylates and phosphate esters of styryl phenol ethoxylates; protein-based surfactants; sarcosine derivatives; styryl phenol ether sulfate; sulfates and sulfonates of oils and fatty acids; sulfates and sulfonates of ethoxylated alkylphenols; sulfates of alcohols; sulfates of ethoxylated alcohols; sulfonates of amines and amides such as N,N-alkyltaurates; sulfonates of benzene, cumene, toluene, xylene, and dodecyl and tridecylbenzenes; sulfonates of condensed naphthalenes; sulfonates of naphthalene and alkyl naphthalene; sulfonates of fractionated petroleum; sulfosuccinamates; and sulfosuccinates and their derivatives such as dialkyl sulfosuccinate salts.

Useful cationic surfactants include, but are not limited to: amides and ethoxylated amides; amines such as N-alkyl propanediamines, tripropylenetriamines and dipropylenetetramines, and ethoxylated amines, ethoxylated diamines and propoxylated amines (prepared from the amines and ethylene oxide, propylene oxide, butylene oxide or mixtures thereof); amine salts such as amine acetates and diamine salts; quaternary ammonium salts such as quaternary salts, ethoxylated quaternary salts and diquaternary salts; and amine oxides such as alkyldimethylamine oxides and bis-(2-hydroxyethyl)-alkylamine oxides.

Also useful for the present compositions are mixtures of nonionic and anionic surfactants or mixtures of nonionic and cationic surfactants. Nonionic, anionic and cationic surfactants and their recommended uses are disclosed in a variety of published references including *McCutcheon's Emulsifiers and Detergents*, annual American and International Editions published by McCutcheon's Division, The Manufacturing Confectioner Publishing Co.; Sisely and Wood, *Encyclopedia of Surface Active Agents*, Chemical Publ. Co., Inc., New York, 1964; and A. S. Davidson and B. Milwidsky, *Synthetic Detergents*, Seventh Edition, John Wiley and Sons, New York, 1987.

Compositions of this invention may also contain formulation auxiliaries and additives, known to those skilled in the art as formulation aids (some of which may be considered to also function as solid diluents, liquid diluents or surfactants). Such formulation auxiliaries and additives may control: pH (buffers), foaming during processing (antifoams such polyorganosiloxanes), sedimentation of active ingredients (suspending agents), viscosity (thixotropic thickeners), in-container microbial growth (antimicrobials), product freezing (antifreezes), color (dyes/pigment dispersions), wash-off (film formers or stickers), evaporation (evaporation retardants), and other formulation attributes. Film formers include, for example, polyvinyl acetates, polyvinyl acetate copolymers, polyvinylpyrrolidone-vinyl acetate copolymer, polyvinyl alcohols, polyvinyl alcohol copolymers and waxes. Examples of formulation auxiliaries and additives include those listed in *McCutcheon's Volume 2: Functional Materials*, annual International and North American editions published by McCutcheon's Division, The Manufacturing Confectioner Publishing Co.; and PCT Publication WO 03/024222.

The compound of Formula 1 or Formula 1A and any other active ingredients are typically incorporated into the present compositions by dissolving the active ingredient in a solvent or by grinding in a liquid or dry diluent. Solutions, including emulsifiable concentrates, can be prepared by simply mixing the ingredients. If the solvent of a liquid composition intended for use as an emulsifiable concentrate is water-immiscible, an emulsifier is typically added to emulsify the active-containing solvent upon dilution with water. Active ingredient slurries, with particle diameters of up to 2,000 μm can be wet milled using media mills to obtain particles with average diameters below 3 μm. Aqueous slurries can be made into finished suspension concentrates (see, for example, U.S. Pat. No. 3,060,084) or further processed by spray drying to form water-dispersible granules. Dry formulations usually require dry milling processes, which produce average particle diameters in the 2 to 10 μm range. Dusts and powders can be prepared by blending and usually grinding (such as with a hammer mill or fluid-energy mill). Granules and pellets can be prepared by spraying the active material upon preformed granular carriers or by agglomeration techniques. See Browning, "Agglomeration", Chemical Engineering, Dec. 4, 1967, pp 147-48, *Perry's Chemical Engineer's Handbook*, 4th Ed., McGraw-Hill, New York, 1963, pages 8-57 and following, and WO 91/13546. Pellets can be prepared as described in U.S. Pat. No. 4,172,714. Water-dispersible and water-soluble granules can be prepared as taught in U.S. Pat. No. 4,144,050, U.S. Pat. No. 3,920,442 and DE 3,246,493. Tablets can be prepared as taught in U.S. Pat. No. 5,180,587, U.S. Pat. No. 5,232,701 and U.S. Pat. No. 5,208,030. Films can be prepared as taught in GB 2,095,558 and U.S. Pat. No. 3,299,566.

For further information regarding the art of formulation, see T. S. Woods, "The Formulator's Toolbox—Product Forms for Modern Agriculture" in *Pesticide Chemistry and Bioscience, The Food-Environment Challenge*, T. Brooks and T. R. Roberts, Eds., Proceedings of the 9th International Congress on Pesticide Chemistry, The Royal Society of Chemistry, Cambridge, 1999, pp. 120-133. See also U.S. Pat. No. 3,235,361, Col. 6, line 16 through Col. 7, line 19 and Examples 10-41; U.S. Pat. No. 3,309,192, Col. 5, line 43 through Col. 7, line 62 and Examples 8, 12, 15, 39, 41, 52, 53, 58, 132, 138-140, 162-164, 166, 167 and 169-182; U.S. Pat. No. 2,891,855, Col. 3, line 66 through Col. 5, line 17 and Examples 1-4; Klingman, *Weed Control as a Science*, John Wiley and Sons, Inc., New York, 1961, pp 81-96; Hance et al., *Weed Control Handbook*, 8th Ed., Blackwell Scientific Publications, Oxford, 1989; and *Developments in formulation technology*, PJB Publications, Richmond, UK, 2000.

In the following Examples, all percentages are by weight and all formulations are prepared in conventional ways. Compound numbers refer to compounds in Index Tables A-C. Without further elaboration, it is believed that one skilled in the art using the preceding description can utilize the present invention to its fullest extent. The following Examples are, therefore, to be constructed as merely illustrative, and not limiting of the disclosure in any way whatsoever. Percentages are by weight except where otherwise indicated.

Example A

| High Strength Concentrate | |
|---|---|
| Compound 10 | 98.5% |
| silica aerogel | 0.5% |
| synthetic amorphous fine silica | 1.0% |

Example B

| Wettable Powder | |
|---|---|
| Compound 3 | 65.0% |
| dodecylphenol polyethylene glycol ether | 2.0% |
| sodium ligninsulfonate | 4.0% |
| sodium silicoaluminate | 6.0% |
| montmorillonite (calcined) | 23.0% |

Example C

| Granule | |
|---|---|
| Compound 10 | 10.0% |
| attapulgite granules (low volatile matter, 0.71/0.30 mm; U.S.S. No. 25-50 sieves) | 90.0% |

Example D

| Extruded Pellet | |
|---|---|
| Compound 14 | 25.0% |
| anhydrous sodium sulfate | 10.0% |
| crude calcium ligninsulfonate | 5.0% |
| sodium alkylnaphthalenesulfonate | 1.0% |
| calcium/magnesium bentonite | 59.0% |

Example E

| Emulsifiable Concentrate | |
|---|---|
| Compound 3 | 10.0% |
| polyoxyethylene sorbitol hexoleate | 20.0% |
| $C_6$-$C_{10}$ fatty acid methyl ester | 70.0% |

Example F

| Microemulsion | |
|---|---|
| Compound 10 | 5.0% |
| polyvinylpyrrolidone-vinyl acetate copolymer | 30.0% |
| alkylpolyglycoside | 30.0% |
| glyceryl monooleate | 15.0% |
| water | 20.0% |

Example G

| Seed Treatment | |
|---|---|
| Compound 14 | 20.00% |
| polyvinylpyrrolidone-vinyl acetate copolymer | 5.00% |
| montan acid wax | 5.00% |
| calcium ligninsulfonate | 1.00% |
| polyoxyethylene/polyoxypropylene block copolymers | 1.00% |
| stearyl alcohol (POE 20) | 2.00% |
| polyorganosilane | 0.20% |
| colorant red dye | 0.05% |
| water | 65.75% |

Water-soluble and water-dispersible formulations are typically diluted with water to form aqueous compositions before application. Aqueous compositions for direct applications to the plant or portion thereof (e.g., spray tank compositions) typically at least about 1 ppm or more (e.g., from 1 ppm to 100 ppm) of the compound(s) of this invention.

The compounds of this invention are useful as plant disease control agents. The present invention therefore further comprises a method for controlling plant diseases caused by fungal plant pathogens comprising applying to the plant or portion thereof to be protected, or to the plant seed to be protected, an effective amount of a compound of the invention or a fungicidal composition containing said compound. The compounds and/or compositions of this invention provide control of diseases caused by a broad spectrum of fungal plant pathogens in the Basidiomycete, Ascomycete, Oomycete and Deuteromycete classes. They are effective in controlling a broad spectrum of plant diseases, particularly foliar pathogens of ornamental, turf, vegetable, field, cereal, and fruit crops. These pathogens include: Oomycetes, including *Phytophthora* diseases such as *Phytophthora infestans, Phytophthora megasperma, Phytophthora parasitica, Phytophthora cinnamomi* and *Phytophthora capsici, Pythium* diseases such as *Pythium aphanidermatum*, and diseases in the Peronosporaceae family such as *Plasmopara viticola, Peronospora* spp. (including *Peronospora tabacina* and *Peronospora parasitica*), *Pseudoperonospora* spp. (including *Pseudoperonospora cubensis*) and *Bremia lactucae*; Ascomycetes, including *Alternaria* diseases such as *Alternaria solani* and *Alternaria brassicae, Guignardia* diseases such as *Guignardia bidwell, Venturia* diseases such as *Venturia inaequalis, Septoria* diseases such as *Septoria nodorum* and *Septoria tritici*, powdery mildew diseases such as *Erysiphe* spp. (including *Erysiphe graminis* and *Erysiphe polygoni*), *Uncinula necatur, Sphaerotheca fuligena* and *Podosphaera leucotricha, Pseudocercosporella herpotrichoides, Botrytis* diseases such as *Botrytis cinerea, Monilinia fructicola, Sclerotinia* diseases such as *Sclerotinia sclerotiorum, Magnaporthe grisea, Phomopsis viticola, Helminthosporium* diseases such as *Helminthosporium tritici repentis, Pyrenophora teres*, anthracnose diseases such as *Glomerella* or *Colletotrichum* spp. (such as *Colletotrichum graminicola* and *Colletotrichum orbiculare*), and *Gaeumannomyces graminis;* Basidiomycetes, including rust diseases caused by *Puccinia* spp. (such as *Puccinia recondite, Puccinia striiformis, Puccinia hordei, Puccinia graminis* and *Puccinia arachidis*), *Hemileia vastatrix* and *Phakopsora pachyrhizi*; other pathogens including *Rutstroemia floccosum* (also known as *Sclerontina homoeocarpa*); *Rhizoctonia* spp. (such as *Rhizoctonia solani*); *Fusarium* diseases such as *Fusarium roseum, Fusarium graminearum* and *Fusarium oxysporum; Verticillium dahliae; Sclerotium rolfsii; Rynchosporium secalis; Cercosporidium personatum, Cercospora arachidicola* and *Cercospora beticola*; and other genera and species closely related to these pathogens. In addition to their fungicidal activity, the compositions or combinations also have activity against bacteria such as *Erwinia amylovora, Xanthomonas campestris, Pseudomonas syringae,* and other related species.

Plant disease control is ordinarily accomplished by applying an effective amount of a compound of this invention either pre- or post-infection, to the portion of the plant to be protected such as the roots, stems, foliage, fruit, seeds, tubers or bulbs, or to the media (soil or sand) in which the plants to be protected are growing. The compounds can also be applied to seeds to protect the seeds and seedlings developing from the seeds. The compounds can also be applied through irrigation water to treat plants.

Rates of application for these compounds (i.e. a fungicidally effective amount) can be influenced by factors such as the plant diseases to be controlled, the plant species to be protected, ambient moisture and temperature and should be determined under actual use conditions. One skilled in the art can easily determine through simple experimentation the fungicidally effective amount necessary for the desired level of plant disease control. Foliage can normally be protected when treated at a rate of from less than about 1 g/ha to about 5,000 g/ha of active ingredient. Seed and seedlings can normally be protected when seed is treated at a rate of from about 0.1 to about 10 g per kilogram of seed.

Compounds of this invention can also be mixed with one or more other biologically active compounds or agents including fungicides, insecticides, nematocides, bactericides, acaricides, herbicides, herbicide safeners, growth regulators such as insect molting inhibitors and rooting stimulants, chemosterilants, semiochemicals, repellents, attractants, pheromones, feeding stimulants, plant nutrients, other biologically active compounds or entomopathogenic bacteria, virus or fungi to form a multi-component pesticide giving an even broader spectrum of agricultural protection. Thus the present invention also pertains to a composition comprising a compound of Formula 1 or Formula 1A (in a fungicidally effective amount) and at least one additional biologically active compound or agent (in a biologically effective amount) and can further comprise at least one of a surfactant, a solid diluent or a liquid diluent. The other biologically active compounds or agents can be formulated in compositions comprising at least one of a surfactant, solid or liquid diluent. For mixtures of the present invention, one or more other biologically active compounds or agents can be formulated together with a compound of Formula 1 or Formula 1A, to form a premix, or one or more other biologically active compounds or agents can be formulated separately from the compound of Formula 1 or Formula 1A, and the formulations combined together before application (e.g., in a spray tank) or, alternatively, applied in succession.

Of note is a composition which in addition to the compound of Formula 1 or Formula 1A include at least one fungicidal compound selected from the group consisting of the classes (1) methyl benzimidazole carbamate (MBC) fungicides; (2) dicarboximide fungicides; (3) demethylation inhibitor (DMI) fungicides; (4) phenylamide fungicides; (5) amine/morpholine fungicides; (6) phospholipid biosynthesis inhibitor fungicides; (7) carboxamide fungicides; (8) hydroxy(2-amino-)pyrimidine fungicides; (9) anilinopyrimidine fungicides; (10) N-phenyl carbamate fungicides; (11) quinone outside inhibitor (QoI) fungicides; (12) phenylpyrrole fungicides; (13) quinoline fungicides; (14) lipid peroxidation inhibitor fungicides; (15) melanin biosynthesis inhibitors-reductase (MBI-R) fungicides; (16) melanin biosynthesis inhibitors-dehydratase (MBI-D) fungicides; (17) hydroxyanilide fungicides; (18) squalene-epoxidase inhibitor fungicides; (19) polyoxin fungicides; (20) phenylurea fungicides; (21) quinone inside inhibitor (QiI) fungicides; (22) benzamide fungicides; (23) enopyranuronic acid antibiotic fungicides; (24) hexopyranosyl antibiotic fungicides; (25) glucopyranosyl antibiotic: protein synthesis fungicides; (26) glucopyranosyl antibiotic: trehalase and inositol biosynthesis fungicides; (27) cyanoacetamideoxime fungicides; (28) carbamate fungicides; (29) oxidative phosphorylation uncoupling fungicides; (30) organo tin fungicides; (31) carboxylic acid fungicides; (32) heteroaromatic fungicides;

(33) phosphonate fungicides; (34) phthalamic acid fungicides; (35) benzotriazine fungicides; (36) benzene-sulfonamide fungicides; (37) pyridazinone fungicides; (38) thiophene-carboxamide fungicides; (39) pyrimidinamide fungicides; (40) carboxylic acid amide (CAA) fungicides; (41) tetracycline antibiotic fungicides; (42) thiocarbamate fungicides; (43) benzamide fungicides; (44) host plant defense induction fungicides; (45) multi-site contact activity fungicides; (46) fungicides other than classes (1) through (45); and salts of compounds of classes (1) through (46).

Further descriptions of these classes of fungicidal compounds are provided below.

(1) "Methyl benzimidazole carbamate (MBC) fungicides" (Fungicide Resistance Action Committee (FRAC) code 1) inhibit mitosis by binding to β-tubulin during microtubule assembly. Inhibition of microtubule assembly can disrupt cell division, transport within the cell and cell structure. Methyl benzimidazole carbamate fungicides include benzimidazole and thiophanate fungicides. The benzimidazoles include benomyl, carbendazim, fuberidazole and thiabendazole. The thiophanates include thiophanate and thiophanate-methyl.

(2) "Dicarboximide fungicides" (Fungicide Resistance Action Committee (FRAC) code 2) are proposed to inhibit a lipid peroxidation in fungi through interference with NADH cytochrome c reductase. Examples include chlozolinate, iprodione, procymidone and vinclozo lin.

(3) "Demethylation inhibitor (DMI) fungicides" (Fungicide Resistance Action Committee (FRAC) code 3) inhibit C14-demethylase, which plays a role in sterol production. Sterols, such as ergosterol, are needed for membrane structure and function, making them essential for the development of functional cell walls. Therefore, exposure to these fungicides results in abnormal growth and eventually death of sensitive fungi. DMI fungicides are divided between several chemical classes: azoles (including triazoles and imidazoles), pyrimidines, piperazines and pyridines. The triazoles include azaconazole, bitertanol, bromuconazole, cyproconazole, difenoconazole, diniconazole (including diniconazole-M), epoxiconazole, fenbuconazole, fluquinconazole, flusilazole, flutriafol, hexaconazole, imibenconazole, ipconazole, metconazole, myclobutanil, penconazole, propiconazole, prothioconazole, simeconazole, tebuconazole, tetraconazole, triadimefon, triadimenol, triticonazole and uniconazole. The imidazoles include clotrimazole, imazalil, oxpoconazole, prochloraz, pefurazoate and triflumizole. The pyrimidines include fenarimol and nuarimol. The piperazines include triforine. The pyridines include pyrifenox. Biochemical investigations have shown that all of the above mentioned fungicides are DMI fungicides as described by K. H. Kuck et al. in *Modern Selective Fungicides—Properties, applications and Mechanisms of Action*, H. Lyr (Ed.), Gustav Fischer Verlag: New York, 1995, 205-258.

(4) "Phenylamide fungicides" (Fungicide Resistance Action Committee (FRAC) code 4) are specific inhibitors of RNA polymerase in Oomycete fungi. Sensitive fungi exposed to these fungicides show a reduced capacity to incorporate uridine into rRNA. Growth and development in sensitive fungi is prevented by exposure to this class of fungicide. Phenylamide fungicides include acylalanine, oxazolidinone and butyrolactone fungicides. The acylalanines include benalaxyl, benalaxyl-M, furalaxyl, metalaxyl and metalaxyl-M/mefenoxam. The oxazolidinones include oxadixyl. The butyrolactones include ofurace.

(5) "Amine/morpholine fungicides" (Fungicide Resistance Action Committee (FRAC) code 5) inhibit two target sites within the sterol biosynthetic pathway, $\Delta^8 \rightarrow \Delta^7$ isomerase and $\Delta^{14}$ reductase. Sterols, such as ergosterol, are needed for membrane structure and function, making them essential for the development of functional cell walls. Therefore, exposure to these fungicides results in abnormal growth and eventually death of sensitive fungi. Amine/morpholine fungicides (also known as non-DMI sterol biosynthesis inhibitors) include morpholine, piperidine and spiroketal-amine fungicides. The morpholines include aldimorph, dodemorph, fenpropimorph, tridemorph and trimorphamide. The piperidines include fenpropidin and piperalin. The spiroketal-amines include spiroxamine.

(6) "Phospholipid biosynthesis inhibitor fungicides" (Fungicide Resistance Action Committee (FRAC) code 6) inhibit growth of fungi by affecting phospholipid biosynthesis. Phospholipid biosynthesis fungicides include phosphorothiolate and dithiolane fungicides. The phosphorothiolates include edifenphos, iprobenfos and pyrazophos. The dithiolanes include isoprothiolane.

(7) "Carboxamide fungicides" (Fungicide Resistance Action Committee (FRAC) code 7) inhibit Complex II (succinate dehydrogenase) fungal respiration by disrupting a key enzyme in the Krebs Cycle (TCA cycle) named succinate dehydrogenase. Inhibiting respiration prevents the fungus from making ATP, and thus inhibits growth and reproduction. Carboxamide fungicides include benzamides, furan carboxamides, oxathiin carboxamides, thiazole carboxamides, pyrazole carboxamides and pyridine carboxamides. The benzamides include benodanil, flutolanil and mepronil. The furan carboxamides include fenfuram. The oxathiin carboxamides include carboxin and oxycarboxin. The thiazole carboxamides include thifluzamide. The pyrazole carboxamides include furametpyr, penthiopyrad, bixafen, isopyrazam, N-[2-(1S,2R)-[1,1'-bicyclopropyl]-2-ylphenyl]-3-(difluoromethyl)-1-methyl-1H-pyrazole-4-carboxamide and penflufen (N-[2-(1,3-dimethyl-butyl)phenyl]-5-fluoro-1,3-dimethyl-1H-pyrazole-4-carboxamide). The pyridine carboxamides include boscalid.

(8) "Hydroxy(2-amino-)pyrimidine fungicides" (Fungicide Resistance Action Committee (FRAC) code 8) inhibit nucleic acid synthesis by interfering with adenosine deaminase. Examples include bupirimate, dimethirimol and ethirimol.

(9) "Anilinopyrimidine fungicides" (Fungicide Resistance Action Committee (FRAC) code 9) are proposed to inhibit biosynthesis of the amino acid methionine and to disrupt the secretion of hydrolytic enzymes that lyse plant cells during infection. Examples include cyprodinil, mepanipyrim and pyrimethanil.

(10) "N-Phenyl carbamate fungicides" (Fungicide Resistance Action Committee (FRAC) code 10) inhibit mitosis by binding to β-tubulin and disrupting microtubule assembly. Inhibition of microtubule assembly can disrupt cell division, transport within the cell and cell structure. Examples include diethofencarb.

(11) "Quinone outside inhibitor (QoI) fungicides" (Fungicide Resistance Action Committee (FRAC) code 11) inhibit Complex III mitochondrial respiration in fungi by affecting ubiquinol oxidase. Oxidation of ubiquinol is blocked at the "quinone outside" ($Q_o$) site of the cytochrome $bc_1$ complex, which is located in the inner mitochondrial membrane of fungi. Inhibiting mitochondrial respiration prevents normal fungal growth and development. Quinone outside inhibitor fungicides (also known as strobilurin fungicides) include methoxyacrylate, methoxycarbamate, oximinoacetate, oximinoacetamide, oxazolidinedione, dihydrodioxazine, imidazolinone and benzylcarbamate fungicides. The methoxyacrylates include azoxystrobin, enestroburin (SYP-Z071), picoxystrobin and pyraoxystrobin (SYP-3343). The methoxycarbamates include pyraclostrobin and pyrametostrobin (SYP-4155). The oximinoacetates include kresoxim-methyl and trifloxystrobin. The oximinoacetamides include dimoxystrobin, metominostrobin, orysastrobin, α-[methoxy-imino]-N-methyl-2-[[[1-[3-(trifluoromethyl)phenyl]ethoxy]imino]-methyl]benzeneacetamide and 2-[[[3-(2,6-dichlorophenyl)-1-methyl-2-propen-1-ylidene]-amino]oxy]methyl]-α-(methoxyimino)-N-methylbenzeneacetamide. The oxazolidinediones include famoxadone. The dihydrodioxazines include fluoxastrobin. The imidazolinones include fenamidone. The benzylcarbamates include pyribencarb.

(12) "Phenylpyrrole fungicides" (Fungicide Resistance Action Committee (FRAC) code 12) inhibit a MAP protein kinase associated with osmotic signal transduction in fungi. Fenpiclonil and fludioxonil are examples of this fungicide class.

(13) "Quinoline fungicides" (Fungicide Resistance Action Committee (FRAC) code 13) are proposed to inhibit signal transduction by affecting G-proteins in early cell signaling. They have been shown to interfere with germination and/or appressorium formation in fungi that cause powder mildew diseases. Quinoxyfen and tebufloquin are examples of this class of fungicide.

(14) "Lipid peroxidation inhibitor fungicides" (Fungicide Resistance Action Committee (FRAC) code 14) are proposed to inhibit lipid peroxidation which affects membrane synthesis in fungi. Members of this class, such as etridiazole, may also affect other biological processes such as respiration and melanin biosynthesis. Lipid peroxidation fungicides include aromatic carbon and 1,2,4-thiadiazole fungicides. The aromatic carbon fungicides include biphenyl, chloroneb, dicloran, quintozene, tecnazene and tolclofos-methyl. The 1,2,4-thiadiazole fungicides include etridiazole.

(15) "Melanin biosynthesis inhibitors-reductase (MBI-R) fungicides" (Fungicide Resistance Action Committee (FRAC) code 16.1) inhibit the naphthal reduction step in melanin biosynthesis. Melanin is required for host plant infection by some fungi. Melanin biosynthesis inhibitors-reductase fungicides include isobenzofuranone, pyrroloquinolinone and triazolobenzothiazole fungicides. The isobenzofuranones include fthalide. The pyrroloquinolinones include pyroquilon. The triazolobenzothiazoles include tricyclazole.

(16) "Melanin biosynthesis inhibitors-dehydratase (MBI-D) fungicides" (Fungicide Resistance Action Committee (FRAC) code 16.2) inhibit scytalone dehydratase in melanin biosynthesis. Melanin in required for host plant infection by some fungi. Melanin biosynthesis inhibitors-dehydratase fungicides include cyclopropanecarboxamide, carboxamide and propionamide fungicides. The cyclopropanecarboxamides include carpropamid. The carboxamides include diclocymet. The propionamides include fenoxanil.

(17) "Hydroxyanilide fungicides (Fungicide Resistance Action Committee (FRAC) code 17) inhibit C4-demethylase which plays a role in sterol production. Examples include fenhexamid.

(18) "Squalene-epoxidase inhibitor fungicides" (Fungicide Resistance Action Committee (FRAC) code 18) inhibit squalene-epoxidase in ergosterol biosynthesis pathway. Sterols such as ergosterol are needed for membrane structure and function, making them essential for the development of functional cell walls. Therefore exposure to these fungicides results in abnormal growth and eventually death of sensitive fungi. Squalene-epoxidase inhibitor fungicides include thiocarbamate and allylamine fungicides. The thiocarbamates include pyributicarb. The allylamines include naftifine and terbinafine.

(19) "Polyoxin fungicides" (Fungicide Resistance Action Committee (FRAC) code 19) inhibit chitin synthase. Examples include polyoxin.

(20) "Phenylurea fungicides" (Fungicide Resistance Action Committee (FRAC) code 20) are proposed to affect cell division. Examples include pencycuron.

(21) "Quinone inside inhibitor (QiI) fungicides" (Fungicide Resistance Action Committee (FRAC) code 21) inhibit Complex III mitochondrial respiration in fungi by affecting ubiquinol reductase. Reduction of ubiquinol is blocked at the "quinone inside" ($Q_i$) site of the cytochrome $bc_1$ complex, which is located in the inner mitochondrial membrane of fungi. Inhibiting mitochondrial respiration prevents normal fungal growth and development. Quinone inside inhibitor fungicides include cyanoimidazole and sulfamoyltriazole fungicides. The cyanoimidazoles include cyazofamid. The sulfamoyltriazoles include amisulbrom.

(22) "Benzamide fungicides" (Fungicide Resistance Action Committee (FRAC) code 22) inhibit mitosis by binding to β-tubulin and disrupting microtubule assembly Inhibition of microtubule assembly can disrupt cell division, transport within the cell and cell structure. Examples include zoxamide.

(23) "Enopyranuronic acid antibiotic fungicides" (Fungicide Resistance Action Committee (FRAC) code 23) inhibit growth of fungi by affecting protein biosynthesis. Examples include blasticidin-S.

(24) "Hexopyranosyl antibiotic fungicides" (Fungicide Resistance Action Committee (FRAC) code 24) inhibit growth of fungi by affecting protein biosynthesis. Examples include kasugamycin.

(25) "Glucopyranosyl antibiotic: protein synthesis fungicides" (Fungicide Resistance Action Committee (FRAC) code 25) inhibit growth of fungi by affecting protein biosynthesis. Examples include streptomycin.

(26) "Glucopyranosyl antibiotic: trehalase and inositol biosynthesis fungicides" (Fungicide Resistance Action Committee (FRAC) code 26) inhibit trehalase in inositol biosynthesis pathway. Examples include validamycin.

(27) "Cyanoacetamideoxime fungicides (Fungicide Resistance Action Committee (FRAC) code 27) include cymoxanil.

(28) "Carbamate fungicides" (Fungicide Resistance Action Committee (FRAC) code 28) are considered multi-site inhibitors of fungal growth. They are proposed to interfere with the synthesis of fatty acids in cell membranes, which then disrupts cell membrane permeability. Propamacarb, propamacarb-hydrochloride, iodocarb, and prothiocarb are examples of this fungicide class.

(29) "Oxidative phosphorylation uncoupling fungicides" (Fungicide Resistance Action Committee (FRAC) code 29) inhibit fungal respiration by uncoupling oxidative phosphorylation. Inhibiting respiration prevents normal fungal growth and development. This class includes 2,6-dinitroanilines such as fluazinam, pyrimidonehydrazones such as ferimzone and dinitrophenyl crotonates such as dinocap, meptyldinocap and binapacryl.

(30) "Organo tin fungicides" (Fungicide Resistance Action Committee (FRAC) code 30) inhibit adenosine triphosphate (ATP) synthase in oxidative phosphorylation pathway. Examples include fentin acetate, fentin chloride and fentin hydroxide.

(31) "Carboxylic acid fungicides" (Fungicide Resistance Action Committee (FRAC) code 31) inhibit growth of fungi by affecting deoxyribonucleic acid (DNA) topoisomerase type II (gyrase). Examples include oxolinic acid.

(32) "Heteroaromatic fungicides" (Fungicide Resistance Action Committee (FRAC) code 32) are proposed to affect DNA/ribonucleic acid (RNA) synthesis. Heteroaromatic fungicides include isoxazole and isothiazolone fungicides. The isoxazoles include hymexazole and the isothiazolones include octhilinone.

(33) "Phosphonate fungicides" (Fungicide Resistance Action Committee (FRAC) code 33) include phosphorous acid and its various salts, including fosetyl-aluminum.

(34) "Phthalamic acid fungicides" (Fungicide Resistance Action Committee (FRAC) code 34) include teclofthalam.

(35) "Benzotriazine fungicides" (Fungicide Resistance Action Committee (FRAC) code 35) include triazoxide.

(36) "Benzene-sulfonamide fungicides" (Fungicide Resistance Action Committee (FRAC) code 36) include flusulfamide.

(37) "Pyridazinone fungicides" (Fungicide Resistance Action Committee (FRAC) code 37) include diclomezine.

(38) "Thiophene-carboxamide fungicides" (Fungicide Resistance Action Committee (FRAC) code 38) are proposed to affect ATP production. Examples include silthiofam.

(39) "Pyrimidinamide fungicides" (Fungicide Resistance Action Committee (FRAC) code 39) inhibit growth of fungi by affecting phospholipid biosynthesis and include diflumetorim.

(40) "Carboxylic acid amide (CAA) fungicides" (Fungicide Resistance Action Committee (FRAC) code 40) are proposed to inhibit phospholipid biosynthesis and cell wall deposition. Inhibition of these processes prevents growth and leads to death of the target fungus. Carboxylic acid amide fungicides include cinnamic acid amide, valinamide carbamate and mandelic acid amide fungicides. The cinnamic acid amides include dimethomorph and flumorph. The valinamide carbamates include benthiavalicarb, benthiavalicarb-isopropyl, iprovalicarb, valifenalate and valiphenal. The mandelic acid amides include mandipropamid, N-[2-[4-[[3-(4-chlorophenyl)-2-propyn-1-yl]oxy]-3-methoxyphenyl]ethyl]-3-methyl-2-[(methylsulfonyl)amino]butanamide and N-[2-[4-[[3-(4-chlorophenyl)-2-propyn-1-yl]oxy]-3-methoxyphenyl]ethyl]-3-methyl-2-[(ethylsulfonyl)amino]butanamide.

(41) "Tetracycline antibiotic fungicides" (Fungicide Resistance Action Committee (FRAC) code 41) inhibit growth of fungi by affecting complex 1 nicotinamide adenine dinucleotide (NADH) oxidoreductase. Examples include oxytetracycline.

(42) "Thiocarbamate fungicides" (Fungicide Resistance Action Committee (FRAC) code 42) include methasulfocarb.

(43) "Benzamide fungicides" (Fungicide Resistance Action Committee (FRAC) code 43) inhibit growth of fungi by delocalization of spectrin-like proteins. Examples include acylpicolide fungicides such as fluopicolide and fluopyram.

(44) "Host plant defense induction fungicides" (Fungicide Resistance Action Committee (FRAC) code P) induce host plant defense mechanisms. Host plant defense induction fungicides include benzo-thiadiazole, benzisothiazole and thiadiazole-carboxamide fungicides. The benzo-thiadiazoles include acibenzolar-5-methyl. The benzisothiazoles include probenazole. The thiadiazole-carboxamides include tiadinil and isotianil.

(45) "Multi-site contact fungicides" inhibit fungal growth through multiple sites of action and have contact/preventive activity. This class of fungicides includes: (45.1) "copper fungicides" (Fungicide Resistance Action Committee (FRAC) code M1)", (45.2) "sulfur fungicides" (Fungicide Resistance Action Committee (FRAC) code M2), (45.3) "dithiocarbamate fungicides" (Fungicide Resistance Action Committee (FRAC) code M3), (45.4) "phthalimide fungicides" (Fungicide Resistance Action Committee (FRAC) code M4), (45.5) "chloronitrile fungicides" (Fungicide Resistance Action Committee (FRAC) code M5), (45.6) "sulfamide fungicides" (Fungicide Resistance Action Committee (FRAC) code M6), (45.7) "guanidine fungicides" (Fungicide Resistance Action Committee (FRAC) code M7), (45.8) "triazine fungicides" (Fungicide Resistance Action Committee (FRAC) code M8) and (45.9) "quinone fungicides" (Fungicide Resistance Action Committee (FRAC) code M9). "Copper fungicides" are inorganic compounds containing copper, typically in the copper(II) oxidation state; examples include copper oxychloride, copper sulfate and copper hydroxide, including compositions such as Bordeaux mixture (tribasic copper sulfate). "Sulfur fungicides" are inorganic chemicals containing rings or chains of sulfur atoms; examples include elemental sulfur. "Dithiocarbamate fungicides" contain a dithiocarbamate molecular moiety; examples include mancozeb, metiram, propineb, ferbam, maneb, thiram, zineb and ziram. "Phthalimide fungicides" contain a phthalimide molecular moiety; examples include folpet, captan and captafol. "Chloronitrile fungicides" contain an aromatic ring substituted with chloro and cyano; examples include chlorothalonil. "Sulfamide fungicides" include dichlofluanid and tolyfluanid. "Guanidine fungicides" include dodine, guazatine, iminoctadine albesilate and iminoctadine triacetate. "Triazine fungicides" include anilazine. "Quinone fungicides" include dithianon.

(46) "Fungicides other than fungicides of classes (1) through (45)" include certain fungicides whose mode of action may be unknown. These include: (46.1) "thiazole carboxamide fungicides" (Fungicide Resistance Action Committee (FRAC) code U5), (46.2) "phenyl-acetamide fungicides" (Fungicide Resistance Action Committee (FRAC) code U6), (46.3) "quinazolinone fungicides" (Fungicide Resistance Action Committee (FRAC) code U7), (46.4) "benzophenone fungicides" (Fungicide Resistance Action Committee (FRAC) code U8) and (46.5) "triazolopyrimidine fungicides". The thiazole carboxamides include ethaboxam. The phenyl-acetamides include cyflufenamid and N-[[(cyclopropylmethoxy)-amino][6-(difluoromethoxy)-2,3-difluorophenyl]-methylene]benzeneacetamide. The quinazolinones include proquinazid. The benzophenones include metrafenone. The triazolopyrimidines include ametoctradin. Class (46) (i.e. "Fungicides other than classes (1) through (45)") also includes bethoxazin, fluxapyroxad, neo-asozin (ferric methanearsonate), pyriofenone, pyrrolnitrin, quinomethionate, tebufloquin, N-[2-[4-[[3-(4-chlorophenyl)-2-propyn-1-yl]oxy]-3-methoxyphenyl]ethyl]-3-methyl-2-[(methylsulfonyl)amino]butanamide, N-[2-[4-[[3-(4-chlorophenyl)-2-propyn-1-yl]oxy]-3-methoxyphenyl]ethyl]-3-methyl-2-[(ethylsulfonyl)amino]butanamide, 2-[[2-fluoro-5-(trifluoromethyl)phenyl]thio]-2-[3-(2-methoxyphenyl)-2-thiazolidinylidene]acetonitrile, 3-[5-(4-chlorophenyl)-2,3-dimethyl-3-isoxazolidinyl]pyridine, 4-fluorophenyl N-[1-[[[1-(4-cyanophenyl)ethyl]sulfonyl]methyl]-propyl]carbamate, 5-chloro-6-(2,4,6-trifluorophenyl)-7-(4-methylpiperidin-1-yl)[1,2,4]-triazolo[1,5-a]pyrimidine, N-(4-chloro-2-nitrophenyl)-N-ethyl-4-methylbenzenesulfonamide, N-[[(cyclopropylmethoxy)amino][6-(difluoromethoxy)-2,3-difluorophenyl]methylene]-benzeneacetamide, N'-[4-[4-chloro-3-(trifluoromethyl)phenoxy]-2,5-dimethylphenyl]-N-ethyl-N-methylmethanimidamide, 1-[(2-propenylthio)carbonyl]-2-(1-methylethyl)-4-(2-methylphenyl)-5-amino-1H-pyrazol- 3-one, N-[9-(dichloromethylene)-1,2,3,4-tetrahydro-1,4-methanonaphthalen-5-yl]-3-(difluoromethyl)-1-methyl-1H-pyrazole-4-carboxamide, 3-(di-fluoromethyl)-N-[9-(difluoromethylene)-1,2,3,4-tetrahydro-1,4-methanonaphthalen-5-yl]-1-methyl-1H-pyrazole-4-carboxamide, N-[9-(dibromomethylene)-1,2,3,4-tetrahydro-1,4-methanonaphthalen-5-yl]-3-(difluoromethyl)-1-methyl-1H-pyrazole-4-carboxamide, N-[9-(dibromomethylene)-1,2,3,4-tetrahydro-1,4-methanonaphthalen-5-yl]-1-methyl-3-(trifluoromethyl)-1H-pyrazole-4-carboxamide, N-[9-(difluoromethylene)-1,2,3,4-tetrahydro-1,4-methanonaphthalen-5-yl]-1-methyl-3-(trifluoromethyl)-1H-pyrazole-4-carboxamide, N-[9-(dichloromethylene)-1,2,3,4-tetrahydro-1,4-methanonaphthalen-5-yl]-1-methyl-3-(trifluoromethyl)-1H-pyrazole-4-carboxamide and N-[4-[[3-[(4-chlorophenyl)methyl]-1,2,4-thiadiazol-5-yl]oxy]-2,5-dimethylphenyl]-N-ethyl-N-methyl-methanimidamide.

Therefore of note is a mixture (i.e. composition) comprising a compound of Formula 1 or Formula 1A and at least one fungicidal compound selected from the group consisting of the aforedescribed classes (1) through (46). Also of note is a composition comprising said mixture (in fungicidally effective amount) and further comprising at least one additional component selected from the group consisting of surfactants, solid diluents and liquid diluents. Of particular note is a mixture (i.e. composition) comprising a compound of Formula 1 or Formula 1A and at least one fungicidal compound selected from the group of specific compounds listed above in connection with classes (1) through (46). Also of particular note is a composition comprising said mixture (in fungicidally effective amount) and further comprising at least one additional surfactant selected from the group consisting of surfactants, solid diluents and liquid diluents.

Examples of other biologically active compounds or agents with which compounds of this invention can be formulated are: insecticides such as abamectin, acephate, acetamiprid, acrinathrin, amidoflumet (S-1955), avermectin, azadirachtin, azinphos-methyl, bifenthrin, bifenazate, buprofezin, carbofuran, cartap, chlorantraniliprole, chlorfenapyr, chlorfluazuron, chlorpyrifos, chlorpyrifos-methyl, chromafenozide, clothianidin, cyantraniliprole (3-bromo-1-(3-chloro-2-pyridinyl)-N-[4-cyano-2-methyl-6-[(methylamino)carbonyl]phenyl]-1H-pyrazole-5-carboxamide), cyflumetofen, cyfluthrin, beta-cyfluthrin, cyhalothrin, lambda-cyhalothrin, cypermethrin, cyromazine, deltamethrin, diafenthiuron, diazinon, dieldrin, diflubenzuron, dimefluthrin, dimethoate, dinotefuran, diofenolan, emamectin, endosulfan, esfenvalerate, ethiprole, fenothiocarb, fenoxycarb, fenpropathrin, fenvalerate, fipronil, flonicamid, flubendiamide, flucythrinate, tau-fluvalinate, flufenerim (UR-50701), flufenoxuron, fonophos, halofenozide, hexaflumuron, hydramethylnon, imidacloprid, indoxacarb, isofenphos, lufenuron, malathion, meperfluthrin, metaflumizone, metaldehyde, methamidophos, methidathion, methomyl, methoprene, methoxychlor, methoxyfenozide, metofluthrin, milbemycin oxime, monocrotophos, nicotine, nitenpyram, nithiazine, novaluron, noviflumuron (XDE-007), oxamyl, parathion, parathion-methyl, permethrin, phorate, phosalone, phosmet, phosphamidon, pirimicarb, profenofos, profluthrin, pymetrozine, pyrafluprole, pyrethrin, pyridalyl, pyrifluquinazon, pyriprole, pyriproxyfen, rotenone, ryanodine, spinetoram, spinosad, spirodiclofen, spiromesifen (BSN 2060), spirotetramat, sulfoxaflor, sulprofos, tebufenozide, teflubenzuron, tefluthrin, terbufos, tetrachlorvinphos, tetramethylfluthrin, thiacloprid, thiamethoxam, thiodicarb, thiosultap-sodium, tolfenpyrad, tralomethrin, triazamate, trichlorfon and triflumuron; and biological agents including entomopathogenic bacteria, such as *Bacillus thuringiensis* subsp. *aizawai*, *Bacillus thuringiensis* subsp. *kurstaki*, and the encapsulated delta-endotoxins of *Bacillus thuringiensis* (e.g., Cellcap, MPV, MPVII); entomopathogenic fungi, such as green muscardine fungus; and entomopathogenic virus including baculovirus, nucleopolyhedro virus (NPV) such as HzNPV, AfNPV; and granulosis virus (GV) such as CpGV.

Compounds of this invention and compositions thereof can be applied to plants genetically transformed to express proteins toxic to invertebrate pests (such as *Bacillus thuringiensis* delta-endotoxins). The effect of the exogenously applied fungicidal compounds of this invention may be synergistic with the expressed toxin proteins.

General references for agricultural protectants (i.e. insecticides, fungicides, nematocides, acaricides, herbicides and biological agents) include *The Pesticide Manual*, 13th Edition, C. D. S. Tomlin, Ed., British Crop Protection Council, Farnham, Surrey, U.K., 2003 and *The BioPesticide Manual*, 2nd Edition, L. G. Copping, Ed., British Crop Protection Council, Farnham, Surrey, U.K., 2001.

For embodiments where one or more of these various mixing partners are used, the weight ratio of these various mixing partners (in total) to the compound of Formula 1 or Formula 1A is typically between about 1:3000 and about 3000:1. Of note are weight ratios between about 1:300 and about 300:1 (for example ratios between about 1:30 and about 30:1). One skilled in the art can easily determine through simple experimentation the biologically effective amounts of active ingredients necessary for the desired spectrum of biological activity. It will be evident that including these additional components may expand the spectrum of diseases controlled beyond the spectrum controlled by the compound of Formula 1 or Formula 1A alone.

In certain instances, combinations of a compound of this invention with other biologically active (particularly fungicidal) compounds or agents (i.e. active ingredients) can result in a greater-than-additive (i.e. synergistic) effect. Reducing the quantity of active ingredients released in the environment while ensuring effective pest control is always desirable. When synergism of fungicidal active ingredients occurs at application rates giving agronomically satisfactory levels of fungal control, such combinations can be advantageous for reducing crop production cost and decreasing environmental load.

Of note is a combination of a compound of Formula 1 or Formula 1A with at least one other fungicidal active ingredient. Of particular note is such a combination where the other fungicidal active ingredient has different site of action from the compound of Formula 1 or Formula 1A. In certain instances, a combination with at least one other fungicidal active ingredient having a similar spectrum of control but a different site of action will be particularly advantageous for resistance management. Thus, a composition of the present invention can further comprise a biologically effective amount of at least one additional fungicidal active ingredient having a similar spectrum of control but a different site of action.

Of particular note are compositions which in addition to compound of Formula 1 or Formula 1A include at least one compound selected from the group consisting of (1) alkylenebis(dithiocarbamate) fungicides; (2) cymoxanil; (3) phenylamide fungicides; (4) proquinazid (6-iodo-3-propyl-2-propyloxy-4(3H)-quinazolinone); (5) chlorothalonil; (6) carboxamides acting at complex II of the fungal mitochondrial respiratory electron transfer site; (7) quinoxyfen; (8) metrafenone; (9) cyflufenamid; (10) cyprodinil; (11) copper compounds; (12) phthalimide fungicides; (13) fosetyl-aluminum; (14) benzimidazole fungicides; (15) cyazofamid; (16) fluazinam; (17) iprovalicarb; (18) propamocarb; (19) validomycin; (20) dichlorophenyl dicarboximide fungicides; (21) zoxamide; (22) fluopicolide; (23) mandipropamid; (24) carboxylic acid amides acting on phospholipid biosynthesis and cell wall deposition; (25) dimethomorph; (26) non-DMI sterol biosynthesis inhibitors; (27) inhibitors of demethylase in sterol biosynthesis; (28) $bc_1$ complex fungicides; and salts of compounds of (1) through (28).

Further descriptions of classes of fungicidal compounds are provided below.

Sterol biosynthesis inhibitors (group (27)) control fungi by inhibiting enzymes in the sterol biosynthesis pathway. Demethylase-inhibiting fungicides have a common site of action within the fungal sterol biosynthesis pathway, involving inhibition of demethylation at position 14 of lanosterol or 24-methylene dihydrolanosterol, which are precursors to sterols in fungi. Compounds acting at this site are often referred to as demethylase inhibitors, DMI fungicides, or DMIs. The demethylase enzyme is sometimes referred to by other names in the biochemical literature, including cytochrome P-450 (14DM). The demethylase enzyme is described in, for example, *J. Biol. Chem.* 1992, 267, 13175-79 and references cited therein. DMI fungicides are divided between several chemical classes: azoles (including triazoles and imidazoles), pyrimidines, piperazines and pyridines. The triazoles include azaconazole, bromuconazole, cyproconazole, difenoconazole, diniconazole (including diniconazole-M), epoxiconazole, etaconazole, fenbuconazole, fluquinconazole, flusilazole, flutriafol, hexaconazole, imibenconazole, ipconazole, metconazole, myclobutanil, penconazole, propiconazole, prothioconazole, quinconazole, simeconazole, tebuconazole, tetraconazole, triadimefon, triadimenol, triticonazole and uniconazole. The imidazoles include clotrimazole, econazole, imazalil, isoconazole, miconazole, oxpoconazole, prochloraz and triflumizole. The pyrimidines include fenarimol, nuarimol and triarimol. The piperazines include triforine. The pyridines include buthiobate and pyrifenox. Biochemical investigations have shown that all of the above mentioned fungicides are DMI fungicides as described by K. H. Kuck et al. in *Modern Selective Fungicides—Properties, Applications and Mechanisms of Action*, H. Lyr (Ed.), Gustav Fischer Verlag: New York, 1995, 205-258.

$bc_1$ Complex Fungicides (group 28) have a fungicidal mode of action which inhibits the $bc_1$ complex in the mitochondrial respiration chain. The $bc_1$ complex is sometimes referred to by other names in the biochemical literature, including complex III of the electron transfer chain, and ubihydroquinone:cytochrome c oxidoreductase. This complex is uniquely identified by Enzyme Commission number EC1.10.2.2. The $bc_1$ complex is described in, for example, *J. Biol. Chem.* 1989, 264, 14543-48; *Methods Enzymol.* 1986, 126, 253-71; and references cited therein. Strobilurin fungicides such as azoxystrobin, dimoxystrobin, enestroburin (SYP-Z071), fluoxastrobin, kresoxim-methyl, metominostrobin, orysastrobin, picoxystrobin, pyraclostrobin, pyrametostrobin, pyraoxystrobin and trifloxystrobin are known to have this mode of action (H. Sauter et al., *Angew. Chem. Int. Ed.* 1999, 38, 1328-1349). Other fungicidal compounds that inhibit the $bc_1$ complex in the mitochondrial respiration chain include famoxadone and fenamidone.

Alkylenebis(dithiocarbamate)s (group (1)) include compounds such as mancozeb, maneb, propineb and zineb. Phenylamides (group (3)) include compounds such as metalaxyl, benalaxyl, furalaxyl and oxadixyl. Carboxamides (group (6)) include compounds such as boscalid, carboxin, fenfuram, flutolanil, furametpyr, mepronil, oxycarboxin, thifluzamide, penthiopyrad and N-[2-(1,3-dimethylbutyl)phenyl]-5-fluoro-1,3-dimethyl-1H-pyrazole-4-carboxamide (PCT Patent Publication WO 2003/010149), and are known to inhibit mitochondrial function by disrupting complex II (succinate dehydrogenase) in the respiratory electron transport chain. Copper compounds (group (11)) include compounds such as copper oxychloride, copper sulfate and copper hydroxide, including compositions such as Bordeaux mixture (tribasic copper sulfate). Phthalimides (group (12)) include compounds such as folpet and captan. Benzimidazole fungicides (group (14)) include benomyl and carbendazim. Dichlorophenyl dicarboximide fungicides (group (20)) include chlozolinate, dichlozoline, iprodione, isovaledione, myclozolin, procymidone and vinclozolin.

Non-DMI sterol biosynthesis inhibitors (group (26)) include morpholine and piperidine fungicides. The morpholines and piperidines are sterol biosynthesis inhibitors that have been shown to inhibit steps in the sterol biosynthesis pathway at a point later than the inhibitions achieved by the DMI sterol biosynthesis (group (27)). The morpholines include aldimorph, dodemorph, fenpropimorph, tridemorph and trimorphamide. The piperidines include fenpropidin.

Of further note are combinations of compounds of Formula 1 or Formula 1A with azoxystrobin, kresoxim-methyl, trifloxystrobin, pyraclostrobin, picoxystrobin, dimoxystrobin, metominostrobin/fenominostrobin, carbendazim, chlorothalonil, quinoxyfen, metrafenone, cyflufenamid, fenpropidine, fenpropimorph, bromuconazole, cyproconazole, difenoconazole, epoxiconazole, fenbuconazole, flusilazole, hexaconazole, ipconazole, metconazole, penconazole, propiconazole, proquinazid, prothioconazole, tebuconazole, triticonazole, famoxadone, prochloraz, penthiopyrad and boscalid (nicobifen).

Specifically preferred mixtures (compound numbers refer to compounds in Index Tables A-C below) are selected from the group: combinations of Compound 3, Compound 10, Compound 12, Compound 14, Compound 17, Compound 18, Compound 19, Compound 21, Compound 30, Compound 31, Compound 33, Compound 36, Compound 37, Compound 40, Compound 42, Compound 45, Compound 61, Compound 69, Compound 80, Compound 82, Compound 85, Compound 90, Compound 97, Compound 112, Compound 119, Compound 120, Compound 126, Compound 137, Compound 142, Compound 157, Compound 160, or Compound 179 with azoxystrobin, combinations of Compound 3, Compound 10, Compound 12, Compound 14, Compound 17, Compound 18, Compound 19, Compound 21, Compound 30, Compound 31, Compound 33, Compound 36, Compound 37, Compound 40, Compound 42, Compound 45, Compound 61, Compound 69, Compound 80, Compound 82, Compound 85, Compound 90, Compound 97, Compound 112, Compound 119, Compound 120, Compound 126, Compound 137, Compound 142, Compound 157, Compound 160, or Compound 179 with kresoxim-methyl, combinations of Compound 3, Compound 10, Compound 12, Compound 14, Compound 17, Compound 18, Compound 19, Compound 21, Compound 30, Compound 31, Compound 33, Compound 36, Compound 37, Compound 40, Compound 42, Compound 45, Compound 61, Compound 69, Compound 80, Compound 82, Compound 85, Compound 90, Compound 97, Compound 112, Compound 119, Compound 120, Compound 126, Compound 137, Compound 142, Compound 157, Compound 160, or Compound 179 with trifloxystrobin, combinations of Compound 3, Compound 10, Compound 12, Compound 14, Compound 17, Compound 18, Compound 19, Compound 21, Compound 30, Compound 31, Compound 33, Compound 36, Compound 37, Compound 40, Compound 42, Compound 45, Compound 61, Compound 69, Compound 80, Compound 82, Compound 85, Compound 90, Compound 97, Compound 112, Compound 119, Compound 120, Compound 126, Compound 137, Compound 142, Compound 157, Compound 160, or Compound 179 with picoxystrobin, combinations of Compound 3, Compound 10, Compound 12, Compound 14, Compound 17, Compound 18, Compound 19, Compound 21, Compound 30, Compound 31, Compound 33, Compound 36, Compound 37, Compound 40, Compound 42, Compound 45, Compound 61, Compound 69, Compound 80, Compound 82, Compound 85, Compound 90, Compound 97, Compound 112, Compound 119, Compound 120, Compound 126, Compound 137, Compound 142, Compound 157, Compound 160, or Compound 179 with metominostrobin/fenominostrobin, combinations of Compound 3, Compound 10, Compound 12, Compound 14, Compound 17, Compound 18, Compound 19, Compound 21, Compound 30, Compound 31, Compound 33, Compound 36, Compound 37, Compound 40, Compound 42, Compound 45, Compound 61, Compound 69, Compound 80, Compound 82, Compound 85, Compound 90, Compound 97, Compound 112, Compound 119, Compound 120, Compound 126, Compound 137, Compound 142, Compound 157, Compound 160, or Compound 179 with quinoxyfen, combinations of Compound 3, Compound 10, Compound 12, Compound 14, Compound 17, Compound 18, Compound 19, Compound 21, Compound 30, Compound 31, Compound 33, Compound 36, Compound 37, Compound 40, Compound 42, Compound 45, Compound 61, Compound 69, Compound 80, Compound 82, Compound 85, Compound 90, Compound 97, Compound 112, Compound 119, Compound 120, Compound 126, Compound 137, Compound 142, Compound 157, Compound 160, or Compound 179 with metrafenone, combinations of Compound 3, Compound 10, Compound 12, Compound 14, Compound 17, Compound 18, Compound 19, Compound 21, Compound 30, Compound 31, Compound 33, Compound 36, Compound 37, Compound 40, Compound 42, Compound 45, Compound 61, Compound 69, Compound 80, Compound 82, Compound 85, Compound 90, Compound 97, Compound 112, Compound 119, Compound 120, Compound 126, Compound 137, Compound 142, Compound 157, Compound 160, or Compound 179 with fenpropidine, combinations of Compound 3, Compound 10, Compound 12, Compound 14, Compound 17, Compound 18, Compound 19, Compound 21, Compound 30, Compound 31, Compound 33, Compound 36, Compound 37, Compound 40, Compound 42, Compound 45, Compound 61, Compound 69, Compound 80, Compound 82, Compound 85, Compound 90, Compound 97, Compound 112, Compound 119, Compound 120, Compound 126, Compound 137, Compound 142, Compound 157, Compound 160, or Compound 179 with fenpropimorph, combinations of Compound 3, Compound 10, Compound 12, Compound 14, Compound 17, Compound 18, Compound 19, Compound 21, Compound 30, Compound 31, Compound 33, Compound 36, Compound 37, Compound 40, Compound 42, Compound 45, Compound 61, Compound 69, Compound 80, Compound 82, Compound 85, Compound 90, Compound 97, Compound 112, Compound 119, Compound 120, Compound 126, Compound 137, Compound 142, Compound 157, Compound 160, or Compound 179 with cyproconazole, combinations of Compound 3, Compound 10, Compound 12, Compound 14, Compound 17, Compound 18, Compound 19, Compound 21, Compound 30, Compound 31, Compound 33, Compound 36, Compound 37, Compound 40, Compound 42, Compound 45, Compound 61, Compound 69, Compound 80, Compound 82, Compound 85, Compound 90, Compound 97, Compound 112, Compound 119, Compound 120, Compound 126, Compound 137, Compound 142, Compound 157, Compound 160, or Compound 179 with epoxiconazole, combinations of Compound 3, Compound 10, Compound 12, Compound 14, Compound 17, Compound 18, Compound 19, Compound 21, Compound 30, Compound 31, Compound 33, Compound 36, Compound 37, Compound 40, Compound 42, Compound 45, Compound 61, Compound 69, Compound 80, Compound 82, Compound 85, Compound 90, Compound 97, Compound 112, Compound 119, Compound 120, Compound 126, Compound 137, Compound 142, Compound 157, Compound 160, or Compound 179 with flusilazole, combinations of Compound 3, Compound 10, Compound 12, Compound 14, Compound 17, Compound 18, Compound 19, Compound 21, Compound 30, Compound 31, Compound 33, Compound 36, Compound 37, Compound 40, Compound 42, Compound 45, Compound 61, Compound 69, Compound 80, Compound 82, Compound 85, Compound 90, Compound 97, Compound 112, Compound 119, Compound 120, Compound 126, Compound 137, Compound 142, Compound 157, Compound 160, or Compound 179 with metconazole, combinations of Compound 3, Compound 10, Compound 12, Compound 14, Compound 17, Compound 18, Compound 19, Compound 21, Compound 30, Compound 31, Compound 33, Compound 36, Compound 37, Compound 40, Compound 42, Compound 45, Compound 61, Compound 69, Compound 80, Compound 82, Compound 85, Compound 90, Compound 97, Compound 112, Compound 119, Compound 120, Compound 126, Compound 137, Compound 142, Compound 157, Compound 160, or Compound 179 with propiconazole, combinations of Compound 3, Compound 10, Compound 12, Compound 14, Compound 17, Compound 18, Compound 19, Compound 21, Compound 30, Compound 31, Compound 33, Compound 36, Compound 37, Compound 40, Compound 42, Compound 45, Compound 61, Compound 69, Compound 80, Compound 82, Compound 85, Compound 90, Compound 97, Compound 112, Compound 119, Compound 120, Compound 126, Compound 137, Compound 142, Compound 157, Compound 160, or Compound 179 with proquinazid, combinations of Compound 3, Compound 10, Compound 12, Compound 14, Compound 17, Compound 18, Compound 19, Compound 21, Compound 30, Compound 31, Compound 33, Compound 36, Compound 37, Compound 40, Compound 42, Compound 45, Compound 61, Compound 69, Compound 80, Compound 82, Compound 85, Compound 90, Compound 97, Compound 112, Compound 119, Compound 120, Compound 126, Compound 137, Compound 142, Compound 157, Compound 160, or Compound 179 with prothioconazole, combinations of Compound 3, Compound 10, Compound 12, Compound 14, Compound 17, Compound 18, Compound 19, Compound 21, Compound 30, Compound 31, Compound 33, Compound 36, Compound 37, Compound 40, Compound 42, Compound 45, Compound 61, Compound 69, Compound 80, Compound 82, Compound 85, Compound 90, Compound 97, Compound 112, Compound 119, Compound 120, Compound 126, Compound 137, Compound 142, Compound 157, Compound 160, or Compound 179 with tebuconazole, combinations of Compound 3, Compound 10, Compound 12, Compound 14, Compound 17, Compound 18, Compound 19, Compound 21, Compound 30, Compound 31, Compound 33, Compound 36, Compound 37, Compound 40, Compound 42, Compound 45, Compound 61, Compound 69, Compound 80, Compound 82, Compound 85, Compound 90, Compound 97, Compound 112, Compound 119, Compound 120, Compound 126, Compound 137, Compound 142, Compound 157, Compound 160, or Compound 179 with triticonazole, combinations of Compound 3, Compound 10, Compound 12, Compound 14, Compound 17, Compound 18, Compound 19, Compound 21, Compound 30, Compound 31, Compound 33, Compound 36, Compound 37, Compound 40, Compound 42, Compound 45, Compound 61, Compound 69, Compound 80, Compound 82, Compound 85, Compound 90, Compound 97, Compound 112, Compound 119, Compound 120, Compound 126, Compound 137, Compound 142, Compound 157, Compound 160, or Compound 179 with famoxadone, combinations of Compound 3, Compound 10, Compound 12, Compound 14, Compound 17, Compound 18, Compound 19, Compound 21, Compound 30, Compound 31, Compound 33, Compound 36, Compound 37, Compound 40, Compound 42, Compound 45, Compound 61, Compound 69, Compound 80, Compound 82, Compound 85, Compound 90, Compound 97, Compound 112, Compound 119, Compound 120, Compound 126, Compound 137, Compound 142, Compound 157, Compound 160, or Compound 179 with penthiopyrad, combinations of Compound 3, Compound 10, Compound 12, Compound 14, Compound 17, Compound 18, Compound 19, Compound 21, Compound 30, Compound 31, Compound 33, Compound 36, Compound 37, Compound 40, Compound 42, Compound 45, Compound 61, Compound 69, Compound 80, Compound 82, Compound 85, Compound 90, Compound 97, Compound 112, Compound 119, Compound 120, Compound 126, Compound 137, Compound 142, Compound 157, Compound 160, or Compound 179 with 3-(difluoromethyl)-1-methyl-N-(3',4',5'-trifluoro [1,1'-biphenyl]-2-yl)-1H-pyrazole-4-carboxamide, combinations of Compound 3, Compound 10, Compound 12, Compound 14, Compound 17, Compound 18, Compound 19, Compound 21, Compound 30, Compound 31, Compound 33, Compound 36, Compound 37, Compound 40, Compound 42, Compound 45, Compound 61, Compound 69, Compound 80, Compound 82, Compound 85, Compound 90, Compound 97, Compound 112, Compound 119, Compound 120, Compound 126, Compound 137, Compound 142, Compound 157, Compound 160, or Compound 179 with 5-ethyl-6-octyl-[1,2,4]triazole[1,5-a]pyrimidin-7-amine, and combinations of Compound 3, Compound 10, Compound 12, Compound 14, Compound 17, Compound 18, Compound 19, Compound 21, Compound 30, Compound 31, Compound 33, Compound 36, Compound 37, Compound 40, Compound 42, Compound 45, Compound 61, Compound 69, Compound 80, Compound 82, Compound 85, Compound 90, Compound 97, Compound 112, Compound 119, Compound 120, Compound 126, Compound 137, Compound 142, Compound 157, Compound 160, or Compound 179 with Initium®.

The control efficacy of compounds of this invention on specific pathogens is demonstrated below in TABLE A. The pathogen control protection afforded by the compounds is not limited, however, to these species (i.e. species described in Tests A-F below). Descriptions of the compounds are provided in Index Tables A-C below. The following abbreviations are used in the index tables: Me is methyl, MeO is methoxy, EtO is ethoxy, CN is cyano, $NO_2$ is nitro and Ph is phenyl. The abbreviation "Cmpd. No." means compound number, and "Ex." stands for "Example" and is followed by a number indicating in which example the compound is prepared. Mass spectra (MS) are reported as the molecular weight of the highest isotopic abundance parent ion (M+1) formed by addition of $H^+$ (molecular weight of 1) to the molecule, observed by mass spectrometry using atmospheric pressure chemical ionization ($AP^+$).

INDEX TABLE A

| Cmpd. No. | $R^2$ | $Q^1$ | $Q^2$ | m.p. (° C.) | AP+ (M + 1) |
|---|---|---|---|---|---|
| 3 | Me | 2-Cl, 4-F—Ph | 2-Cl, 6-F—Ph | | 383 |
| 9 | Cl | 2,4-di-F—Ph | 2-Cl, 4-F—Ph | 104-107 | |
| 10 | Me | 2-Cl, 4-F—Ph | 2,6-di-F—Ph | 142-144 | |
| 14 (Ex. 4) | Me | 2,4-di-F—Ph | 2,6-di-F—Ph | ** | ** |
| 15 | Me | 2,4,6-tri-F—Ph | 2,6-di-F—Ph | | 369 |
| 16 | Me | 2,6-di-F, 4-MeO—Ph | 2,6-di-F—Ph | | 381 |
| 17 | Me | 2,4-di-F—Ph | 2-Cl, 4-F—Ph | | 367 |
| 18 | Me | 2-Cl, 4-F—Ph | 2-Cl, 4-F—Ph | | 383 |
| 19 | Me | 2,4,6-tri-F—Ph | 2-Cl, 4-F—Ph | | 385 |
| 20 | Me | 2,6-di-F, 4-MeO—Ph | 2-Cl, 4-F—Ph | | 397 |
| 21 | Me | 2-Br, 4-F—Ph | 2,6-di-F—Ph | | 411 |
| 22 | Me | 2-F, 4-CN—Ph | 2,6-diF—Ph | * | * |
| 23 | Me | 2-Br, 4-F—Ph | 2-Cl, 4-F—Ph | | 429 |
| 25 | Me | 2-F, 4-CN—Ph | 2-Cl, 4-F—Ph | | 374 |
| 30 (Ex. 9) | Br | 2,4-di-F—Ph | 2-Cl, 4-F—Ph | ** | ** |
| 33 | Me | 2,4-di-F—Ph | 2-Cl, 6-F—Ph | | 367 |
| 34 | Me | 2,4,6-tri-F—Ph | 2-Cl, 6-F—Ph | | 385 |
| 37 | Me | 2-Br, 4-F—Ph | 2-Cl, 6-F—Ph | | 427 |
| 38 | Me | 4-CN, 2-F—Ph | 2-Cl, 6-F—Ph | | 374 |
| 39 | Me | 2,6-di-F, 4-MeO—Ph | 2-Cl, 6-F—Ph | | 397 |
| 53 (Ex. 11) | CN | 2-Cl, 4-F—Ph | 2,6-di-F—Ph | ** | ** |
| 55 | Me | 2,4,6-tri-Cl—Ph | 2-Cl, 6-F—Ph | | 435 |
| 61 | Me | 2-Cl, 4-F—Ph | 2,4,6-tri-F—Ph | | 385 |
| 66 | Me | 2,4-di-F—Ph | 2,4,6-tri-F—Ph | | 369 |
| 69 | Me | 2-Cl, 4-F—Ph | 2,6-di-Cl—Ph | 160-162 | |
| 70 | Me | 2,4,6-tri-F—Ph | 2,6-di-Cl—Ph | 137-139 | |
| 71 | Me | 2-Cl, 4-F—Ph | 2,4-di-F—Ph | * | * |
| 72 (Ex. 8) | Me | 2,4-di-F—Ph | 2,4-di-F—Ph | ** | ** |
| 74 | Me | 2,4-di-F—Ph | 2,6-di-Cl—Ph | 125-128 | |

INDEX TABLE A-continued

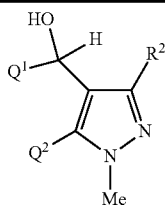

| Cmpd. No. | R² | Q¹ | Q² | m.p. (° C.) | AP+ (M + 1) |
|---|---|---|---|---|---|
| 76 | Me | 2,4-di-F—Ph | 2-Br, 4-F—Ph | | 411 |
| 77 | Me | 4-Cl—Ph | 2,6-di-Cl—Ph | | 383 |
| 79 Note 1 | Me | 2-Cl, 4-F—Ph | 2-Br | | 411 |
| 80 Note 2 | Me | 2-Cl, 4-F—Ph | 2-Br | | 411 |
| 82 | Me | 2,4,6-tri-F—Ph | 2-Br, 4-F—Ph | * | * |
| 85 | Me | 2,6-di-Cl—Ph | 2-Cl, 6-F—Ph | | 399 |
| 86 Note 3 | Me | 2-Cl, 4-F—Ph | 2,6-di-F—Ph | 61-71 | |
| 87 Note 4 | Me | 2-Cl, 4-F—Ph | 2,6-di-F—Ph | | 367 |
| 88 | Me | 2-Br, 4-F—Ph | 2-I | | 503 |
| 90 | Me | 2,4-di-Cl—Ph | 2-Cl, 6-F—Ph | | 401 |
| 94 | Me | 2-Cl, 4-F—Ph | 2-Br, 6-F—Ph | | 429 |
| 95 | Me | 2-Cl, 4-F—Ph | 2-Br, 4-F—Ph | * | * |
| 97 | Me | 2,4-di-F—Ph | 2,4-di-Cl—Ph | 123-127 | |
| 98 | Me | 2-Cl, 4-F—Ph | 3,5-di-Cl-4-pyridinyl | | 400 |
| 99 | Me | 2-I, 4-F—Ph | 2-Cl, 4-F—Ph | | 475 |
| 100 | Me | 2-Cl, 4-F—Ph | 2,4-di-Cl—Ph | | 401 |
| 101 | Me | 4-Cl, 2-F—Ph | 2,4-di-Cl—Ph | 150-152 | |
| 103 Note 3 | Me | 2-Cl, 4-F—Ph | 4-F, 2-I—Ph | 148-151 | |
| 104 Note 4 | Me | 2-Cl, 4-F—Ph | 4-F, 2-I—Ph | | 475 |
| 105 | Me | 2-Cl, 4-F—Ph | 4-F—Ph | | 349 |
| 106 | Me | 2,4-di-F—Ph | 4-Br-2,6-di-4-F—Ph | | 431 |
| 112 | Me | 2,4-di-F—Ph | 4-CN-2,6-di-4-F—Ph | 170-173 | |
| 113 | Br | 2-Br, 4-F—Ph | 2,6-di-4-F—Ph | 118-120 | |
| 114 | Br | 2,4,6-tri-F—Ph | 2,6-di-4-F—Ph | 168-170 | |
| 117 | Cl | 2,4-di-F—Ph | 2,6-di-4-F—Ph | 97-99 | |
| 118 | MeO | 2-Cl, 4-F—Ph | 2-Cl, 4-F—Ph | | 399 |
| 119 | Br | 2-Cl, 4-F—Ph | 2,6-di-4-F—Ph | 83-86 | |
| 120 | MeO | 2-Cl, 4-F—Ph | 2-Cl, 6-F—Ph | | 399 |
| 124 | Br | 2,4-di-F—Ph | 2,6-di-F—Ph | 80-82 | |
| 125 | Br | 2-Cl, 4-F—Ph | 2-Cl, 4-F—Ph | 142-144 | |
| 126 | MeO | 2-Cl, 4-F—Ph | 2,6-di-F—Ph | | 383 |
| 127 | EtO | 2-Cl, 4-F—Ph | 2,6-di-F—Ph | | 397 |
| 128 | F₂CHO | 2-Cl, 4-F—Ph | 2,6-di-F—Ph | | 419 |
| 129 | Me | 2-Me, 4-F—Ph | 2,6-di-F—Ph | | 347 |
| 130 | H | 2-Cl, 4-F—Ph | 2,6-di-F—Ph | 136-138 | |
| 131 | Br | 2,4-di-F—Ph | 2-Cl, 6-F—Ph | 143-146 | |
| 132 | Br | 2-Br, 4-F—Ph | 2-Cl, 6-F—Ph | 122-125 | |
| 133 | Cl | 2,4-di-F—Ph | 2-Cl, 6-F—Ph | 157-160 | |
| 134 | Cl | 2-Br, 4-F—Ph | 2-Cl, 6-F—Ph | 117-120 | |
| 135 | Cl | 2-Cl, 4-F—Ph | 2-Cl, 6-F—Ph | 131-134 | |
| 136 | Cl | 2-Br, 4-F—Ph | 2,6-di-F—Ph | 100-102 | |
| 137 | Cl | 2-Cl, 4-F—Ph | 2,6-di-F—Ph | 113-115 | |
| 138 | MeO | 2,3,6-tri-F—Ph | 2,6-di-F—Ph | | 385 |
| 139 | MeO | 2-Cl, 3,6-di-F—Ph | 2,6-di-F—Ph | | 400 |
| 140 | MeO | 2-Me, 4-F—Ph | 2-Cl, 6-F—Ph | | 379 |
| 141 | MeO | 2-Cl, 4-F—Ph | 2-Cl, 4,6-di-F—Ph | | 417 |
| 142 | MeO | 2-Cl, 4-MeO—Ph | 2-Cl, 6-F—Ph | | 411 |
| 143 | MeO | 2-F, 4-MeO—Ph | 2-Cl, 6-F—Ph | | 395 |
| 144 | MeO | 2-Cl, 3,6-di-F—Ph | 2-Cl, 6-F—Ph | | 417 |
| 145 | MeO | 2,3,6-tri-F—Ph | 2-Cl, 6-F—Ph | | 401 |
| 146 | Me | 2,4-di-F—Ph | 2-Me-1H-imidazol-1-yl | 180-183 | |
| 147 | Me | 2-Me, 4-F—Ph | 2-Me-1H-imidazol-1-yl | | 315 |
| 148 | Br | 2-Cl, 4-F—Ph | 2-Cl, 6-F—Ph | 131-134 | |
| 149 | Br | 2-Me, 4-F—Ph | 2-Cl, 6-F—Ph | 133-136 | |
| 150 | Me | 2-Me, 4-F—Ph | 2-Cl-1H-imidazol-1-yl | 165-168 | |
| 151 | Me | 2,4-di-F—Ph | 2-Cl-1H-imidazol-1-yl | 183-186 | |
| 152 | MeO | 2-Cl, 4-F—Ph | 2,4,6-F—Ph | | 401 |
| 153 | MeO | 2,4-di-F—Ph | 2,4,6-tri-F—Ph | | 385 |
| 154 | MeO | 2-F—Ph | 2,4,6-tri-F—Ph | | 365 |
| 155 | MeO | 2-Cl, 6-F—Ph | 2,4,6-tri-F—Ph | | 401 |
| 156 | MeO | 2,4-di-F—Ph | 2,6-di-F—Ph | | 367 |
| 157 (Ex. 12) | MeO | 2-Me, 4-F—Ph | 2,6-di-F—Ph | ** | ** |
| 158 | Me | 2-Me 4-F—Ph | 3,5-di-Me-1H-pyrazol-1-yl | 97-99 | |
| 159 | Me | 2,4-di-F—Ph | 3,5-di-Me-1H-pyrazol-1-yl | 136-138 | |
| 160 | MeO | 2-Cl, 4-MeO—Ph | 2,6-di-F—Ph | | 365 |
| 161 | MeO | 2-F, 4-MeO—Ph | 2,6-di-F—Ph | | 379 |
| 162 | MeO | 2-Cl, 4-F—Ph | 4-Cl, 2,6-di-F—Ph | | 417 |

INDEX TABLE A-continued

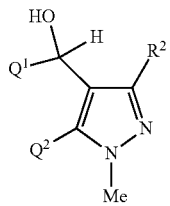

| Cmpd. No. | R² | Q¹ | Q² | m.p. (° C.) | AP+ (M + 1) |
|---|---|---|---|---|---|
| 163 | Br | 2,4-di-Cl—Ph | 2,6-di-F—Ph | 174-176 | |
| 164 | Br | 2-Br, 4-F—Ph | 2-Cl, 4-F—Ph | 148-150 | |
| 165 | Br | 2-Me, 4-F—Ph | 2,6-di-F—Ph | 85-87 | |
| 166 | Me | 2-Cl, 4-F—Ph | 3,5-di-F-4-pyridinyl | * | * |
| 167 | Me | 2,4-di-F—Ph | 3,5-di-Cl-4-pyridinyl | * | * |
| 168 | Me | 2,4-di-F—Ph | 3,5-di-F-4-pyridinyl | | 352 |
| 169 | Me | 2-Cl, 4-MeO—Ph | 2-Cl, 4-F—Ph | | 395 |
| 170 | Me | 2-Cl, 4-MeO—Ph | 2-Cl, 6-F—Ph | | 395 |
| 171 | Me | 2-Cl, 4-F—Ph | 2,6-di-F, 4-MeO—Ph | | 397 |
| 172 | Me | 2,4-di-F—Ph | 2,6-di-F, 4-MeO—Ph | | 381 |
| 173 | Me | 2,4,6-tri-F—Ph | 2,6-di-F, 4-MeO—Ph | | 399 |

*See Index Table D for ¹H NMR data.
**See synthesis example for ¹H NMR.
Note 1: 99% enantiomer A.
Note 2: 13% enantiomer A, 87% enantiomer B.
Note 3: enantiomer A.
Note 4: enantiomer B.

INDEX TABLE B

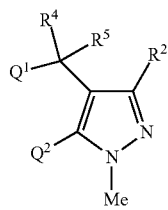

| Cmpd. No. | R¹ | Q¹ | Q² | R⁴ | R⁵ | AP+ (M + 1) |
|---|---|---|---|---|---|---|
| 29 | Me | 2,4-di-F—Ph | 2-Cl, 6-F—Ph | OH | Me | 381 |
| 54 | Me | 2-Cl, 4-F—Ph | 2,6-di-F—Ph | F | H | 369 |
| 67 | Me | 2-Cl, 4-F—Ph | 2-Cl, 6-F—Ph | MeO | H | 397 |
| 68 (Ex. 5) | Me | 2,4-di-F—Ph | 2,6-di-F—Ph | F | H | ** |
| 75 | Me | 2,4,6-tri-F—Ph | 2-Cl, 6-F—Ph | F | H | 387 |
| 84 | Me | 2-Cl, 4-F—Ph | 2,6-di-F—Ph | Cl | H | 383 |
| 92 | Me | 2,4-di-Cl—Ph | 2,6-di-F—Ph | F | H | 384 |
| 107 | Me | 2-Cl, 4-F—Ph | 2,6-di-4-F—Ph | N≡CCH₂O | H | 406 |
| 108 | Me | 2-Cl, 4-F—Ph | 2,6-di-4-F—Ph | CH₃C(=O)O | H | 409 |
| 109 | Me | 2-Cl, 4-F—Ph | 2,6-di-4-F—Ph | CH₂=CHCH₂O | H | 407 |
| 110 | Me | 2-Cl, 4-F—Ph | 2,6-di-4-F—Ph | CH₃OCH₂O | H | 411 |
| 111 | Me | 2-Cl, 4-F | 2,6-di-4-F—Ph | N≡CS | H | 408 |
| 115 | Me | 2,4-di-F—Ph | 2,6-di-4-F—Ph | N≡CS | H | 392 |
| 116 | Me | 2,4,6-tri-F—Ph | 2,6-di-4-F—Ph | N≡CS | H | 410 |
| 121 | Me | 2-Cl, 4-F—Ph | 2-Cl, 6-F—Ph | N≡CS | H | 424 |
| 122 | Me | 2,4-di-F—Ph | 2-Cl, 6-F—Ph | N≡CS | H | 408 |
| 123 | Me | 2,4,6-tri-F—Ph | 2-Cl, 6-F—Ph | N≡CS | H | 426 |

**See synthesis example for ¹H NMR.

INDEX TABLE C

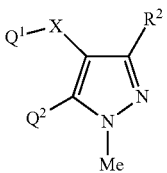

| Cmpd. No. | R² | Q¹ | Q² | X | m.p. (° C.) | AP+ (M + 1) |
|---|---|---|---|---|---|---|
| 1 | Me | 4-F—Ph | 2,4-di-F—Ph | O | 39-40 | |
| 2 | Me | 4-F—Ph | 2-Cl, 4-F—Ph | O | 71-73 | |
| 4 | Me | 2-Cl, 4-F—Ph | 2-Cl, 4-F—Ph | O | | 369 |
| 5 (Ex. 3) | Me | 2-Cl, 4-F—Ph | 2,4-di-F—Ph | O | ** | ** |
| 6 | Me | 4-CN, 2-F—Ph | 2-Cl, 4-F—Ph | O | 126-128 | |
| 7 | Me | 4-CN, 2-F—Ph | 2,4-di-F—Ph | O | 131-133 | |
| 8 | Me | 2-Cl, 4-F—Ph | 2-F, 4-CN—Ph | O | 139-141 | |
| 11 | Me | 2,4-di-F—Ph | 2-Cl, 4-F—Ph | O | | 353 |
| 12 | Me | 2,4-di-F—Ph | 2-Cl, 4-MeO—Ph | O | | 356 |
| 13 | Me | 2,4-di-F—Ph | 2,4-di-F—Ph | O | 62-64 | |
| 24 | Me | 2,4-di-F—Ph | 2,6-di-F—Ph | C(=O) | | 349 |
| 26 | Me | 2,4-di-F—Ph | 2-F, 4-CN—Ph | O | 125-127 | |
| 27 | Me | 2,4-di-Cl—Ph | 2-Cl, 6-F—Ph | C(=O) | | 399 |
| 28 | Me | 2,4-di-F—Ph | 2-Cl, 6-F—Ph | C(=O) | | 365 |
| 31 | Me | 2-Cl, 4-F—Ph | 2-Cl, 4-MeO—Ph | O | | 381 |
| 32 (Ex. 7) | Me | 2,4-di-F—Ph | 2,4-di-F—Ph | C(=O) | ** | ** |
| 35 | Me | 2-Cl, 4-CN—Ph | 2,4-di-F—Ph | O | 132-134 | |
| 36 | Me | 2-Cl, 4-CN—Ph | 2,4-di-F—Ph | O | 123-125 | |
| 40 (Ex. 1) | Me | 4-CN, 2,6-di-F—Ph | 2-Cl, 4-F—Ph | NH | ** | ** |
| 41 | Me | 4-F—Ph | 2-Cl, 4-F—Ph | NH | | 334 |
| 42 | Me | 2-Cl, 4-F—Ph | 2-Cl, 4-F—Ph | NH | | 369 |
| 43 | Me | 2-Cl, 4-CN—Ph | 2-Cl, 4-F—Ph | O | 133-135 | |
| 44 | Me | 2,4-di-Cl—Ph | 2-Cl, 4-F—Ph | NH | | 384 |
| 45 (Ex. 2) | Me | 4-Cl, 2-F—Ph | 2-Cl, 4-F—Ph | NH | ** | ** |
| 46 | Me | 2,6-di-Cl—Ph | 2-Cl, 4-F—Ph | C(=O) | | 397 |
| 47 | Me | 2-Cl, 4-F—Ph | 2,6-di-F—Ph | C(=O) | | 365 |
| 48 | Br | 2,4-di-F—Ph | 2-Cl,4-F—Ph | C(=O) | 154-156 | |
| 49 | Me | 2,4-di-F—Ph | 2-Cl, 4-F—Ph | NH | | 352 |
| 50 | Me | 2-Cl, 4-F—Ph | 2,6-di-F—Ph | NH | | 352 |
| 51 | Me | 2,4,6-tri-Cl | 2-Cl, 6-F—Ph | C(=O) | | 433 |
| 52 (Ex. 10) | CN | 2-Cl, 4-F—Ph | 2,6-di-F—Ph | C(=O) | ** | ** |
| 56 (Ex. 6) | Me | 4-Cl—Ph | 2,6-di-F—Ph | S | ** | ** |
| 57 | Me | 2-Cl, 4-F—Ph | 2,4-di-F—Ph | NH | | 352 |
| 58 | Me | 2-Br, 4-F—Ph | 2-Cl, 4-F—Ph | NH | | 412 |
| 59 | Me | 2-Cl, 4-F—Ph | 2,4,6-tri-F—Ph | C(=O) | | 383 |
| 60 | Me | 2,4-di-F—Ph | 2,4,6-tri-F—Ph | C(=O) | * | * |
| 62 | Me | 4-Cl—Ph | 2,6-di-F—Ph | S(=O)₂ | | 383 |
| 63 | Me | 4-Cl—Ph | 2,6-di-F—Ph | S(=O) | | 367 |
| 64 | Me | 2,4-di-F—Ph | 2,6-di-F—Ph | NH | | 336 |
| 65 | Me | 2,4-di-Cl—Ph | 2,6-di-F—Ph | NH | | 368 |
| 73 | Me | 2,4-di-F—Ph | 2-Br, 4-F—Ph | C(=O) | | 409 |
| 78 | Me | 2-Cl, 4-F—Ph | 2-Br—Ph | C(=O) | | 409 |
| 81 | Me | 2-Br, 4-F—Ph | 2-I—Ph | C(=O) | | 501 |
| 83 | Me | 2-Cl, 4-F—Ph | 2-Br, 4-F—Ph | C(=O) | * | * |
| 89 | Me | 2,4-di-F—Ph | 2,4-di-Cl—Ph | C(=O) | | 381 |
| 91 | Me | 2-Cl, 4-F—Ph | 2,6-di-Cl—Ph | N(OH) | | 384 |
| 93 | Me | 2-Cl, 4-F—Ph | 2-Br, 6-F—Ph | C(=O) | | 427 |
| 96 | Me | 2-Cl, 4-F—Ph | 3,5-di-Cl-4-pyridinyl | C(=O) | | 398 |
| 102 | Me | 2,4-di-F—Ph | 2,6-di-F, 4-Br—Ph | C(=O) | | 429 |

*See Index Table D or ¹H NMR data.
**See synthesis example for ¹H NMR.

INDEX TABLE D

| Compd. No. | ¹H NMR Data (CDCl₃ solution)ᵃ |
|---|---|
| 22 | δ 7.57 (t, 1H), 7.45-7.36 (m, 1H), 7.28-7.24 (m, 1H), 7.16-7.11 (m, 1H), 7.02-6.98 (m, 1H), 6.86-6.82 (m, 1H), 5.88 (d, 1H), 3.60 (s, 3H), 2.26 (s, 3H), 2.2 (br s, 1H). |
| 60 | δ 7.42-7.36 (m, 1H), 6.82-6.76 (m, 1H), 6.62-6.50 (m, 3H), 3.69 (s, 3H), 2.46 (s, 3H). |
| 71 | δ 7.55-7.35 (m, 1H), 7.28-6.69 (m, 5H), 5.78 (d, 1H), 3.51 (s, 3H), 2.16 (s, 3H), 2.2 (br s, 1H). |
| 82 | δ 7.26-7.15 (m, 2H), 7.0-7.12 (m, 1H), 6.40 (m, 2H), 6.0 (d, 1H), 3.46 (s, 3H), 2.38 (s, 3H), 2.42 (br s, 1H). |

INDEX TABLE D-continued

| Compd. No. | ¹H NMR Data (CDCl₃ solution)ᵃ |
|---|---|
| 83 | δ 7.26-7.12 (m, 3H), 6.94 (m, 1H), 6.85 (dd, 1H), 6.78-6.70 (m, 1H), 3.57 (s, 3H), 2.49 (s, 3H), 2.2 (br s, 1H). |
| 95 | δ 7.38-7.27 (m, 2H), 6.97-6.92 (m, 1H), 6.82-6.78 (m, 1H), 6.68-6.61 (m, 2H), 5.88 (d, 1H), 3.46 (s, 3H), 2.36 (s, 3H), 2.2 (br s, 1H). |
| 166 | δ 8.37-8.28 (m, 2H), 7.43 (m, 1H), 6.91 (m, 1H), 6.74 (m, 1H), 5.84 (m, 1H), 3.57 (s, 3H), 2.38 (m, 1H), 2.20 (s, 3H). |

INDEX TABLE D-continued

| Compd. No. | $^1$H NMR Data (CDCl$_3$ solution)$^a$ |
|---|---|
| 167 | δ 8.69 (s, 1H), 8.67 (s, 1H), 7.42 (m, 1H), 6.79 (m, 1H), 6.68 (m, 1H), 5.87 (m, 1H), 3.66 (s, 3H), 2.18 (s, 3H), 2.08 (m, 1H). |

$^{a1}$HNMR data are in ppm downfield from tetramethylsilane. Couplings are designated by (s)—singlet, (d)—doublet, (t)—triplet, (m)—multiplet, (dd)—doublet of doublets and (br s)—broad singlet.

BIOLOGICAL EXAMPLES OF THE INVENTION

General protocol for preparing test suspensions for Tests A-F: the test compounds were first dissolved in acetone in an amount equal to 3% of the final volume and then suspended at the desired concentration (in ppm) in acetone and purified water (50/50 mix by volume) containing 250 ppm of the surfactant Trem® 014 (polyhydric alcohol esters). The resulting test suspensions were then used in Tests A-F. Spraying a 200 ppm test suspension to the point of run-off on the test plants was the equivalent of a rate of 800 g/ha. Unless otherwise indicated, the rating values indicate a 200 ppm test suspension was used. (An asterisk "*" next to the rating value indicates a 40 ppm test suspension was used.)

Test A

The test suspension was sprayed to the point of run-off on tomato seedlings. The following day the seedlings were inoculated with a spore suspension of *Botrytis cinerea* (the causal agent of tomato *Botrytis*) and incubated in saturated atmosphere at 20° C. for 48 h, and then moved to a growth chamber at 24° C. for 3 days, after which time visual disease ratings were made.

Test B

The test suspension was sprayed to the point of run-off on tomato seedlings. The following day the seedlings were inoculated with a spore suspension of *Alternaria solani* (the causal agent of tomato early blight) and incubated in a saturated atmosphere at 27° C. for 48 h, and then moved to a growth chamber at 20° C. for 5 days, after which time visual disease ratings were made.

Test C

The test suspension was sprayed to the point of run-off on wheat seedlings. The following day the seedlings were inoculated with a spore suspension of *Septoria nodorum* (the causal agent of *Septoria* glume blotch) and incubated in a saturated atmosphere at 24° C. for 48 h, and then moved to a growth chamber at 20° C. for 6 days, after which time visual disease ratings were made.

Test D

The test suspension was sprayed to the point of run-off on wheat seedlings. The following day the seedlings were inoculated with a spore suspension of *Septoria tritici* (the causal agent of wheat leaf blotch) and incubated in saturated atmosphere at 24° C. for 48 h, and then moved to a growth chamber at 20° C. for 19 days, after which time visual disease ratings were made.

Test E1

Wheat seedlings were inoculated with a spore suspension of *Puccinia recondite* f. sp. *tritici* (the causal agent of wheat leaf rust) and incubated in a saturated atmosphere at 20° C. for 24 h, and then moved to a growth chamber at 20° C. for 2 days. After 2 days, the test suspension was sprayed to the point of run-off on the wheat seedlings, and then the seedlings were moved back to the growth chamber at 20° C. for 6 days. Upon removal, visual disease ratings were made.

Test E2

The test suspension was sprayed to the point of run-off on wheat seedlings. The following day the seedlings were inoculated with a spore suspension of *Puccinia recondite* f. sp. *tritici* (the causal agent of wheat leaf rust) and incubated in a saturated atmosphere at 20° C. for 24 h, and then moved to a growth chamber at 20° C. for 7 days, after which time visual disease ratings were made.

Test F

The test suspension was sprayed to the point of run-off on wheat seedlings. The following day the seedlings were inoculated with a spore dust of *Blumeria graminis* f. sp. *tritici*, (also known as *Erysiphe graminis* f. sp. tritici, the causal agent of wheat powdery mildew) and incubated in a growth chamber at 20° C. for 8 days, after which time visual disease ratings were made.

Results for Tests A-F are given in Table A. In the Table, a rating of 100 indicates 100% disease control and a rating of 0 indicates no disease control (relative to the controls). A dash (-) indicates no test results. An asterisk "*" next to the rating value indicates a 40 ppm test suspension was used.

TABLE A

| Cmpd. No | Test A | Test B | Test C | Test D | Test E1 | Test E2 | Test F |
|---|---|---|---|---|---|---|---|
| 1 | 100 | 0 | 0 | 0 | 38 | 68 | 91 |
| 2 | 100 | 0 | 0 | 100 | 77 | 97 | 99 |
| 3 | 100 | 100 | 100 | 100 | 99 | 100 | 100 |
| 4 | 98 | 0 | 0 | 100 | 75 | 98 | 97 |
| 5 | 87 | 0 | 0 | 97 | 23 | 92 | 66 |
| 6 | 100 | 59 | 0 | 100 | 0 | 99 | 100 |
| 7 | 0 | 96 | 0 | 100 | 0 | 9 | 0 |
| 8 | 100 | 0 | 0 | 99 | 0 | 40 | 99 |
| 9 | 100 | 0 | 0 | 100 | 100 | 100 | 99 |
| 10 | 100 | 100 | 99 | 100 | 98 | 100 | 100 |
| 11 | 100 | 0 | 0 | 95 | 91 | 97 | 96 |
| 12 | 100 | 93 | 0 | 100 | 65 | 89 | 98 |
| 13 | 100 | 0 | 0 | 0 | 66 | 0 | 72 |
| 14 | 100 | 100 | 99 | 100 | 96 | 100 | 100 |
| 15 | 100 | 100 | 86 | 100 | 68 | 100 | 100 |
| 16 | 100 | 99 | 0 | 100 | 54 | 100 | 93 |
| 17 | 100 | 94 | 60 | 100 | 83 | 100 | 100 |
| 18 | 100 | 83 | 0 | 100 | 100 | 100 | 100 |
| 19 | 99 | 100 | 100 | 100 | 100 | 100 | 100 |
| 20 | 97* | 97* | 0* | 100* | 99* | 99* | 92* |
| 21 | 99 | 100 | 100 | 100 | 100 | 100 | 98 |
| 22 | 88 | 84 | 0 | 100 | 17 | 88 | 0 |
| 23 | 100 | 67 | 87 | 100 | 98 | 100 | 84 |
| 24 | 9 | 0 | 0 | 0 | 9 | 79 | 96 |
| 25 | 100 | 99 | 89 | 100 | 9 | 100 | 96 |
| 26 | 100 | 0 | 0 | — | 0 | 79 | 64 |
| 27 | 0 | 0 | 0 | 0 | 0 | 0 | 81 |
| 28 | 56 | 0 | 0 | 0 | 0 | 8 | 79 |
| 29 | 100 | 64 | 0 | — | 0 | 100 | 96 |
| 30 | 100 | 9 | 0 | 100 | 100 | 99 | 99 |
| 31 | 100 | 0 | 0 | 100 | 0 | 92 | 96 |
| 32 | 26 | 0 | 0 | — | 0 | 0 | 0 |
| 33 | 100 | 100 | 100 | 100 | 99 | 100 | 100 |
| 34 | 100 | 99 | 100 | 100 | 84 | 99 | 100 |
| 35 | 98 | 0 | 0 | 100 | 9 | 73 | 0 |
| 36 | 96 | 0 | 0 | 100 | 18 | 100 | 100 |
| 37 | 100 | 99 | 100 | 100 | | 100 | 100 |

TABLE A-continued

| Cmpd. No | Test A | Test B | Test C | Test D | Test E1 | Test E2 | Test F |
|---|---|---|---|---|---|---|---|
| 38 | 85 | 99 | 100 | 100 | 0 | 100 | 98 |
| 39 | 95 | 58 | 60 | 100 | 97 | 100 | 99 |
| 40 | 100 | 99 | 99 | 100 | 91 | 100 | 100 |
| 41 | 100 | 64 | 0 | 98 | 0 | 41 | 0 |
| 42 | 99 | 99 | 0 | 100 | 32 | 99 | 100 |
| 43 | 98 | 0 | 0 | 100 | 0 | 98 | 97 |
| 44 | 99* | 0* | 0* | 99* | 0* | 99* | 100* |
| 45 | 98* | 33* | 0* | 100* | 0* | 95* | 100* |
| 46 | — | — | — | — | — | — | — |
| 47 | — | — | — | — | — | — | — |
| 48 | 26 | 0 | 0 | 99 | — | 0 | 0 |
| 49 | 100* | 0* | 0* | 96* | — | 74* | 87* |
| 50 | 99 | 93 | 0 | 100 | 0 | 79 | 98 |
| 51 | — | — | — | — | — | — | — |
| 52 | — | — | — | — | — | — | — |
| 53 | 93* | 99* | 0* | 100* | 0* | 93* | 43* |
| 54 | 100 | 100 | 99 | 100 | 100 | 99 | 99 |
| 55 | 99 | 97 | 78 | 100 | 99 | 100 | 95 |
| 56 | 0 | 0 | 0 | 0 | 60 | 27 | 97 |
| 57 | 99* | 0* | 0* | 81* | 0* | 18* | 97* |
| 58 | 100* | 8* | 0* | 100* | 0* | 98* | 97* |
| 59 | 66 | 0 | 0 | 58 | 0 | 80 | 100 |
| 60 | 75 | 0 | 0 | 0 | 0 | 55 | 99 |
| 61 | 100 | 100 | 99 | 100 | 99 | 100 | 100 |
| 62 | 0 | 0 | 0 | 0 | 0 | 28 | 94 |
| 63 | 0 | 0 | 0 | 0 | 0 | 28 | 76 |
| 64 | 99 | 0 | 0 | 48 | 0 | 55 | 97 |
| 65 | 100 | 0 | 0 | 100 | 9 | 89 | 100 |
| 66 | 100 | 100 | 95 | 100 | 55 | 100 | 99 |
| 67 | 57 | 9 | 0 | 100 | 28 | 90 | 100 |
| 68 | 100 | 88 | 99 | 100 | 100 | 100 | 100 |
| 69 | 99 | 100 | 96 | 100 | 0 | 99 | 97 |
| 70 | — | 99 | 60 | 100 | 94 | 100 | 99 |
| 71 | — | 78* | 73* | 100* | 88* | 99* | 99* |
| 72 | — | 53* | 0* | 100* | 18* | 96* | 98* |
| 73 | — | 60* | 0* | 14* | 0* | 0* | 34* |
| 74 | — | 100 | 92 | 99 | 0 | 99 | 98 |
| 75 | — | 100* | 87* | 100* | 74* | 100* | 99* |
| 76 | — | 99 | 60 | 100 | 99 | 100 | 100 |
| 77 | — | 93 | 0 | 99 | 0 | 79 | 89 |
| 78 | 0 | 31 | 40 | 0 | 0 | 79 | 99 |
| 79 | 98 | 0 | 0 | 100 | 53 | 100 | 99 |
| 80 | 99 | 97 | 69 | 100 | 99 | 99 | 99 |
| 81 | 54 | 46 | 0 | 0 | — | 0 | 99 |
| 82 | 99 | 100 | 92 | 99 | 27 | 100 | 100 |
| 83 | 55* | 0* | 0* | 25* | 0* | 74* | 99* |
| 84 | 96* | 100* | 99* | 100* | 41* | 100* | 100* |
| 85 | 97 | 84 | 0 | 100 | 9 | 100 | 50 |
| 86 | 99 | 100* | 99* | 100 | 99* | 100 | 100 |
| 87 | 100 | 0* | 100 | 99* | 0* | 99 | 99 |
| 88 | — | 0 | 0 | 99 | 0 | 68 | 89 |
| 89 | — | 0 | 0 | 93 | 0 | 89 | 100 |
| 90 | — | 100* | 99* | 100* | 74* | 100* | 100 |
| 91 | — | 0 | 0 | 100 | 0 | 68 | 99 |
| 92 | — | 99* | 94* | 100* | 74* | 99* | 100* |
| 93 | 90 | — | — | 7 | — | 91 | 100 |
| 94 | 99 | — | — | 100 | — | 100 | 100 |
| 95 | 94* | — | — | 99* | — | 98* | 95* |
| 96 | 60* | 0* | 0* | 0* | — | 0* | 26* |
| 97 | 99 | — | — | 100 | — | 100 | 99 |
| 98 | 94* | — | — | 100* | — | 100* | 100* |
| 99 | 97 | — | — | 100 | — | 100 | 99 |
| 100 | — | — | — | 100 | — | 100 | 99 |
| 101 | — | — | — | 100 | — | 99 | 72 |
| 102 | 0 | — | — | 0 | — | 55 | 97 |
| 103 | 99 | — | — | 98 | — | 96 | 95 |
| 104 | 0* | — | — | 98* | — | 97* | 72* |
| 105 | 0* | — | — | 100* | — | 98* | 81* |
| 106 | 98 | — | — | 100 | — | 97 | 0 |
| 107 | 9* | — | — | 99* | — | 99* | 99* |
| 108 | 99* | — | — | 100* | — | 100* | 100* |
| 109 | 0* | — | — | 100* | — | 98* | 97* |
| 110 | 0* | — | — | 100* | — | 98* | 99* |
| 111 | 100 | — | — | 100 | — | 100 | 100 |
| 112 | 80 | — | — | 100 | — | 100 | 97 |
| 113 | 99 | — | — | 100 | — | 100 | 100 |
| 114 | 21 | — | — | 100 | — | 98 | 98 |
| 115 | 88* | — | — | 100* | — | 94* | 99* |
| 116 | 0* | — | — | 78* | — | 9* | 0* |
| 117 | 100 | — | — | 100 | — | 100 | 100 |
| 118 | 100 | — | — | 100 | — | 99 | 100 |
| 119 | 100 | — | — | 100 | — | 100 | 100 |
| 120 | 100 | — | — | 100 | — | 100 | 100 |
| 121 | 97* | — | — | 100* | — | 100* | 100* |
| 122 | 98* | — | — | 100* | — | 100* | 99* |
| 123 | 87* | — | — | 100* | — | 99* | 90* |
| 124 | 99 | — | — | 100 | — | 100 | 100 |
| 125 | 82 | — | — | 100 | — | 100 | 87 |
| 126 | 100 | — | — | 100 | — | 100 | 100 |
| 127 | 76 | — | — | 100 | — | 91 | 99 |
| 128 | 43* | — | 0* | 100* | — | 85* | 56* |
| 129 | 100 | — | — | 100 | — | 99 | 100 |
| 130 | 100 | — | — | 100 | — | 100 | 100 |
| 131 | 98 | — | — | 100 | — | 100 | 98 |
| 132 | 0 | — | — | 100* | — | 99* | 100 |
| 133 | 100 | — | — | 100 | — | 100 | 99 |
| 134 | 100 | — | — | 100 | — | 100 | 99 |
| 135 | 100 | — | — | 100 | — | 100 | 99 |
| 136 | 100 | — | — | 100 | — | 100 | 100 |
| 137 | 100 | — | — | 100 | — | 100 | 100 |
| 138 | 66* | — | — | 16* | — | 55* | 93* |
| 139 | 83* | — | — | 100* | — | 80* | 96* |
| 140 | 100* | — | 99* | 100* | — | 99* | 100* |
| 141 | 100* | — | 97* | 100* | — | 99* | 99* |
| 142 | 100* | — | 60* | 100* | — | 100* | 100* |
| 143 | 100* | — | 0* | 100* | — | 99* | 98* |
| 144 | 78* | — | 0* | 100* | — | 100* | 98* |
| 145 | 26* | — | 0* | 35* | — | 82* | 73* |
| 146 | 0 | — | — | 18 | — | 17 | 0 |
| 147 | 0* | — | — | 0* | — | 17* | 0* |
| 148 | 100 | — | — | 100 | — | 100 | 99 |
| 149 | 100 | — | — | 100 | — | 100 | 100 |
| 150 | 8 | — | — | 0 | — | 9 | 0 |
| 151 | 16 | — | — | 0 | — | 99 | 43 |
| 152 | 100* | — | — | 100* | — | 100* | 100* |
| 153 | 100* | — | — | 100* | — | 100* | 100* |
| 154 | 100 | — | — | 100 | — | 100 | 100 |
| 155 | 99* | — | — | 100* | — | 100* | 99* |
| 156 | 100* | — | — | 100* | — | 99* | 99* |
| 157 | 100* | — | — | 100* | — | 100* | 100* |
| 158 | 0 | — | — | 8 | — | 0 | 13 |
| 159 | 0 | — | — | 0 | — | 0 | 0 |
| 160 | 95* | — | — | 100* | — | 100* | 98* |
| 161 | 94* | — | — | 100* | — | 92* | 90* |
| 162 | 99* | — | — | 100* | — | 86* | 64* |
| 163 | 100 | — | — | 100 | — | 100 | 98 |
| 164 | 100 | — | — | 100 | — | 100 | 0 |
| 165 | 100 | — | — | 100 | — | 100 | 100 |
| 166 | 99* | — | — | 100* | — | 99* | 93* |
| 167 | 0* | — | — | 58* | — | 0* | 0* |
| 168 | 21* | — | — | 100* | — | 88* | 100* |
| 169 | 0* | — | — | 68* | — | 88* | 0* |
| 170 | 100* | — | — | 100* | — | 100* | 98* |
| 171 | 100* | — | — | 100* | — | 100* | 89* |
| 172 | 99* | — | — | 100* | — | 100* | 100* |
| 173 | 87* | — | — | 100* | — | 100* | 95* |

What is claimed is:

1. A compound selected from Formula I, N-oxides, and salts thereof,

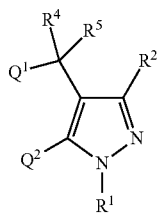

wherein
- $Q^1$ is a phenyl ring substituted with 1 to 5 substituents independently selected from $R^{3a}$;
- $Q^2$ is a phenyl ring substituted with 1 to 5 substituents independently selected from $R^{3a}$; or a 5- to 6-membered fully unsaturated heterocyclic ring, each ring containing ring members selected from carbon atoms and 1 to 3 heteroatoms independently selected from up to 2 O, up to 2 S and up to 3 N atoms, wherein up to 2 carbon ring members are independently selected from C(=O) and C(=S), each ring optionally substituted with up to 5 substituents independently selected from $R^{3a}$ on carbon atom ring members and $R^{3b}$ on nitrogen atom ring members;
- $R^1$ is $C_1$-$C_2$ alkyl, halomethyl, cyanomethyl or cyclopropyl;
- $R^2$ is H, halogen, cyano, $C_1$-$C_2$ alkyl, $C_2$-$C_4$ alkenyl, $C_2$-$C_4$ alkynyl, $C_1$-$C_2$ haloalkyl, $C_2$-$C_3$ cyanoalkyl, $C_1$-$C_2$ hydroxyalkyl, cyclopropyl, halocyclopropyl, $C_2$-$C_3$ alkoxyalkyl, $C_1$-$C_2$ alkylthio, $C_1$-$C_2$ alkoxy or $C_1$-$C_2$ haloalkoxy;
- each $R^{3a}$ is independently halogen, cyano, hydroxy, nitro, amino, $C_1$-$C_3$ alkyl, $C_2$-$C_4$ alkenyl, $C_2$-$C_4$ alkynyl, $C_1$-$C_3$ haloalkyl, $C_3$-$C_6$ cycloalkyl, $C_3$-$C_6$ halocycloalkyl, $C_4$-$C_6$ alkylcycloalkyl, $C_4$-$C_6$ cycloalkylalkyl, $C_1$-$C_3$ alkylthio, $C_1$-$C_3$ haloalkylthio, $C_1$-$C_3$ alkylsulfinyl, $C_1$-$C_3$ haloalkylsulfinyl, $C_1$-$C_3$ alkylsulfonyl, $C_1$-$C_3$ haloalkylsulfonyl, $C_1$-$C_3$ alkoxy, $C_1$-$C_3$ haloalkoxy, $C_3$-$C_6$ cycloalkoxy, $C_1$-$C_3$ alkylsulfonyloxy, $C_1$-$C_3$ haloalkylsulfonyloxy, $C_2$-$C_4$ alkylcarbonyloxy, $C_2$-$C_4$ alkylcarbonyl, $C_1$-$C_3$ alkylamino, $C_2$-$C_4$ dialkylamino, $C_2$-$C_4$ alkylcarbonylamino, —CH(=O), —NHCH(=O), —SF$_5$, —SC≡N or -U—V-T;
- each $R^{3b}$ is independently cyano, $C_1$-$C_3$ alkyl, $C_2$-$C_4$ alkenyl, $C_2$-$C_4$ alkynyl, $C_3$-$C_6$ cycloalkyl, $C_2$-$C_4$ alkoxyalkyl, $C_2$-$C_4$ alkylaminoalkyl, $C_3$-$C_4$ dialkylaminoalkyl, $C_1$-$C_3$ alkoxy, $C_2$-$C_4$ alkylcarbonyl or $C_2$-$C_4$ alkoxycarbonyl;
- $R^4$ is halogen, —OR$^7$ or —SC≡N;
- $R^5$ is H or $C_1$-$C_4$ alkyl;
- $R^7$ is H, $C_1$-$C_6$ alkyl, $C_1$-$C_6$ haloalkyl, $C_2$-$C_6$ alkenyl, $C_3$-$C_6$ alkynyl, $C_3$-$C_6$ cycloalkyl, $C_2$-$C_6$ cyanoalkyl, $C_2$-$C_6$ alkoxyalkyl, —CH(=O), —S(=O)$_2$OM$^1$ or —C(=W)R$^9$;
- $R^9$ is $C_1$-$C_6$ alkyl, $C_2$-$C_6$ alkoxyalkyl, $C_2$-$C_6$ alkylaminoalkyl, $C_3$-$C_6$ dialkylaminoalkyl, $C_2$-$C_6$ alkylthioalkyl, $C_1$-$C_6$ alkoxy or $C_1$-$C_6$ alkylthio;
- each U is independently 0, S(=O)$_n$, N(R$^{10}$) or a direct bond;
- each V is independently $C_1$-$C_6$ alkylene, $C_2$-$C_6$ alkenylene, $C_2$-$C_6$ alkynylene, $C_3$-$C_6$ cycloalkylene or $C_3$-$C_6$ cycloalkenylene, wherein up to 3 carbon atoms are independently selected from C(=O), each optionally substituted with up to 5 substituents independently selected from halogen, cyano, nitro, hydroxy, $C_1$-$C_6$ alkyl, $C_1$-$C_6$ haloalkyl, $C_1$-$C_6$ alkoxy and $C_1$-$C_6$ haloalkoxy;
- each T is independently cyano, N(R$^{11a}$)(R$^{11b}$), OR$^{12}$ or S(=O)$_n$R$^{12}$;
- each R$^{10}$ is independently H, $C_1$-$C_6$ alkyl, $C_1$-$C_6$ haloalkyl, $C_2$-$C_6$ alkylcarbonyl, $C_2$-$C_6$ alkoxycarbonyl, $C_2$-$C_6$ (alkylthio)carbonyl, $C_2$-$C_6$ alkoxy(thiocarbonyl), $C_4$-$C_8$ cycloalkylcarbonyl, $C_4$-$C_8$ cycloalkoxycarbonyl, $C_4$-$C_8$ (cycloalkylthio)carbonyl or $C_4$-$C_8$ cycloalkoxy(thiocarbonyl);
- each R$^{11a}$ and R$^{11b}$ is independently H, $C_1$-$C_6$ alkyl, $C_1$-$C_6$ haloalkyl, $C_2$-$C_6$ alkenyl, $C_3$-$C_6$ alkynyl, $C_3$-$C_6$ cycloalkyl, $C_3$-$C_6$ halocycloalkyl, $C_2$-$C_6$ alkylcarbonyl, $C_2$-$C_6$ alkoxycarbonyl, $C_2$-$C_6$ (alkylthio)carbonyl, $C_2$-$C_6$ alkoxy(thiocarbonyl), $C_4$-$C_8$ cycloalkylcarbonyl, $C_4$-$C_8$ cycloalkoxycarbonyl, $C_4$-$C_8$ (cycloalkylthio)carbonyl or $C_4$-$C_8$ cycloalkoxy(thiocarbonyl); or
- a pair of R$^{11a}$ and R$^{11b}$ are taken together with the nitrogen atom to which they are attached to form a form a 3- to 6-membered heterocyclic ring, the ring optionally substituted with up to 5 substituents independently selected from R$^{13}$;
- each R$^{12}$ is independently H, $C_1$-$C_6$ alkyl, $C_1$-$C_6$ haloalkyl, $C_2$-$C_6$ alkenyl, $C_3$-$C_6$ alkynyl, $C_3$-$C_6$ cycloalkyl, $C_3$-$C_6$ halocycloalkyl, $C_2$-$C_6$ alkylcarbonyl, $C_2$-$C_6$ alkoxycarbonyl, $C_2$-$C_6$ (alkylthio)carbonyl, $C_2$-$C_6$ alkoxy(thiocarbonyl), $C_4$-$C_8$ cycloalkylcarbonyl, $C_4$-$C_8$ cycloalkoxycarbonyl, $C_4$-$C_8$ (cycloalkylthio)carbonyl or $C_4$-$C_8$ cycloalkoxy(thiocarbonyl);
- each R$^{13}$ is independently halogen, $C_1$-$C_6$ alkyl, $C_1$-$C_6$ haloalkyl or $C_1$-$C_6$ alkoxy;
- W is O or S;
- M$^1$ is K, Na or Li; and
- each n is independently 0, 1 or 2;
- provided that when $Q^2$ is a phenyl ring which is not substituted with R$^{3a}$ at either ortho position, then $Q^1$ is substituted by at least one R$^{3a}$ at an ortho position.

2. A compound of claim 1 wherein:
- $Q^1$ is a phenyl ring substituted with 1 to 3 substituents independently selected from R$^{3a}$;
- $Q^2$ is a phenyl ring substituted with 1 to 3 substituents independently selected from R$^{3a}$; or a pyrazolyl, imidazolyl, pyridinyl, pyridazinyl, pyrazinyl or pyrimidinyl ring, each ring optionally substituted with up to 3 substituents independently selected from R$^{3a}$ on carbon atom ring members and R$^{3b}$ on nitrogen atom ring members;
- $R^1$ is $C_1$-$C_2$ alkyl, —CH$_2$F, —CH$_2$Cl or cyclopropyl;
- $R^2$ is H, halogen, cyano, $C_1$-$C_2$ alkyl, $C_2$-$C_4$ alkenyl, halomethyl, cyanomethyl, hydroxymethyl, $C_2$-$C_3$ alkoxyalkyl, $C_1$-$C_2$ alkoxy or $C_1$-$C_2$ haloalkoxy;
- each R$^{3a}$ is independently halogen, cyano, $C_1$-$C_2$ alkyl, $C_1$-$C_2$ haloalkyl, cyclopropyl, $C_1$-$C_2$ alkoxy, $C_1$-$C_2$ alkylthio, $C_2$-$C_3$ alkylcarbonyl or —U—V-T;
- each R$^{3b}$ is independently cyano, $C_1$-$C_2$ alkyl, cyclopropyl or $C_2$-$C_3$ alkoxyalkyl;
- $R^4$ is Br, Cl, F, —OR$^7$ or —SC≡N;
- $R^5$ is H or methyl;
- $R^7$ is H, $C_1$-$C_3$ alkyl, $C_2$-$C_6$ alkenyl, $C_1$-$C_3$ haloalkyl, cyclopropyl, $C_2$-$C_3$ cyanoalkyl, $C_2$-$C_6$ alkoxyalkyl, —S(=O)$_2$OM$^1$ or —C(=W)R$^9$;
- $R^9$ is methyl or methoxy;
- each U is independently O, N(R$^{10}$) or a direct bond;
- each R$^{10}$ is independently H or methyl;
- each V is independently $C_1$-$C_3$ alkylene, wherein up to 1 carbon atom is selected from C(=O);

each T is independently N(R$^{11a}$)(R$^{11b}$b) or OR$^{12}$;
each R$^{11a}$ and R$^{11b}$ is independently H or methyl;
each R$^{12}$ is independently H, C$_1$-C$_6$ alkyl or C$_1$-C$_6$ haloalkyl;
W is O; and
M$^1$ is Na or K.

3. A compound of claim 2 wherein:
Q$^2$ is a phenyl ring substituted with 1 to 3 substituents independently selected from R$^{3a}$; or a pyrazolyl, imidazolyl or pyridinyl ring, each ring optionally substituted with 1 to 3 substituents independently selected from R$^{3a}$ on carbon atom ring members and R$^{3b}$ on nitrogen atom ring members;
R$^1$ is methyl, —CH$_2$F or —CH$_2$Cl;
R$^2$ is halogen, cyano, C$_1$-C$_2$ alkyl, halomethyl, cyanomethyl, hydroxymethyl, C$_1$-C$_2$ alkoxy or C$_1$-C$_2$ haloalkoxy;
each R$^{3a}$ is independently halogen, cyano, methyl, halomethyl, cyclopropyl, methoxy, methylthio, methylcarbonyl or —U—V-T;
each R$^{3b}$ is methyl;
R$^4$ is Br, Cl, F or —OR$^7$;
R$^7$ is H, C$_1$-C$_3$ alkyl, C$_1$-C$_3$ haloalkyl, —S(=O)$_2$OM$^1$ or —C(=W)R$^9$;
each U is independently O, NH or a direct bond;
each V is C$_1$-C$_3$ alkylene; and
each R$^{12}$ is independently H, methyl or halomethyl.

4. A compound of claim 3 wherein:
Q$^2$ is a phenyl ring substituted with 1 to 3 substituents independently selected from R$^{3a}$;
R$^1$ is methyl;
R$^2$ is halogen, cyano, methyl, halomethyl or methoxy;
each R$^{3a}$ is independently halogen, cyano, methyl, halomethyl or methoxy;
R$^4$ is —OR$^7$;
R$^5$ is H;
R$^7$ is H, methyl or —C(=W)R$^9$; and
R$^9$ is methyl.

5. A compound of claim 4 wherein:
R$^2$ is Br, Cl, methyl or methoxy;
each R$^{3a}$ is independently halogen, cyano or methoxy; and
R$^7$ is H.

6. A compound of claim 5 wherein:
R$^2$ methyl;
each R$^{3a}$ is independently Br, Cl, F, cyano or methoxy; and
one of Q$^1$ and Q$^2$ is substituted with 2 to 3 substituents and the other of Q$^1$ and Q$^2$ is substituted with 1 to 2 substituents.

7. The compound of claim 1 which is selected from the group:
α-(2-chloro-4-fluorophenyl)-5-(2-chloro-6-fluorophenyl)-1,3-dimethyl-1H-pyrazole-4-methanol;
(αS)-α-(2-chloro-4-fluorophenyl)-5-(2-chloro-6-fluorophenyl)-1,3-dimethyl-1H-pyrazole-4-methanol;
(αR)-α-(2-chloro-4-fluorophenyl)-5-(2-chloro-6-fluorophenyl)-1,3-dimethyl-1H-pyrazole-4-methanol;
α-(2-chloro-4-fluorophenyl)-5-(2,6-fluorophenyl)-1,3-dimethyl-1H-pyrazole-4-methanol;
(αS)-α-(2-chloro-4-fluorophenyl)-5-(2,6-difluorophenyl)-1,3-dimethyl-1H-pyrazole-4-methanol;
(αR)-α-(2-chloro-4-fluorophenyl)-5-(2,6-fluorophenyl)-1,3-dimethyl-1H-pyrazole-4-methanol;
α,5-bis(2-chloro-4-fluorophenyl)-1,3-dimethyl-1H-pyrazole-4-methanol;
5-(2-bromophenyl)-α-(2-chloro-4-fluorophenyl)-1,3-dimethyl-1H-pyrazole-4-methanol;
α-(2-chloro-4-fluorophenyl)-5-(2,6-dichlorophenyl)-1,3-dimethyl-1H-pyrazole-4-methanol;
α-(2-chloro-4-fluorophenyl)-1,3-dimethyl-5-(2,4,6-trifluorophenyl)-1H-pyrazole-4-methanol;
α-(2-bromo-4-fluorophenyl)-5-(2,6-dichlorophenyl)-1,3-dimethyl-1H-pyrazole-4-methanol;
α-(2-bromo-4-fluorophenyl)-5-(2-chloro-fluorophenyl)-1,3-dimethyl-1H-pyrazole-4-methanol;
3-bromo-5-(2-chloro-4-fluorophenyl)-α-(2,4-difluorophenyl)-1-methyl-1H-pyrazole-4-methanol;
5-(2-chloro-4-fluorophenyl)-α-(2,4-difluorophenyl)-1,3-dimethyl-1H-pyrazole-4-methanol;
5-(2,4-dichlorophenyl)-α-(2,4-difluorophenyl)-1,3-dimethyl-1H-pyrazole-4-methanol;
5-(2-chloro-6-fluorophenyl)-α-(2,4-difluorophenyl)-1,3-dimethyl-1H-pyrazole-4-methanol;
α-(2,4-difluorophenyl)-5-(2,6-dichlorophenyl)-1,3-dimethyl-1H-pyrazole-4-methanol;
4-[4-[(2,4-difluorophenyl)hydroxymethyl]-1,3-dimethyl-1H-pyrazol-5-yl]-3,5-difluorobenzonitrile;
5-(2-chloro-6-fluorophenyl)-α-(2,4-dichlorophenyl)-1,3-dimethyl-1H-pyrazole-4-methanol;
5-(2-chloro-6-fluorophenyl)-α-(2,6-dichlorophenyl)-1,3-dimethyl-1H-pyrazole-4-methanol;
5-(2-chloro-4-fluorophenyl)-1,3-dimethyl-α-(2,4,6-trifluorophenyl)-1H-pyrazole-4-methanol;
5-(2-bromo-4-fluorophenyl)-1,3-dimethyl-α-(2,4,6-trifluorophenyl)-1H-pyrazole-4-methanol;
5-(2-chloro-6-fluorophenyl)-α-(2-chloro-4-methoxyphenyl)-1,3-dimethyl-1H-pyrazole-4-methanol;
3-bromo-α-(2-chloro-4-fluorophenyl)-5-(2,6-difluorophenyl)-1-methyl-1H-pyrazole-4-methanol;
3-chloro-α-(2-chloro-4-fluorophenyl)-5-(2,6-difluorophenyl)-1-methyl-1H-pyrazole-4-methanol;
α-(2-chloro-4-fluorophenyl)-5-(2,6-difluorophenyl)-3-methoxy-1-methyl-1H-pyrazole-4-methanol;
α-(2-chloro-4-fluorophenyl)-5-(2-chloro-6-fluorophenyl)-3-methoxy-1-methyl-1H-pyrazole-4-methanol;
5-(2,6-difluorophenyl)-α-(4-fluoro-2-methylphenyl)-3-methoxy-1-methyl-1H-pyrazole-4-methanol;
α-(2-chloro-4-methoxphenyl)-5-(2,6-difluorophenyl)-3-methoxy-1-methyl-1H-pyrazole-4-methanol;
5-(2,6-difluorophenyl)-3-methoxy-α-(4-methoxy-2-methylphenyl)-1-methyl-1H-pyrazole-4-methanol;
5-(2-chloro-6-fluorophenyl)-α-(2-chloro-4-methoxyphenyl)-3-methoxy-1-methyl-1H-pyrazole-4-methanol;
3-chloro-5-(2,6-difluorophenyl)-α-(4-methoxy-2-methylphenyl)-1-methyl-1H-pyrazole-4-methanol;
3-chloro-5-(2,6-difluorophenyl)-α-(2-fluoro-4-methoxyphenyl)-1-methyl-1H-pyrazole-4-methanol;
3-chloro-α-(2-chloro-4-methoxyphenyl)-5-(2,6-difluorophenyl)-1-methyl-1H-pyrazole-4-methanol; and
3-bromo-5-(2,6-difluorophenyl)-α-(4-methoxy-2-methylphenyl)-1-methyl-1H-pyrazole-4-methanol.

8. A fungicidal composition comprising (a) a compound of claim 1; and (b) at least one other fungicide.

9. A fungicidal composition comprising (a) a compound of claim 1; and (b) at least one additional component selected from the group consisting of surfactants, solid diluents and liquid diluents.

10. A method for controlling plant diseases caused by fungal plant pathogens comprising applying to the plant or portion thereof, or to the plant seed, a fungicidally effective amount of a compound of claim 1.

* * * * *